US006413727B1

(12) United States Patent
Albertsen et al.

(10) Patent No.: US 6,413,727 B1
(45) Date of Patent: Jul. 2, 2002

(54) DIAGNOSIS FOR MUTANT APC BY IMMUNOASSAY

(75) Inventors: Hans Albertsen, Salt Lake City, UT (US); Rakesh Anand, Sandbach (GB); Mary Carlson; Joanna Groden, both of Salt Lake City, UT (US); Philip John Hedge, Winsford (GB); Geoff Joslyn, Salt Lake City, UT (US); Kenneth Kinzler, Baltimore, MD (US); Alexander Fred Markham, Crewe (GB); Yusuke Nakamura, Tokyo (JP); Andrew Thliveris, Salt Lake City, UT (US); Bert Vogelstein, Baltimore, MD (US); Raymond L. White, Salt Lake City, UT (US)

(73) Assignees: The Johns Hopkins University, Baltimore, MD (US); University of Utah, Salt Lake City, UT (US); Japanese Foundation for Cancer Research Cancer Institute, Tokyo (JP); Zeneca Limited, Chesire (GB)

( * ) Notice: Subject to any disclaimer, the term of this patent is extended or adjusted under 35 U.S.C. 154(b) by 0 days.

(21) Appl. No.: 08/449,731

(22) Filed: May 25, 1995

Related U.S. Application Data

(62) Division of application No. 08/289,548, filed on Aug. 12, 1994, now Pat. No. 5,648,212, which is a division of application No. 07/741,940, filed on Aug. 8, 1991, now Pat. No. 5,352,775.

(30) Foreign Application Priority Data

Jan. 16, 1991 (GB) ............................................. 9100962
Jan. 16, 1991 (GB) ............................................. 9100963
Jan. 16, 1991 (GB) ............................................. 9100974
Jan. 16, 1991 (GB) ............................................. 9100975

(51) Int. Cl.[7] ....................... G01N 33/574; G01N 33/53
(52) U.S. Cl. ..................... 435/7.23; 435/7.25; 436/501; 436/64; 436/66; 530/387.7
(58) Field of Search ................................ 435/7.23, 7.1; 436/64; 530/387.7

(56) References Cited

U.S. PATENT DOCUMENTS 5,098,823 A  3/1992  Bodmer et al. ................. 435/6
5,137,806 A  8/1992  LeMaistie et al. .............. 435/6

FOREIGN PATENT DOCUMENTS

WO    WO 89/01481    8/1988

OTHER PUBLICATIONS

Groden, et al., "Identification and Characterization of the *Familial Adenomatous Polyposis Coli* Gene", *Cell*, 66:589–600 (1991).
Joslyn, et al., "Identification of Delection Mutations and Three New Genes at the *Familial Polyposis Locus*", *Cell*, 66:601–613 (1991).
Kinzler, et al., "Identification of *FAP Locus* Genes from Chromosome 5q21", *Science*, 253:661–665 (1991).
Nishisho, et al., "Mutations of Chromosome 5q21 Genes in FAP and Colorectal Cancer Patients", *Science*, 253:665–669 (1991).
Orita, et al., Genomics, vol. 5, pp. 874–879, 1989.
Stanbridge, et al., "Identifying Tumor Suppressor Genes in Human Colorectal Cancer", *Science*, 247:12–13 (1990).
Fearon et al., "Identification of a Chromosome 18q Gene That is Altered in Colorectal Cancer", *Science*, 247:49–56 (1990).
Baker et al., "Chromosome 17 Deletions and p53 Gene Mutations in Colorectal Carcinomas", *Science*, 244:217–221 (1989).
Bodmer et al., "Localization of the Gene for *Familial Adenomatous Polyposis* on Chromosome 5", *Nature*, 328:614–616 (1987).

*Primary Examiner*—Yvonne Eyler
*Assistant Examiner*—Eileen B. O'Hara
(74) *Attorney, Agent, or Firm*—Banner & Witcoff Ltd.

(57) ABSTRACT

A human gene termed APC is disclosed. Methods and kits are provided for assessing mutations of the APC gene in human tissues and body samples. APC mutations are found in familial adenomatous polyposis patients as well as in sporadic colorectal cancer patients. APC is expressed in most normal tissues. These results suggest that APC is a tumor suppressor.

5 Claims, 72 Drawing Sheets

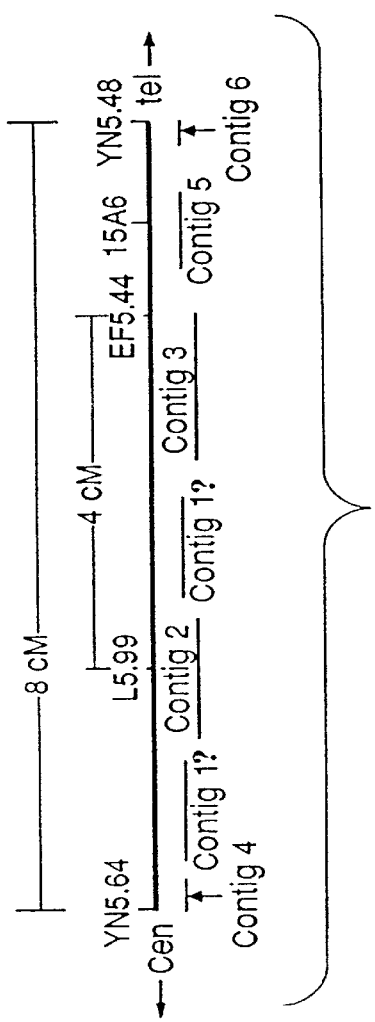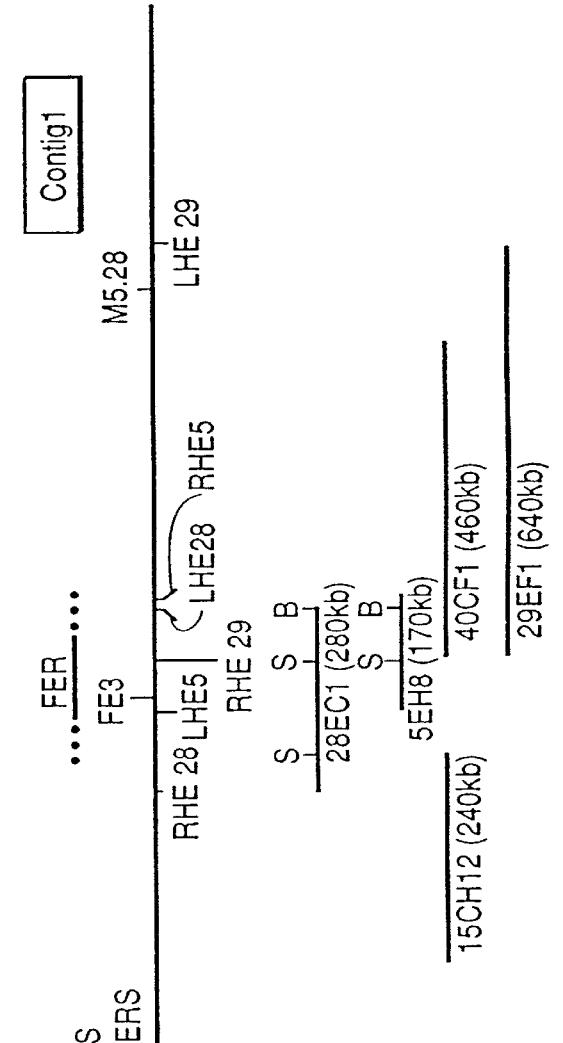
FIG. 1A
FIG. 1B-1

FIG. 2A

TB1 Amino Acid Sequence

```
VAPVVVGSGR APRHPAPAAM HPRRPDGFDG LGYRGGARDE QGFGGAFPAR SFSTGSDLGH    60
WVTTPPDIPG SRNLHWGEKS PPYGVPTTST PYEGPTEEPF SSGGGGSVQG QSSEQLNRFA   120
GFGIGLASLF TENVLAHPCI VLRRQCQVNY HAQHYHLTPF TVINIMYSFN KTQGPRALWK   180
GMGSTFIVQG VTLGAEGIIS EFTPLPREVL HKWSPKQIGE HLLLKSLTYV VAMPFYSASL   240
IETVQSEIIR DNTGILECVK EGIGRVIGMG VPHSKRLLPL LSLIFPTVLH GVLHYIISSV   300
IQKFVLLILK RKTYNSHLAE STSPVQSMLD AYFPELIANF AASLCSDVIL YPLETVLHRL   360
HIQGIRTIID NTDLGYEVLP INTQYEGMRD CINTIRQEEG VFGFYKGFGA VIIQYTLHAA   420
VLQITKIIYS TLLQ                                                    434
```

FIG. 2B

TB2 Amino Acid Sequence

```
ELRRFDRFLH EKNCHTDLLA KLEAKTGVNR SFIALGVIGL VALYLVFGYG ASLLCNLIGF    60
GYPAYISIKA IESPNKEDDT QWLTYWVYG  VFSIAEFFSD IFLSWFPFYY ILKCGFLLWC   120
MAPSPSNGAE LLYKRIIRPF FLKHESQMDS VVKDLKDKAK ETADAITKEA KKATVNLLGE   180
EKKST                                                               185
```

FIG. 3A

```
Met Ala Ala Ser Tyr Asp Gln Leu Leu Lys Gln Val Glu Ala Leu
 1               5                  10                  15

Lys Met Glu Asn Ser Asn Leu Arg Gln Glu Leu Glu Asp Asn Ser Asn
                20                  25                  30

His Leu Thr Lys Leu Glu Thr Glu Ala Ser Asn Met Lys Glu Val Leu
                35                  40                  45

Lys Gln Leu Gln Gly Ser Ile Glu Asp Glu Ala Met Ala Ser Ser Gly
                50                  55                  60

Gln Ile Asp Leu Leu Glu Arg Leu Lys Glu Leu Asn Leu Asp Ser Ser
 65                 70                  75                  80

Asn Phe Pro Gly Val Lys Leu Arg Ser Lys Met Ser Leu Arg Ser Tyr
                85                  90                  95

Gly Ser Arg Glu Gly Ser Val Ser Ser Arg Ser Gly Glu Cys Ser Pro
                100                 105                 110
```

FIG. 3B

Val Pro Met Gly Ser Phe Pro Arg Arg Gly Phe Val Asn Gly Ser Arg
115                      120                     125

Glu Ser Thr Gly Tyr Leu Glu Glu Leu Glu Lys Glu Arg Ser Leu Leu
130                      135                     140

Leu Ala Asp Leu Asp Lys Glu Glu Lys Lys Glu Lys Asp Trp Tyr Tyr Ala
145                      150                     155                 160

Gln Leu Gln Asn Leu Thr Lys Arg Ile Asp Ser Leu Pro Leu Thr Glu
                165                     170                     175

Asn Phe Ser Leu Gln Thr Asp Leu Thr Arg Arg Gln Leu Glu Tyr Glu
                180                     185                     190

Ala Arg Gln Ile Arg Val Ala Met Glu Glu Gln Leu Gly Thr Cys Gln
                195                     200                     205

Asp Met Glu Lys Arg Ala Gln Arg Arg Ile Ala Arg Ile Gln Gln Ile
210                      215                     220

FIG. 3C

```
Glu Lys Asp Ile Leu Arg Ile Arg Gln Leu Leu Gln Ser Gln Ala Thr
225                 230                 235                 240
Glu Ala Glu Arg Ser Ser Gln Asn Lys His Glu Thr Gly Ser His Asp
            245                 250                 255
Ala Glu Arg Gln Asn Glu Gly Gln Gly Val Gly Glu Ile Asn Met Ala
        260                 265                 270
Thr Ser Gly Asn Gly Gln Gly Ser Thr Thr Arg Met Asp His Glu Thr
    275                 280                 285
Ala Ser Val Leu Ser Ser Ser Ser Thr His Ser Ala Pro Arg Arg Leu
290                 295                 300
Thr Ser His Leu Gly Thr Lys Val Glu Met Val Tyr Ser Leu Leu Ser
305                 310                 315                 320
Met Leu Gly Thr His Asp Lys Asp Asp Met Ser Arg Thr Leu Leu Ala
            325                 330                 335
```

FIG. 3D

Met Ser Ser Ser Gln Asp Ser Cys Ile Ser Met Arg Gln Ser Gly Cys
                340                 345                 350

Leu Pro Leu Leu Ile Gln Leu Leu His Gly Asn Asp Lys Asp Ser Val
            355                 360                 365

Leu Leu Gly Asn Ser Arg Gly Ser Lys Glu Ala Arg Ala Arg Ala Ser
        370                 375                 380

Ala Ala Leu His Asn Ile Ile His Ser Gln Pro Asp Asp Lys Arg Gly
    385                 390                 395                 400

Arg Arg Glu Ile Arg Val Leu His Leu Glu Gln Ile Arg Ala Tyr
                405                 410                 415

Cys Glu Thr Cys Trp Glu Trp Gln Glu Ala His Glu Pro Gly Met Asp
            420                 425                 430

Gln Asp Lys Asn Pro Met Pro Ala Pro Val Glu His Gln Ile Cys Pro
        435                 440                 445

FIG. 3E

```
Ala Val Cys Val Leu Met Lys Leu Ser Phe Asp Glu Glu His Arg His
450                 455                 460
Ala Met Asn Glu Leu Gly Gly Leu Gln Ala Ile Ala Glu Leu Leu Gln
465                 470                 475                 480
Val Asp Cys Glu Met Tyr Gly Leu Thr Asn Asp His Tyr Ser Ile Thr
                    485                 490                 495
Leu Arg Arg Tyr Ala Gly Met Ala Leu Thr Asn Leu Thr Phe Gly Asp
                500                 505                 510
Val Ala Asn Lys Ala Thr Leu Cys Ser Met Lys Gly Cys Met Arg Ala
            515                 520                 525
Leu Val Ala Gln Leu Lys Ser Glu Ser Glu Asp Leu Gln Gln Val Ile
        530                 535                 540
Ala Ser Val Leu Arg Asn Leu Ser Trp Arg Ala Asp Val Asn Ser Lys
    545                 550                 555                 560
```

FIG. 3F

Lys Thr Leu Arg Glu Val Gly Ser Val Lys Ala Leu Met Glu Cys Ala
                565                 570                 575

Leu Glu Val Lys Lys Glu Ser Thr Leu Lys Ser Val Leu Ser Ala Leu
                580                 585                 590

Trp Asn Leu Ser Ala His Cys Thr Glu Asn Lys Ala Asp Ile Cys Ala
                595                 600                 605

Val Asp Gly Ala Leu Ala Phe Leu Val Gly Thr Leu Thr Tyr Arg Ser
                610                 615                 620

Gln Thr Asn Thr Leu Ala Ile Ile Glu Ser Gly Gly Gly Ile Leu Arg
                625                 630                 635                 640

Asn Val Ser Ser Leu Ile Ala Thr Asn Glu Asp His Arg Gln Ile Leu
                645                 650                 655

Arg Glu Asn Asn Cys Leu Gln Thr Leu Leu Gln His Leu Lys Ser His
                660                 665                 670

FIG. 3G

```
Ser Leu Thr Ile Val Ser Asn Ala Cys Gly Thr Leu Trp Asn Leu Ser
            675                 680                 685
Ala Arg Asn Pro Lys Asp Gln Glu Ala Leu Trp Asp Met Gly Ala Val
        690                 695                 700
Ser Met Leu Lys Asn Leu Ile His Ser Lys Met Ile Ala Met
    705                 710                 715         720
Gly Ser Ala Ala Leu Arg Asn Leu Met Ala Asn Arg Pro Ala Lys
725                 730                 735
Tyr Lys Asp Ala Asn Ile Met Ser Pro Gly Ser Ser Leu Pro Ser Leu
            740                 745                 750
His Val Arg Lys Gln Lys Ala Leu Glu Ala Leu Asp Ala Gln His
        755                 760                 765
Leu Ser Glu Thr Phe Asp Asn Ile Asp Asn Leu Ser Pro Lys Ala Ser
    770                 775                 780
```

FIG. 3H

His Arg Ser Lys Gln Arg His Lys Gln Ser Leu Tyr Gly Asp Tyr Val
785 790 795 800

Phe Asp Thr Asn Arg His Asp Asp Asn Arg Ser Asp Asn Phe Asn Thr
805 810 815

Gly Asn Met Thr Val Leu Ser Pro Tyr Leu Asn Thr Thr Val Leu Pro
820 825 830

Ser Ser Ser Ser Arg Gly Ser Leu Asp Ser Ser Arg Ser Glu Lys
835 840 845

Asp Arg Ser Leu Glu Arg Glu Arg Gly Ile Gly Leu Gly Asn Tyr His
850 855 860

Pro Ala Thr Glu Asn Pro Gly Thr Ser Ser Lys Arg Gly Leu Gln Ile
865 870 875 880

Ser Thr Thr Ala Ala Gln Ile Ala Lys Val Met Glu Glu Val Ser Ala
885 890 895

FIG. 3I

Ile His Thr Ser Gln Glu Asp Arg Ser Ser Gly Ser Thr Thr Glu Leu
                900                 905                 910

His Cys Val Thr Asp Glu Arg Asn Ala Leu Arg Arg Ser Ser Ala Ala
            915                 920                 925

His Thr His Ser Asn Thr Tyr Asn Phe Thr Lys Ser Glu Asn Ser Asn
        930                 935                 940

Arg Thr Cys Ser Met Pro Tyr Ala Lys Leu Glu Tyr Lys Arg Ser Ser
    945                 950                 955                 960

Asn Asp Ser Leu Asn Ser Val Ser Ser Asn Asp Gly Tyr Gly Lys Arg
            965                 970                 975

Gly Gln Met Lys Pro Ser Ile Glu Ser Tyr Ser Glu Asp Asp Glu Ser
        980                 985                 990

Lys Phe Cys Ser Tyr Gly Gln Tyr Pro Ala Asp Leu Ala His Lys Ile
    995                 1000                1005

FIG. 3J

His Ser Ala Asn His Met Asp Asn Asp Gly Glu Leu Asp Thr Pro
1010                          1015                          1020

Ile Asn Tyr Ser Leu Lys Tyr Ser Asp Glu Gln Leu Asn Ser Gly Arg
         1025                          1030                     1035                1040

Gln Ser Pro Ser Gln Asn Glu Arg Trp Ala Arg Pro Lys His Ile Ile
                1045                          1050                          1055

Glu Asp Glu Ile Lys Gln Ser Glu Gln Ser Arg Gln Ser Arg Asn Gln Ser
              1060                          1065                          1070

Thr Thr Tyr Pro Val Tyr Thr Glu Ser Thr Asp Asp Lys His Leu Lys
              1075                          1080                          1085

Phe Gln Pro His Phe Gly Gln Gln Glu Cys Val Ser Pro Tyr Arg Ser
              1090                          1095                          1100

Arg Gly Ala Asn Gly Ser Glu Thr Asn Arg Val Gly Ser Asn His Gly
              1105                          1110                          1115                1120

FIG. 3K

Ile Asn Gln Asn Val Ser Gln Ser Leu Cys Gln Glu Asp Asp Tyr Glu
1125                                      1130                              1135

Asp Asp Lys Pro Thr Asn Tyr Ser Glu Arg Tyr Ser Glu Glu Gln
1140                                      1145                    1150

His Glu Glu Glu Arg Pro Thr Asn Tyr Ser Ile Lys Tyr Asn Glu
1155                                      1160                    1165

Glu Lys Arg His Val Asp Gln Pro Ile Asp Tyr Ser Leu Lys Tyr Ala
1170                                      1175                              1180

Thr Asp Ile Pro Ser Ser Gln Lys Gln Ser Phe Ser Phe Ser Lys Ser
1185                                      1190                              1195  1200

Ser Ser Gly Gln Ser Ser Lys Thr Glu His Met Ser Ser Ser Ser Glu
1205                                      1210                              1215

Asn Thr Ser Thr Pro Ser Ser Asn Ala Lys Arg Gln Asn Gln Leu His
1220                                      1225                              1230

FIG. 3L

Pro Ser Ser Ala Gln Ser Arg Ser Gly Gln Pro Gln Lys Ala Ala Thr
1235                    1240                    1245

Cys Lys Val Ser Ser Ile Asn Gln Glu Thr Ile Gln Thr Tyr Cys Val
1250                    1255                    1260

Glu Asp Thr Pro Ile Cys Phe Ser Arg Cys Ser Ser Leu Ser Ser Leu
1265                    1270                    1275                1280

Ser Ser Ala Glu Asp Glu Ile Gly Cys Asn Gln Thr Thr Gln Glu Ala
                1285                    1290                    1295

Asp Ser Ala Asn Thr Leu Gln Ile Ala Glu Ile Lys Gly Lys Ile Gly
            1300                    1305                    1310

Thr Arg Ser Ala Glu Asp Pro Val Ser Glu Val Pro Ala Val Ser Gln
            1315                    1320                    1325

His Pro Arg Thr Lys Ser Ser Arg Leu Gln Gly Ser Ser Leu Ser Ser
            1330                    1335                    1340

FIG. 3M

Glu Ser Ala Arg His Lys Ala Val Glu Phe Pro Ser Gly Ala Lys Ser
1345                                   1355                1360

Pro Ser Lys Ser Gly Ala Gln Thr Pro Lys Ser Pro Pro Glu His Tyr
            1365                     1370                      1375

Val Gln Glu Thr Pro Leu Met Phe Ser Arg Cys Thr Ser Val Ser Ser
                1380                     1385                1390

Leu Asp Ser Phe Glu Ser Arg Ser Ile Ala Ser Ser Val Gln Ser Glu
            1395                     1400                     1405

Pro Cys Ser Gly Met Val Ser Gly Ile Ile Ser Pro Ser Asp Leu Pro
1410                                 1415                1420

Asp Ser Pro Gly Gln Thr Met Pro Pro Ser Arg Ser Lys Thr Pro Pro
1425                          1430                     1435                1440

Pro Pro Pro Gln Thr Ala Gln Thr Lys Arg Glu Val Pro Lys Asn Lys
            1445                     1450                          1455

FIG. 3N

Ala Pro Thr Ala Glu Lys Arg Glu Ser Gly Pro Lys Gln Ala Ala Val
1460                     1465                    1470

Asn Ala Ala Val Gln Arg Val Leu Pro Asp Ala Asp Thr Leu
1475                    1480                    1485

Leu His Phe Ala Thr Glu Ser Thr Pro Asp Gly Phe Ser Cys Ser Ser
1490                    1495                    1500

Ser Leu Ser Ala Leu Ser Leu Asp Glu Pro Phe Ile Gln Lys Asp Val
1505                    1510                    1515                    1520

Glu Leu Arg Ile Met Pro Pro Val Gln Glu Asn Asp Asn Gly Asn Glu
1525                    1530                    1535

Thr Glu Ser Glu Gln Pro Lys Glu Ser Asn Glu Asn Gln Glu Lys Glu
1540                    1545                    1550

Ala Glu Lys Thr Ile Asp Ser Glu Lys Asp Leu Leu Asp Asp Ser Asp
1555                    1560                    1565

FIG. 30

Asp Asp Ile Glu Ile Leu Glu Cys Ile Ile Ser Ala Met Pro
1570                1575                1580
Thr Lys Ser Ser Arg Lys Gly Lys Lys Pro Ala Gln Thr Ala Ser Lys
        1585                1590                1595                1600
Leu Pro Pro Val Ala Arg Lys Pro Ser Gln Leu Pro Val Tyr Lys
        1605                1610                1615
Leu Leu Pro Ser Gln Asn Arg Leu Gln Pro Gln Lys His Val Ser Phe
        1620                1625                1630
Thr Pro Gly Asp Asp Met Pro Arg Val Tyr Cys Val Glu Gly Thr Pro
        1635                1640                1645
Ile Asn Phe Ser Thr Ala Thr Ser Leu Ser Asp Leu Thr Ile Glu Ser
        1650                1655                1660
Pro Pro Asn Glu Leu Ala Ala Gly Glu Gly Val Arg Gly Gly Ala Gln
        1665                1670                1675                1680

FIG. 3P

Ser Gly Glu Phe Glu Lys Arg Asp Thr Ile Pro Thr Glu Gly Arg Ser
1685                1690                    1695

Thr Asp Glu Ala Gln Gly Gly Lys Thr Ser Ser Val Thr Ile Pro Glu
            1700                    1705                    1710

Leu Asp Asp Asn Lys Ala Glu Glu Gly Asp Ile Leu Ala Glu Cys Ile
        1715                    1720                    1725

Asn Ser Ala Met Pro Lys Gly Lys Ser His Lys Pro Phe Arg Val Lys
    1730                    1735                    1740

Lys Ile Met Asp Gln Val Gln Gln Ala Ser Ala Ser Ser Ser Ala Pro
1745                    1750                    1755            1760

Asn Lys Asn Gln Leu Asp Gly Lys Lys Lys Lys Pro Thr Ser Pro Val
        1765                    1770                    1775

Lys Pro Ile Pro Gln Asn Thr Glu Tyr Arg Thr Arg Val Arg Lys Asn
    1780                    1785                    1790

FIG. 3Q

Ala Asp Ser Lys Asn Asn Ala Glu Arg Val Phe Ser Asp Asn
    1795                          1800                          1805

Lys Asp Ser Lys Lys Gln Asn Leu Lys Asn Asn Ser Lys Asp Phe Asn
    1810                          1815                          1820

Asp Lys Leu Pro Asn Asn Glu Asp Arg Val Arg Gly Ser Phe Ala Phe
    1825                          1830                          1835           1840

Asp Ser Pro His His Tyr Thr Pro Ile Glu Gly Thr Pro Tyr Cys Phe
                    1845                          1850                          1855

Ser Arg Asn Asp Ser Leu Ser Ser Leu Asp Phe Asp Asp Asp Val
                  1860                          1865                        1870

Asp Leu Ser Arg Glu Lys Ala Glu Leu Arg Lys Ala Lys Glu Asn Lys
    1875                          1880                          1885

Glu Ser Glu Ala Lys Val Thr Ser His Thr Glu Leu Thr Ser Asn Gln
    1890                          1895                          1900

FIG. 3R

Gln Ser Ala Asn Lys Thr Gln Ala Ile Ala Lys Gln Pro Ile Asn Arg
1905                     1910                    1915                    1920

Gly Gln Pro Lys Pro Ile Leu Gln Lys Gln Ser Thr Phe Pro Gln Ser
1925                    1930                    1935

Ser Lys Asp Ile Pro Asp Arg Gly Ala Ala Thr Asp Glu Lys Leu Gln
1940                    1945                    1950

Asn Phe Ala Ile Glu Asn Thr Pro Val Cys Phe Ser His Asn Ser Ser
1955                    1960                    1965

Leu Ser Ser Leu Ser Asp Ile Asp Gln Glu Asn Asn Asn Lys Glu Asn
1970                    1975                    1980

Glu Pro Ile Lys Glu Thr Glu Pro Pro Asp Ser Gln Gly Glu Pro Ser
1985                    1990                    1995                    2000

Lys Pro Gln Ala Ser Gly Tyr Ala Pro Lys Ser Phe His Val Glu Asp
2005                    2010                    2015

FIG. 3S

Thr Pro Val Cys Phe Ser Arg Asn Ser Ser Leu Ser Ser Ile
2020                              2025                    2030

Asp Ser Glu Asp Asp Leu Leu Gln Glu Cys Ile Ser Ala Met Pro
     2035                    2040                         2045

Lys Lys Lys Pro Ser Arg Leu Lys Gly Asp Asn Glu Lys His Ser
2050                         2055                         2060

Pro Arg Asn Met Gly Gly Ile Leu Gly Glu Asp Leu Thr Leu Asp Leu
2065                              2070                    2075           2080

Lys Asp Ile Gln Arg Pro Asp Ser Glu His Gly Leu Ser Pro Asp Ser
                         2085                    2090                    2095

Glu Asn Phe Asp Trp Lys Ala Ile Gln Glu Gly Ala Asn Ser Ile Val
          2100                    2105                         2110

Ser Ser Leu His Gln Ala Ala Ala Ala Cys Leu Ser Arg Gln Ala
          2115                    2120                    2125

FIG. 3T

Ser Ser Asp Ser Asp Ser Ile Leu Ser Leu Lys Ser Gly Ile Ser Leu
2130                    2135                    2140

Gly Ser Pro Phe His Leu Thr Pro Asp Gln Glu Lys Pro Phe Thr
2145                    2150                    2155           2160

Ser Asn Lys Gly Pro Arg Ile Leu Lys Pro Gly Lys Ser Thr Leu
2165                    2170                    2175

Glu Thr Lys Lys Ile Glu Ser Glu Ser Lys Gly Ile Lys Gly Gly Lys
2180                    2185                    2190

Lys Val Tyr Lys Ser Leu Ile Thr Gly Lys Val Arg Ser Asn Ser Glu
2195                    2200                    2205

Ile Ser Gly Gln Met Lys Gln Pro Leu Gln Ala Asn Met Pro Ser Ile
2210                    2215                    2220

Ser Arg Gly Arg Thr Met Ile His Ile Pro Gly Val Arg Asn Ser Ser
2225                    2230                    2235           2240

FIG. 3U

```
Ser Ser Thr Ser Pro Val Ser Lys Lys Gly Pro Pro Leu Lys Thr Pro
            2245                2250                2255

Ala Ser Lys Ser Pro Ser Glu Gly Gln Thr Ala Thr Thr Ser Pro Arg
            2260                2265                2270

Gly Ala Lys Pro Ser Val Lys Ser Glu Leu Ser Pro Val Ala Arg Gln
            2275                2280                2285

Thr Ser Gln Ile Gly Gly Ser Ser Lys Ala Pro Ser Arg Ser Gly Ser
            2290                2295                2300

Arg Asp Ser Thr Pro Ser Arg Pro Ala Gln Gln Pro Leu Ser Arg Pro
            2305                2310                2315                2320

Ile Gln Ser Pro Gly Arg Asn Ser Ile Ser Pro Gly Arg Asn Gly Ile
            2325                2330                2335

Ser Pro Pro Asn Lys Leu Ser Gln Leu Pro Arg Thr Ser Ser Pro Ser
            2340                2345                2350
```

FIG. 3V

Thr Ala Ser Thr Lys Ser Ser Gly Ser Gly Lys Met Ser Tyr Thr Ser
       2355                2360                2365

Pro Gly Arg Gln Met Ser Gln Gln Asn Leu Thr Lys Gln Thr Gly Leu
       2370                2375                2380

Ser Lys Asn Ala Ser Ser Ile Pro Arg Ser Glu Ser Ala Ser Lys Gly
2385                2390                2395                2400

Leu Asn Gln Met Asn Asn Gly Ala Asn Lys Lys Val Glu Leu
                    2405                2410                2415

Ser Arg Met Ser Ser Thr Lys Ser Ser Gly Ser Glu Ser Asp Arg Ser
                2420                2425                2430

Glu Arg Pro Val Leu Val Arg Gln Ser Thr Phe Ile Lys Glu Ala Pro
       2435                2440                2445

Ser Pro Thr Leu Arg Arg Lys Leu Glu Glu Ser Ala Ser Phe Glu Ser
       2450                2455                2460

FIG. 3W

```
Leu Ser Pro Ser Ser Arg Pro Ala Ser Pro Thr Arg Ser Gln Ala Gln
2465                 2470                2475                2480

Thr Pro Val Leu Ser Pro Ser Leu Pro Asp Met Ser Leu Ser Thr His
            2485                2490                2495

Ser Ser Val Gln Ala Gly Gly Trp Arg Lys Leu Pro Pro Asn Leu Ser
                2500                2505                2510

Pro Thr Ile Glu Tyr Asn Asp Gly Arg Pro Ala Lys Arg His Asp Ile
        2515                2520                2525

Ala Arg Ser His Ser Glu Ser Pro Ser Arg Leu Pro Ile Asn Arg Ser
    2530                2535                2540

Gly Thr Trp Lys Arg Glu His Ser Lys His Ser Ser Ser Leu Pro Arg
2545                2550                2555                2560

Val Ser Thr Trp Arg Arg Thr Gly Ser Ser Ser Ser Ser Ile Leu Ser Ala
            2565                2570                2575
```

FIG. 3X

Ser Ser Glu Ser Ser Glu Lys Ala Lys Ser Glu Asp Glu Lys His Val
                2580                2585                2590

Asn Ser Ile Ser Gly Thr Lys Gln Ser Lys Glu Asn Gln Val Ser Ala
    2595                2600                2605

Lys Gly Thr Trp Arg Lys Ile Lys Glu Asn Glu Phe Ser Pro Thr Asn
            2610                2615                2620

Ser Thr Ser Gln Thr Val Ser Ser Gly Ala Thr Asn Gly Ala Glu Ser
    2625                2630                2635                2640

Lys Thr Leu Ile Tyr Gln Met Ala Pro Ala Val Ser Lys Thr Glu Asp
                2645                2650                2655

Val Trp Val Arg Ile Glu Asp Cys Pro Ile Asn Asn Pro Arg Ser Gly
            2660                2665                2670

Arg Ser Pro Thr Gly Asn Thr Pro Pro Val Ile Asp Ser Val Ser Glu
    2675                2680                2685

FIG. 3Y

Lys Ala Asn Pro Asn Ile Lys Asp Ser Lys Asp Asn Gln Ala Lys Gln
2690                              2695                          2700

Asn Val Gly Asn Gly Ser Val Pro Met Arg Thr Val Gly Leu Glu Asn
2705                              2710                          2715                          2720

Arg Leu Thr Ser Phe Ile Gln Val Asp Ala Pro Asp Gln Lys Gly Thr
                2725                              2730                          2735

Glu Ile Lys Pro Gly Gln Asn Asn Pro Val Pro Val Ser Glu Thr Asn
                2740                              2745                          2750

Glu Ser Pro Ile Val Glu Arg Thr Pro Phe Ser Ser Ser Ser Ser Ser
                2755                              2760                          2765

Lys His Ser Ser Pro Ser Gly Thr Val Ala Ala Arg Val Thr Pro Phe
2770                              2775                          2780

Asn Tyr Asn Pro Ser Pro Arg Lys Ser Ser Ala Asp Ser Thr Ser Ala
2785                              2790                          2795                          2800

FIG. 3Z

Arg Pro Ser Gln Ile Pro Thr Pro Val Asn Asn Thr Lys Lys Arg
2805                          2810              2815

Asp Ser Lys Thr Asp Ser Thr Glu Ser Ser Gly Thr Gln Ser Pro Lys
2820                         2825                  2830

Arg His Ser Gly Ser Tyr Leu Val Thr Ser Val
2835                        2840

FIG. 4A

```
APC   203  LGTCQDMEKRAQRRIARIQQIEKDILRIRQL  233
                 ::  ||  ||||||::|      |      |
RAL2  576  LTGAKGLQLRALRRIARIEQGGTAISPTSPL  606
```

FIG. 4B

```
APC       453  MKLSFDEEHRHAMNELGGLQAIAELLQVD  481
                  |  :   | |:||||  ::
M3 MAChR  249  LYWRIYKETEKRTKELAGLQASGTEAETE  277
               ||  :  |  :  |  |||||
MCC       220  LYPNLAEERSRWEKELAGLREENESLTAM  248
                  ::  ||:||  ::||
APC       453  MKLSFDEEHRHAMNELGGLQAIAELLQVD  481
```

FIG. 6A

```
GCA GTC GCC GCT CCA GTC TAT CCG GCA CTA GGA ACA GCC CCG GGN GGC GAG ACG          55
Ala Val Ala Ala Pro Val Tyr Pro Ala Leu Gly Thr Ala Pro Gly Gly Glu Thr         109

GTC CCC GCC ATG TCT GCG GCC ATG TCT GCG GAG AGG TTC GAC CGG TTC CTG CAC GAG
Val Pro Ala MET Ser Ala Ala MET Ser Ala Glu Arg Phe Asp Arg Phe Leu His Glu    163

AAG AAC TGC ATG ACT GAC CTT CTG GCC AAG CTC GAG GCC AAA ACC GGC GTG AAC
Lys Asn Cys MET Thr Asp Leu Leu Ala Lys Leu Glu Ala Lys Thr Gly Val Asn         217

AGG AGC TTC ATC GCT CTT GGT GTC CTT GGA CTG ATA GCC TTG TAC TAC CTG GTG TTC
Arg Ser Phe Ile Ala Leu Gly Val Leu Gly Leu Ile Ala Leu Tyr Tyr Leu Val Phe    271

GGT TAT GGA GCC TCT CTC CTC TGC CTG ATA GGA TTT GGC TAC CCA GCC TAC
Gly Tyr Gly Ala Ser Leu Leu Cys Leu Ile Gly Phe Gly Tyr Pro Ala Tyr            325

ATC TCA ATT AAA GCT ATA GAG AGT CCC AAC AAA GAA ATT GCT GAA TTC TTC TCT GAT ATC
Ile Ser Ile Lys Ala Ile Glu Ser Pro Asn Lys Glu Ile Ala Glu Phe Phe Ser Asp Ile 379

ACC TAC TGG GTA GTG TAT GGT TTG TTC TAC ATG CTG AAG TGT GGC CTG TGG
Thr Tyr Trp Val Val Tyr Gly Leu Phe Tyr MET Leu Lys Cys Gly Leu Trp           433

TTC CTG TCA TGG TGG TTC TAC CCC TTC TAC TAC TAC ATG CTG AAG TGT GGC CTG TGG
Phe Leu Ser Trp Trp Phe Tyr Pro Phe Tyr Tyr MET Leu Lys Cys Gly Leu Trp       487

TGC ATG GCC CCG AGC CCT TCT AAT GGG GCT GAA CTG CTC TAC AAG CGC ATC
Cys MET Ala Pro Ser Pro Ser Asn Gly Ala Glu Leu Leu Tyr Lys Arg Ile            541

CGT CCT TTC TTC CTG AAG CAC GAG TCC CAG ATG GAC AGT GTG AAG GAC CTT
Arg Pro Phe Phe Leu Lys His Glu Ser Gln MET Asp Ser Val Val Lys Asp Leu
```

FIG. 6B

```
                                                    568                                                                595'
AAA GAC AAG TCC AAA GAG ACT GCA GAT GCC ATC ACT AAA GAA GCG AAG AAA GCT
Lys Asp Lys Ser Lys Glu Thr Ala Asp Ala Ile Thr Lys Glu Ala Lys Lys Ala
                                                    622
ACC GTG AAT TTA CTG GGT GAA GAA AAG AGC ACC TAA ACC AGA
Thr Val Asn Leu Leu Gly Glu Glu Lys Ser Thr
                   640                650                660                670                680                690                700
CTAAACCAGA CTGGATGGAA ACTTCCTGCC CTCTCTGTAC CTTCCTACTG GAGCTTGATG TTATATTAGG
                   710                720                730                740                750                760                770
GACTGTGGTA TAATTATTTT AATAAATGTTG CCTTGGAAAC ATTTTTGAGA TATTAAAGAT TGGAATGTGT
                   780                790                800                810                820                830                840
TGTAAGTTTC TTTGCTTACT TTTACTGTCT ATATATATAG GGAGCACTTT AAACTTAAATG CAGTGGGCAG
                   850                860                870                880                890                900                910
TGTCCACGTT TTTGGAAAAT GTATTTTGCC TCTGGGTAGG AAAAGATGTA TGTTGCTATC CTGCAGGAAA
                   920                930                940                950                960                970                980
TATAAACTTA AAATAAAATT ATATACCCCA CAGGCTGTGT ACTTTACTGG GCTCTCCCTG CACGSATTTT
                   990                1000               1010               1020               1030               1040               1050
CTCTGTAGTT ACATTTAGGR TAATCTTTAT GGTTCTACTT CCTRTAATGT ACAATTTTAT ATAATTCNGR
                   1060               1070               1080               1090               1100               1110               1120
AATGTTTTA ATGTATTTGT GCACATGTAC ATATGGAAAT GTTACTGTCT GACTACANCA TGCATCATGC
                   1130               1140               1150               1160               1170               1180               1190
TCATGGGGAG GGAGCAGGGG AAGGTTGTAT GTGTCATTTA TAACTTCTGT ACAGTAAGAC CACCTGCCAA
                   1200               1210               1220               1230               1240               1250               1260
AAGCTGGAGG AACCATTGTG CTGGTGTGGT CTACTAAATA ATACTTTAGG AAATACGTGA TTAATATGCA
                   1270               1280               1290               1300               1310               1320               1330
AGTGAACAAA GTGAGAAATG AAATCGAATG GAGATTGGCC TGGTTGTTTC CGTAGTATAT GGCATATGAA
                   1340               1350               1360               1370               1380               1390               1400
```

FIG. 6C

```
TACCAGGATA GCTTTATAAA GCAGTTAGTT AGTTAGTTAC TCACTCTAGT GATAAATCGG GAAATTTACA
    1410       1420       1430       1440       1450       1460       1470
CACACACACA CACACACACA CACACACACA CACACACACA CACACACACA GAGTACCCTG TAACTCTCAA
    1480       1490       1500       1510       1520       1530       1540
TTCCCTGAAA AACTAGTAAT ACTGTCTTAT CTGCTATAAA CTTTACATAT TTGTCTATTG TCAAGATGCT
    1550       1560       1570       1580       1590       1600       1610
ACANTGGAMN CCATTTCTGG TTTTATCTTC ANAGSGGAGA NACATGTTGA TTTAGTCTTC TTTCCCAATC
    1620       1630       1640       1650       1660       1670       1680
TTCTTTTTA AMCCAGTTTN AGGMNCTTCT GRAGATTTGY CCACCTCTGA TTACATGTAT GTTCTYGTTT
    1690       1700       1710       1720       1730       1740       1750
GTATCATKAG CAACAACATG CTAATGRCGA CACCTAGCTC TRAGMGCAAT TCTGGGAGAN TGARAGGNWG
    1760       1770       1780       1790       1800       1810       1820
TATARAGTMN CCCATAATCT GCTTGGCAAT AGTTAAGTCA ATCTATCTTC AGTTTTCTC TGGCCTTTAA
    1830       1840       1850       1860       1870       1880       1890
GGTCAAACAC AAGAGGCTTC CCTAGTTTAC AAGTCAGAGT CACTTGTAGT CCATTAAAT GCCCTCATCC
    1900       1910       1920       1930       1940       1950       1960
GTATTCTTTG TGTTGATAAG CTGCACAKGA CTACATAGTA AGTACAGANC AGTAAAGTTA ANNCGGATGT
    1970       1980       1990       2000       2010       2020       2030
CTCCATTGAT CTGCCAANTC GNTATAGAGA GCAATTTGTC TGGACTAGAA AATCTGAGTT TTACACCATA
    2040       2050       2060       2070       2080       2090       2100
CTGTTAAGAG TCCTTTTGAA TTAAACTAGA CTAAAACAAG TGTATAACTA AACTAACAAG ATTAAATATC
    2110       2120       2130       2140       2150       2160       2170
CAGCCAGTAC AGTATTTTTT AAGGCAAATA GCTCACCTTG AGNTAACAAT CAGGTAAGAT
    2180       2190       2200       2210       2220       2230       2240
CATNACAATG TCTCATGATG TNAANAATAT TAAAGATATC AATACTAAGT GACAGTATCA CNNCTAATAT
```

FIG. 6D

```
         2250       2260       2270       2280       2290       2300       2310
AATATGGATC AGAGCATTTA TTTTGGGGAG GAAAAACAGTG GTGATTACCG GCATTTTATT AAACTTAAAA
         2320       2330       2340       2350       2360       2370       2380
CTTTGTAGAA AGCAAACAAA ATTGTTCTTG GGAGAAAATC AACTTTTAGA TTAAAAAAAT TTTAAGTAWC
         2390       2400       2410       2420       2430       2440       2450
TAGGAGTATT TAAATCCTTT TCCCATAAAT AAAAGTACAG TTTTCTTGGT GGCAGAATGA AAATCAGCAA
         2460       2470       2480       2490       2500       2510       2520
CNTCTAGCAT ATAGACTATA TAATCAGATT GACAGCATAT AGAATATATT ATCAGACAAG ATGAGGAGGT
         2530       2540       2550       2560       2570       2580       2590
ACAAAAGTTA CTATTGCTCA TAATGACTTA CAGGCTAAAA NTAGNTNTAA AATACTATAT TAAATTCTGA
         2600       2610       2620       2630       2640       2650       2660
ATGCAATTTT TTTTGTTTCC CTTGAGACCA AAATTTAAGT TAACTGTTGC TGGCAGTCTA AGTGTAAATG
         2670       2680       2690       2700       2710       2720       2730
TTAACAGCAG GAGAAGTTAA GAATTGAGCA GTTCTGTTGC ATGATTTCCC AAATGAAATA CTGCCTTGGC
         2740       2750       2760       2770       2780       2790       2800
TAGAGTTTGA AAAACTAATT GAGCCTGTGC CTGGCTAGAA AACAAGCGTT TATTTGAATG TGAATAGTGT
         2810       2820       2830       2840       2850       2860       2870
TTCAAAGGTA TGTAGTTACA GAATTCCTAC CAAACAGCTT AAATTCTTCA AGAAAGAATT CCTGCAGCAG
         2880       2890       2900       2910       2920       2930       2940
TTATTCCCTT ACCTGAAGGC TTCAATCATT TGGATCAACA ACTGCTACTC TCGGGAAGAC TCCTCTACTC
         2950       2960       2970       2980       2990       3000       3010
ACAGCTGAAG AAAATGAGCA CACCCTTCAC ACTGTTATCA CCTATCCTGA AGATGTGATA CACTGAATGG
         3020       3030       3040       3050       3060       3070       3080
AAATAAATAG ATGTAAATAA AATTGAGWTC TCATTTAAAA AAAACCATGT GCCCAATGGG AAAATGACCT
         3090       3100       3110       3120       3130       3140       3150
CATGTTGTGG TTTAAACAGC AACTGCACCC ACTAGCACAG CCCATTGAGC TANCCTATAT ATACATCTCT
         3160
GTCAGTGCCC CTC
```

FIG. 7A

```
GGA CTC GGA AAT GAG GTC CAA GGG TAG CCA AGG ATG GCT GCA TCA TAT GAT         54
Gly Leu Gly Asn Glu Val Gln Gly  .  Pro Arg MET Ala Ala Ser Tyr Asp

CAG TTG TTA AAG CAA GTT GAG GCA CTG AAG ATG GAG AAC TCA AAT CTT CGA CAA    108
Gln Leu Leu Lys Gln Val Glu Ala Leu Lys MET Glu Asn Ser Asn Leu Arg Gln

GAG CTA GAA GAT AAT TCC AAT CAT CTT ACA AAA CTG GAA GCA TCT AAT            162
Glu Leu Glu Asp Asn Ser Asn His Leu Thr Lys Leu Glu Ala Ser Asn

ATG AAG GAA GTA CTT AAA CAA CTA CAA GGA AGT ATT GAA GAT GAA GCT ATG GCT    216
MET Lys Glu Val Leu Lys Gln Leu Gln Gly Ser Ile Glu Asp Glu Ala MET Ala

TCT TCT GGA CAG ATT GAT TTA GAG CGT CTT AAA GAG CTT AAC TTA GAT AGC        270
Ser Ser Gly Gln Ile Asp Leu Glu Arg Leu Lys Glu Leu Asn Leu Asp Ser

AGT AAT TTC CCT GGA GTA AAA CTG CGG TCA AAA ATG TCC CTC CGT TCT TAT GGA    324
Ser Asn Phe Pro Gly Val Lys Leu Arg Ser Lys MET Ser Leu Arg Ser Tyr Gly
```

FIG. 7B

```
AGT AAT TTC CCT GGA GTA AAA CTG CGG TCA AAA ATG TCC CTC CGT TCT TAT GGA
Ser Asn Phe Pro Gly Val Lys Leu Arg Ser Lys MET Ser Leu Arg Ser Tyr Gly
                    297                                              324

AGC CGG GAA GGA TCT GTA TCA AGC CGT TCT GGA GAG TGC AGT CCT GTT CCT ATG
Ser Arg Glu Gly Ser Val Ser Ser Arg Ser Gly Glu Cys Ser Pro Val Pro MET
                    351                                              378

GGT TCA TTT CCA AGA AGA GGG TTT GTA AAT GGA AGC AGA GAA AGT ACT GGA TAT
Gly Ser Phe Pro Arg Arg Gly Phe Val Asn Gly Ser Arg Glu Ser Thr Gly Tyr
                    405                                              432

TTA GAA GAA CTT GAG AAA GAG AGG TCA TTG CTT CTT GCT GAT CTT GAC AAA GAA
Leu Glu Glu Leu Glu Lys Glu Arg Ser Leu Leu Leu Ala Asp Leu Asp Lys Glu
                    459                                              486

GAA AAG GAA AAA GAC TGG TAT TAC GCT CAA CTT CAG AAT CTC ACT AAA AGA ATA
Glu Lys Glu Lys Asp Trp Tyr Tyr Ala Gln Leu Gln Asn Leu Thr Lys Arg Ile
                    513                                              540

```
GAT AGT CTT CCT TTA ACT GAA AAT TTT TCC TTA CAA ACA GAT TTG ACC AGA AGG
Asp Ser Leu Pro Leu Thr Glu Asn Phe Ser Leu Gln Thr Asp Leu Thr Arg Arg
                                                                      648
CAA TTG GAA TAT GAA GCA AGG CAA ATC AGA GTT GCG ATG GAA CAA CTA GGT
Gln Leu Glu Tyr Glu Ala Arg Gln Ile Arg Val Ala MET Glu Gln Leu Gly
                                                                  702
ACC TGC CAG GAT ATG GAA AAA CGA CAG CGA AGA ATA GCC AGA ATT CAG CAA
Thr Cys Gln Asp MET Glu Lys Arg Gln Arg Arg Ile Ala Arg Ile Gln Gln
                                                                  756
ATC GAA AAG GAC ATA CTT CGT ATA CGA CAG CTT TTA CAG TCC CAA GCA ACA GAA
Ile Glu Lys Asp Ile Leu Arg Ile Arg Gln Leu Leu Gln Ser Gln Ala Thr Glu
                                                                      810
GCA GAG AGG TCA TCT CAG AAC AAG CAT GAA ACC GGC TCA CAT GAT GCT GAG CGG
Ala Glu Arg Ser Ser Gln Asn Lys His Glu Thr Gly Ser His Asp Ala Glu Arg
                                                                      864
CAG AAT GAA GGT CAA GGA GTG GGA GAA ATC AAC ATG GCA ACT TCT GGT AAT GGT
Gln Asn Glu Gly Gln Gly Val Gly Glu Ile Asn MET Ala Thr Ser Gly Asn Gly
```

FIG. 7D

```
CAG GGT TCA ACT ACA CGA ATG GAC CAT GAA ACA GCC AGT GTT TTG AGT TCT AGT    918
Gln Gly Ser Thr Thr Arg MET Asp His Glu Thr Ala Ser Val Leu Ser Ser Ser

891
AGC ACA CAC TCT GCA CCT CGA AGG CTG ACA AGT CAT CTG GGA ACC AAG GTG GAA    972
Ser Thr His Ser Ala Pro Arg Arg Leu Thr Ser His Leu Gly Thr Lys Val Glu

945
ATG GTG TAT TCA TTG TTG TCA ATG CTT GGT ACT CAT GAT AAG GAT GAT ATG TCG   1026
MET Val Tyr Ser Leu Leu Ser MET Leu Gly Thr His Asp Lys Asp Asp MET Ser

999
CGA ACT TTG CTA GCT ATG TCT AGC TCC CAA GAC AGC TGT ATA TCC ATG CGA CAG   1080
Arg Thr Leu Leu Ala MET Ser Ser Ser Gln Asp Ser Cys Ile Ser MET Arg Gln

1053
TCT GGA TGT CTT CCT CTC CTC ATC CAG CTT TTA CAT GGC AAT GAC AAA GAC TCT   1134
Ser Gly Cys Leu Pro Leu Leu Ile Gln Leu Leu His Gly Asn Asp Lys Asp Ser

1107
GTA TTG TTG GGA AAT TCC CGG GGC AGT AAA GAG GCT CGG GCC AGG GCC AGT GCA   1188
                                                                          1161
```

FIG. 7E

```
Val Leu Gly Asn Ser Arg Gly Ser Lys Glu Ala Arg Ala Arg Ala Ser Ala
                                                                      1215                                              1242
GCA CTC CAC AAC ATC ATT CAC TCA CAG CCT GAT GAC AAG AGA GGC AGG CGT GAA
Ala Leu His Asn Ile Ile His Ser Gln Pro Asp Asp Lys Arg Gly Arg Arg Glu
                                  1269                                              1296
ATC CGA GTC CTT CAT CTT TTG GAA CAG ATA CGC GCT TAC TGT GAA ACC TGT TGG
Ile Arg Val Leu His Leu Leu Glu Gln Ile Arg Ala Tyr Cys Glu Thr Cys Trp
                                  1323                                              1350
GAG TGG CAG GAA GCT CAT GAA CCA GAA GGC ATG GAC AAA AAT CCA ATG CCA
Glu Trp Gln Glu Ala His Glu Pro Gly MET Asp Lys Asn Pro MET Pro
                                  1377                                              1404
GCT CCT GTT GAA CAT CAG ATC TGT CCT GCT GTG TGT GTT CTA ATG AAA CTT TCA
Ala Pro Val Glu His Gln Ile Cys Pro Ala Val Cys Val Leu MET Lys Leu Ser
                                  1431                                              1458
TTT GAT GAA GAG CAT AGA CAT GCA ATG AAT GAA CTA GGG GGA CTA CAG GCC ATT
Phe Asp Glu Glu His Arg His Ala MET Asn Glu Leu Gly Gly Leu Gln Ala Ile
```

FIG. 7F

```
        1485                                                               1512
GCA GAA TTA TTG CAA GTG GAC TGT GAA ATG TAT GGG CTT ACT AAT GAC CAC TAC
Ala Glu Leu Leu Gln Val Asp Cys Glu MET Tyr Gly Leu Thr Asn Asp His Tyr 1539                                                               1566
AGT ATT ACA CTA AGA CGA TAT GCT GGA ATG GCT TTG ACA AAC TTG ACT TTT GGA
Ser Ile Thr Leu Arg Arg Tyr Ala Gly MET Ala Leu Thr Asn Leu Thr Phe Gly 1593                                                               1620
GAT GTA GCC AAC AAG GCT ACG CTA TCT ATG AAA GGC TGC ATG AGA GCA CTT
Asp Val Ala Asn Lys Ala Thr Leu Cys Ser MET Lys Gly Cys MET Arg Ala Leu 1647                                                               1674
GTG GCC CAA CTA AAA TCT GAA AGT GAA GAC TTA CAG CAG GTT ATT GCA AGT GTT
Val Ala Gln Leu Lys Ser Glu Ser Glu Asp Leu Gln Gln Val Ile Ala Ser Val 1701                                                               1728
TTG AGG AAT TTG TCT TGG CGA GCA GAT GTA AAT AGT AAA AAG ACG TTG CGA GAA
Leu Arg Asn Leu Ser Trp Arg Ala Asp Val Asn Ser Lys Lys Thr Leu Arg Glu 1755                                                               1782
GTT GGA AGT GTG AAA GCA TTG ATG GAA TGT GCT TTA GAA GTT AAA AAG GAA TCA
Val Gly Ser Val Lys Ala Leu MET Glu Cys Ala Leu Glu Val Lys Lys Glu Ser
```

FIG. 7G

```
ACC CTC AAA AGC GTA TTG AGT GCC TTA TGG AAT TTG TCA GCA CAT TGC ACT GAG
Thr Leu Lys Ser Val Leu Ser Ala Leu Trp Asn Leu Ser Ala His Cys Thr Glu
                                                1809                            1836

AAT AAA GCT GAT ATA TGT GCT GTA GAT GGT GCA CTT GCA TTT TTG GTT GGC ACT
Asn Lys Ala Asp Ile Cys Ala Val Asp Gly Ala Leu Ala Phe Leu Val Gly Thr
                        1863                                        1890

CTT ACT TAC CGG AGC CAG ACA AAC ACT TTA GCC ATT TTA ATT ATT GAA AGT GGA GGT GGG
Leu Thr Tyr Arg Ser Gln Thr Asn Thr Leu Ala Ile Ile Ile Glu Ser Gly Gly Gly
                                    1917                                    1944

ATA TTA CGG AAT GTG TCC AGC TTG ATA GCT ACA AAT GAG GAC CAC AGG CAA ATC
Ile Leu Arg Asn Val Ser Ser Leu Ile Ala Thr Asn Glu Asp His Arg Gln Ile
                                    1971                                        1998

CTA AGA GAG AAC AAC TGT CTA CAA ACT TTA TTA CAA CAC TTA AAA TCT CAT AGT
Leu Arg Glu Asn Asn Cys Leu Gln Thr Leu Leu Gln His Leu Lys Ser His Ser
                                    2025                                        2052

TTG ACA ATA GTC AGT AAT GCA TGT GGA ACT TTG TGG AAT CTC TCA GCA AGA AAT
Leu Thr Ile Val Ser Asn Ala Cys Gly Thr Leu Trp Asn Leu Ser Ala Arg Asn
                            2079                                        2106
```

FIG. 7H

```
CCT AAA GAC CAG GAA GCA TTA TGG GAC ATG GGG GCA GTT AGC ATG CTC AAG AAC    2160
Pro Lys Asp Gln Glu Ala Leu Trp Asp MET Gly Ala Val Ser MET Leu Lys Asn

CTC ATT CAT TCA AAG CAC AAA ATG ATT GCT ATG GGA AGT GCT GCA GCT TTA AGG    2214
Leu Ile His Ser Lys His Lys MET Ile Ala MET Gly Ser Ala Ala Ala Leu Arg

AAT CTC ATG GCA AAT AGG CCT GCG AAG TAC AAG GAT GCC AAT ATT ATG TCT CCT    2268
Asn Leu MET Ala Asn Arg Pro Ala Lys Tyr Lys Asp Ala Asn Ile MET Ser Pro

GGC TCA AGC TTG CCA TCT CTT CAT GTT AGG AAA CAA AAA GCC CTA GAA GCA GAA    2322
Gly Ser Ser Leu Pro Ser Leu His Val Arg Lys Gln Lys Ala Leu Glu Ala Glu

TTA GAT GCT CAG CAC TTA TCA GAA ACT TTT GAC AAT ATA GAC AAT TTA AGT CCC    2376
Leu Asp Ala Gln His Leu Ser Glu Thr Phe Asp Asn Ile Asp Asn Leu Ser Pro
```

FIG. 71

```
     2403                                                      2430
AAG GCA TCT CAT CGT AGT AAG CAG AGA CAC AAG CAA AGT CTC TAT GGT GAT TAT
Lys Ala Ser His Arg Ser Lys Gln Arg His Lys Gln Ser Leu Tyr Gly Asp Tyr 2457                                                      2484
GTT TTT GAC ACC AAT CGA CAT GAT AAT AGG TCA GAC AAT TTT AAT ACT GGC
Val Phe Asp Thr Asn Arg His Asp Asn Arg Ser Asp Asn Phe Asn Thr Gly 2511                                                      2538
AAC ATG ACT GTC CTT TCA CCA TAT TTG AAT ACT ACA GTG TTA CCC AGC TCC TCT
Asn MET Thr Val Leu Ser Pro Tyr Leu Asn Thr Thr Val Leu Pro Ser Ser Ser 2565                                                      2592
TCA TCA AGA GGA AGC TTA GAT AGT TCT CGT TCT GAA AAA GAT AGA AGT TTG GAG
Ser Ser Arg Gly Ser Leu Asp Ser Ser Arg Ser Glu Lys Asp Arg Ser Leu Glu 2619                                                      2646
AGA GAA CGC GGA ATT GGT CTA GGC AAC TAC CAT CCA GCA ACA GAA AAT CCA GGA
Arg Glu Arg Gly Ile Gly Leu Gly Asn Tyr His Pro Ala Thr Glu Asn Pro Gly 2673                                                      2700
ACT TCT TCA AAG CGA GGT TTG CAG ATC TCC ACC ACT GCA GCC CAG ATT GCC AAA
Thr Ser Ser Lys Arg Gly Leu Gln Ile Ser Thr Thr Ala Ala Gln Ile Ala Lys
```

FIG. 7J

```
        GTC ATG GAA GAA GTG TCA GCC ATT CAT ACC TCT CAG GAA GAC AGA AGT TCT GGG
        Val MET Glu Glu Val Ser Ala Ile His Thr Ser Gln Glu Asp Arg Ser Ser Gly
2727                                                                              2754

TCT ACC ACT GAA TTA CAT TGT GTG ACA GAT GAG AGA AAT GCA CTT AGA AGA AGC
        Ser Thr Thr Glu Leu His Cys Val Thr Asp Glu Arg Asn Ala Leu Arg Arg Ser
2781                                                                              2808

TCT GCT GCC CAT ACA CAT TCA AAC ACT TAC AAT TTC ACT AAG TCG GAA AAT TCA
        Ser Ala Ala His Thr His Ser Asn Thr Tyr Asn Phe Thr Lys Ser Glu Asn Ser
2835                                                                              2862

AAT AGG ACA TGT TCT ATG CCT TAT GCC AAA TTA GAA TAC AAG AGA TCT TCA AAT
        Asn Arg Thr Cys Ser MET Pro Tyr Ala Lys Leu Glu Tyr Lys Arg Ser Ser Asn
2889                                                                              2916

GAT AGT TTA AAT AGT GTC AGT AGT AAT GAT GGT TAT GGT AAA AGA GGT CAA ATG
        Asp Ser Leu Asn Ser Val Ser Ser Asn Asp Gly Tyr Gly Lys Arg Gly Gln MET
2943                                                                              2970
```

FIG. 7K

```
                                                                    3024
AAA CCC TCG ATT GAA TAT TCT GAA GAT GAT GAA AGT AAG TTT TGC AGT TAT
Lys Pro Ser Ile Glu Tyr Ser Glu Asp Asp Glu Ser Lys Phe Cys Ser Tyr
                                                                    3078
GGT CAA TAC CCA GCC GAC CTA GCC CAT AAA ATA CAT AGT GCA AAT CAT ATG GAT
Gly Gln Tyr Pro Ala Asp Leu Ala His Lys Ile His Ser Ala Asn His MET Asp
                                                                    3132
GAT AAT GAT GGA GAA CTA GAT ACA CCA ATA AAT TAT AGT CTT AAA TAT TCA GAT
Asp Asn Asp Gly Glu Leu Asp Thr Pro Ile Asn Tyr Ser Leu Lys Tyr Ser Asp
                                                                    3186
GAG CAG TTG AAC TCT GGA AGG CAA AGT CCT TCA CAG AAT GAA AGA TGG GCA AGA
Glu Gln Leu Asn Ser Gly Arg Gln Ser Pro Ser Gln Asn Glu Arg Trp Ala Arg
                                                                    3240
CCC AAA CAC ATA ATA GAA GAT ATA AAA CAA AGT GAG CAA AGA CAA TCA AGG
Pro Lys His Ile Ile Glu Asp Ile Lys Gln Ser Glu Gln Arg Gln Ser Arg
                                                                    3294
AAT CAA AGT ACA ACT TAT CCT GTT TAT ACT GAG AGC ACT GAT GAT AAA CAC CTC
Asn Gln Ser Thr Thr Tyr Pro Val Tyr Thr Glu Ser Thr Asp Asp Lys His Leu
```

FIG. 7L

```
                                                                3348
AAG TTC CAA CCA CAT TTT GGA CAG CAG GAA TGT GTT TCT CCA TAC AGG TCA CGG
Lys Phe Gln Pro His Phe Gly Gln Gln Glu Cys Val Ser Pro Tyr Arg Ser Arg

3402
GGA GCC AAT GGT TCA GAA ACA AAT CGA GTG GGT TCT AAT CAT GGA ATT AAT CAA
Gly Ala Asn Gly Ser Glu Thr Asn Arg Val Gly Ser Asn His Gly Ile Asn Gln

3456
AAT GTA AGC CAG TCT TTG TGT CAA GAA GAT TAT GAA GAT GAT AAG CCT ACC
Asn Val Ser Gln Ser Leu Cys Gln Glu Asp Tyr Glu Asp Asp Lys Pro Thr

3510
AAT TAT AGT GAA CGT TAC TCT GAA GAA GAA CAG CAT GAA GAA GAA AGA CCA
Asn Tyr Ser Glu Arg Tyr Ser Glu Glu Glu Gln His Glu Glu Glu Arg Pro

3564
ACA AAT TAT AGC ATA AAA TAT GAA GAG AAA CGT CAT GTG GAT CAG CCT ATT
Thr Asn Tyr Ser Ile Lys Tyr Asn Glu Lys Arg His Val Asp Gln Pro Ile 3618
3591
```

FIG. 7M

```
GAT TAT AGT TTA AAA TAT GCC ACA GAT ATT CCT TCA TCA CAG AAA CAG TCA TTT
Asp Tyr Ser Leu Lys Tyr Ala Thr Asp Ile Pro Ser Ser Gln Lys Gln Ser Phe
                                                                      3672
TCA TTC TCA AAG AGT TCA TCT GGA CAA AGC AGT AAA ACC GAA CAT ATG TCT TCA
Ser Phe Ser Lys Ser Ser Ser Gly Gln Ser Ser Lys Thr Glu His MET Ser Ser
                                                                      3726
AGC AGT GAG AAT ACG TCC ACA CCT TCA TCT AAT GCC AAG AGG CAG AAT CAG CTC
Ser Ser Glu Asn Thr Ser Thr Pro Ser Ser Asn Ala Lys Arg Gln Asn Gln Leu
                                                                      3780
CAT CCA AGT TCT GCA CAG AGT GGT CAG CCT CAA AAG GCT GCC ACT TGC
His Pro Ser Ser Ala Gln Ser Gly Gln Pro Gln Lys Ala Ala Thr Cys
                                                                      3834
AAA GTT TCT TCT ATT AAC CAA GAA ACA ATA CAG ACT TAT TGT GTA GAA GAT ACT
Lys Val Ser Ser Ile Asn Gln Glu Thr Ile Gln Thr Tyr Cys Val Glu Asp Thr
                                                                      3888
CCA ATA TGT TTT TCA AGA TGT AGT TCA TTA TCA TCT TTG TCA TCA GCT GAA GAT
Pro Ile Cys Phe Ser Arg Cys Ser Ser Leu Ser Ser Leu Ser Ser Ala Glu Asp
```

FIG. 7N

```
                3915                                                    3942
GAA ATA GGA TGT AAT CAG ACG ACA CAG GAA GCA GAT TCT GCT AAT ACC CTG CAA
Glu Ile Gly Cys Asn Gln Thr Thr Gln Glu Ala Asp Ser Ala Asn Thr Leu Gln 3969                                                    3996
ATA GCA GAA ATA AAA GGA AAG ATT GGA ACT AGG TCA GCT GAA GAT CCT GTG AGC
Ile Ala Glu Ile Lys Gly Lys Ile Gly Thr Arg Ser Ala Glu Asp Pro Val Ser 4023                                                    4050
GAA GTT CCA GCA GTG TCA CAG CAC CCT AGA ACC AAA TCC AGC AGA CTG CAG GGT
Glu Val Pro Ala Val Ser Gln His Pro Arg Thr Lys Ser Ser Arg Leu Gln Gly 4077                                                    4104
TCT AGT TTA TCT TCA GAA TCA GCC AGG CAC AAA GCT GTT GAA TTT CCT TCA GGA
Ser Ser Leu Ser Ser Glu Ser Ala Arg His Lys Ala Val Glu Phe Pro Ser Gly 4131                                                    4158
GCG AAA TCT CCC TCC AAA AGT GGT GCT CAG ACA CCC AAA AGT CCA CCT GAA CAC
Ala Lys Ser Pro Ser Lys Ser Gly Ala Gln Thr Pro Lys Ser Pro Pro Glu His 4185                                                    4212
TAT GTT CAG GAG ACC CCA CTC ATG TTT AGC AGA TGT ACT TCT GTC AGT TCA CTT
Tyr Val Gln Glu Thr Pro Leu Met Phe Ser Arg Cys Thr Ser Val Ser Ser Leu
```

FIG. 70

```
Tyr Val Gln Glu Thr Pro Leu MET Phe Ser Arg Cys Thr Ser Val Ser Ser Leu
                                                                          4266
GAT AGT TTT GAG AGT CGT TCG ATT GCC AGC TCC GTT CAG AGT GAA CCA TGC AGT
Asp Ser Phe Glu Ser Arg Ser Ile Ala Ser Ser Val Gln Ser Glu Pro Cys Ser
         4239                                                             4320
GGA ATG GTA AGT GGC ATT ATA AGC CCC AGT GAT CTT CCA GAT AGC CCT GGA CAA
Gly MET Val Ser Gly Ile Ile Ser Pro Ser Asp Leu Pro Asp Ser Pro Gly Gln
         4293                                                             4374
ACC ATG CCA CCA AGC AGA AGT AAA ACA CCT CCA CCT CCT CAA ACA GCT CAA
Thr MET Pro Pro Ser Arg Ser Lys Thr Pro Pro Pro Pro Gln Thr Ala Gln
         4347                                                             4428
ACC AAG CGA GAA GTA CCT AAA AAT GCA CCT ACT GCT GAA AAG AGA GAG AGT
Thr Lys Arg Glu Val Pro Lys Asn Ala Pro Thr Ala Glu Lys Arg Glu Ser
         4401                                                             4482
GGA CCT AAG CAA GCT GCA GTA AAT GCT GCA GTT CAG AGG GTC CAG GTT CTT CCA
Gly Pro Lys Gln Ala Ala Val Asn Ala Ala Val Gln Arg Val Gln Val Leu Pro
         4455
```

FIG. 7P

```
                                                                    4536
GAT GCT GAT ACT TTA CAT TTT GCC ACA GAA AGT ACT CCA GAT GGA TTT TCT
Asp Ala Asp Thr Leu His Phe Ala Thr Glu Ser Thr Pro Asp Gly Phe Ser

4590
TGT TCA TCC AGC CTG AGT GCT CTG AGC CTC GAT GAG CCA TTT ATA CAG AAA GAT
Cys Ser Ser Ser Leu Ser Ala Leu Ser Leu Asp Glu Pro Phe Ile Gln Lys Asp

4644
GTG GAA TTA AGA ATA ATG CCT CCA GTT CAG GAA AAT GAC AAT GGG AAT GAA ACA
Val Glu Leu Arg Ile MET Pro Pro Val Gln Glu Asn Asp Asn Gly Asn Glu Thr

4698
GAA TCA GAG CAG CCT AAA GAA TCA AAT GAA AAC CAA GAG AAA GAG GCA GAA AAA
Glu Ser Glu Gln Pro Lys Glu Ser Asn Glu Asn Gln Glu Lys Glu Ala Glu Lys

4752
ACT ATT GAT TCT GAA AAG GAC CTA TTA GAT GAT TCA GAT GAT GAT ATT GAA
Thr Ile Asp Ser Glu Lys Asp Leu Leu Asp Asp Ser Asp Asp Asp Ile Glu

4806
ATA CTA GAA GAA TGT ATT ATT TCT GCC ATG CCA ACA AAG TCA TCA CGT AAA GGC
Ile Leu Glu Glu Cys Ile Ile Ser Ala MET Pro Thr Lys Ser Ser Arg Lys Gly
```

FIG. 7Q

```
AAA AAG CCA GCC CAG ACT GCT TCA AAA TTA CCT CCA CCT GTG GCA AGG AAA CCA
Lys Lys Pro Ala Gln Thr Ala Ser Lys Leu Pro Pro Pro Val Ala Arg Lys Pro
4833                                                                    4860

AGT CAG CTG CCT GTG TAC AAA CTT CTA CCA TCA CAA AAC AGG TTG CAA CCC CAA
Ser Gln Leu Pro Val Tyr Lys Leu Leu Pro Ser Gln Asn Arg Leu Gln Pro Gln
4887                                                                    4914

AAG CAT GTT AGT TTT ACA CCG GGG GAT GAT ATG CCA CGG GTG TAT TGT GTT GAA
Lys His Val Ser Phe Thr Pro Gly Asp Asp MET Pro Arg Val Tyr Cys Val Glu
4941                                                                    4968

GGG ACA CCT ATA AAC TTT TCC ACA GCT ACA TCT CTA AGT GAT CTA ACA ATC GAA
Gly Thr Pro Ile Asn Phe Ser Thr Ala Thr Ser Leu Ser Asp Leu Thr Ile Glu
4995                                                                    5022

TCC CCT CCA AAT GAG TTA GCT GCT GGA GAA GGA GTT AGA GGA GGA GCA CAG TCA
Ser Pro Pro Asn Glu Leu Ala Ala Gly Glu Gly Val Arg Gly Gly Ala Gln Ser
5049                                                                    5076

GGT GAA TTT GAA AAA CGA GAT ACC ATT CCT ACA GAA GGC AGA AGT ACA GAT GAG
Gly Glu Phe Glu Lys Arg Asp Thr Ile Pro Thr Glu Gly Arg Ser Thr Asp Glu
5103                                                                    5130
```

FIG. 7R

```
                                            5157                                                                  5184
GCT CAA GGA AAA ACC TCA TCT GTA ACC ATA CCT GAA TTG GAT GAC AAT AAA
Ala Gln Gly Lys Thr Ser Ser Val Thr Ile Pro Glu Leu Asp Asp Asn Lys 5211                                                                  5238
GCA GAG GAA GGT GAT ATT CTT GCA GAA TGC ATT AAT TCT GCT ATG CCC AAA GGG
Ala Glu Glu Gly Asp Ile Leu Ala Glu Cys Ile Asn Ser Ala MET Pro Lys Gly 5265                                                                  5292
AAA AGT CAC AAG CCT TTC CGT GTG AAA AAG ATA ATG GAC CAG GTC CAG CAA GCA
Lys Ser His Lys Pro Phe Arg Val Lys Lys Ile MET Asp Gln Val Gln Gln Ala 5319                                                                  5346
TCT GCG TCG TCT GCA CCC AAC AAA AAT CAG TTA GAT GGT AAG AAA AAG AAA
Ser Ala Ser Ser Ala Pro Asn Lys Asn Gln Leu Asp Gly Lys Lys Lys Lys 5373                                                                  5400
CCA ACT TCA CCA GTA AAA CCT ATA CCA CAA AAT ACT GAA TAT AGG ACA CGT GTA
Pro Thr Ser Pro Val Lys Pro Ile Pro Gln Asn Thr Glu Tyr Arg Thr Arg Val
```

FIG. 7S

```
                                                         5454
AGA AAA AAT GCA GAC TCA AAA AAT AAT TTA AAT AAT GCT GAG AGA GTT TTC TCA GAC
Arg Lys Asn Ala Asp Ser Lys Asn Asn Leu Asn Asn Ala Glu Arg Val Phe Ser Asp

5508
AAC AAA GAT TCA AAG AAA CAG AAT TTG AAA AAT TCC AAG GAC TTC AAT GAT
Asn Lys Asp Ser Lys Lys Gln Asn Leu Lys Asn Ser Lys Asp Phe Asn Asp

5562
AAG CTC CCA AAT AAT GAA GAT AGA GTC AGA GGA AGT TTT GCT TTT GAT TCA CCT
Lys Leu Pro Asn Asn Glu Asp Arg Val Arg Gly Ser Phe Ala Phe Asp Ser Pro

5616
CAT CAT TAC ACG CCT ATT GAA GGA ACT CCT TAC TGT TTT TCA CGA AAT GAT TCT
His His Tyr Thr Pro Ile Glu Gly Thr Pro Tyr Cys Phe Ser Arg Asn Asp Ser

5670
TTG AGT TCT CTA GAT TTT GAT GAT GAT GTT GAC CTT TCC AGG GAA AAG GCT
Leu Ser Ser Leu Asp Phe Asp Asp Asp Val Asp Leu Ser Arg Glu Lys Ala

5724
GAA TTA AGA AAG GCA AAA GAA AAT AAG GAA TCA GAG GCT AAA GTT ACC AGC CAC
Glu Leu Arg Lys Ala Lys Glu Asn Lys Glu Ser Glu Ala Lys Val Thr Ser His
```

FIG. 7T

```
        5751
ACA GAA CTA ACC TCC AAC CAA TCA GCT AAT AAG ACA CAA GCT ATT GCA AAG
Thr Glu Leu Thr Ser Asn Gln Ser Ala Asn Lys Thr Gln Ala Ile Ala Lys
                                                                    5778

5805
CAG CCA ATA AAT CGA GGT CAG CCT AAA CCC ATA CTT CAG AAA CAA TCC ACT TTT
Gln Pro Ile Asn Arg Gly Gln Pro Lys Pro Ile Leu Gln Lys Gln Ser Thr Phe
                                                                    5832

5859
CCC CAG TCA TCC AAA GAC ATA CCA GAC AGA GGG GCA GCA ACT GAT GAA AAG TTA
Pro Gln Ser Ser Lys Asp Ile Pro Asp Arg Gly Ala Ala Thr Asp Glu Lys Leu
                                                                    5886

5913
CAG AAT TTT GCT ATT GAA AAT ACT CCA GTT TGC TTT TCT CAT AAT TCC TCT CTG
Gln Asn Phe Ala Ile Glu Asn Thr Pro Val Cys Phe Ser His Asn Ser Ser Leu
                                                                    5940

5967
AGT TCT CTC AGT GAC ATT GAC CAA GAA AAC AAC AAT AAA GAA AAT GAA CCT ATC
Ser Ser Leu Ser Asp Ile Asp Gln Glu Asn Asn Asn Lys Glu Asn Glu Pro Ile
                                                                    5994
```

FIG. 7U

```
                                                    6021                                              6048
AAA GAG ACT GAG CCC CCT GAC TCA CAG GGA GAA CCA AGT AAA CCT CAA GCA TCA
Lys Glu Thr Glu Pro Pro Asp Ser Gln Gly Glu Pro Ser Lys Pro Gln Ala Ser 6075                                              6102
GGC TAT GCT CCT AAA TCA TTT CAT GTT GAA GAT ACC CCA GTT TGT TTC TCA AGA
Gly Tyr Ala Pro Lys Ser Phe His Val Glu Asp Thr Pro Val Cys Phe Ser Arg 6129                                              6156
AAC AGT TCT CTC AGT TCT CTT AGT ATT GAC TCT GAA GAT GAC CTG TTG CAG GAA
Asn Ser Ser Leu Ser Ser Leu Ser Ile Asp Ser Glu Asp Asp Leu Leu Gln Glu 6183                                              6210
TGT ATA AGC TCC GCA ATG CCA AAA AAG AAA CCT TCA AGA CTC AAG GGT GAT
Cys Ile Ser Ser Ala MET Pro Lys Lys Lys Pro Ser Arg Leu Lys Gly Asp 6237                                              6264
AAT GAA AAA CAT AGT CCC AGA AAT ATG GGT GGC ATA TTA GGT GAA GAT CTG ACA
Asn Glu Lys His Ser Pro Arg Asn MET Gly Gly Ile Leu Gly Glu Asp Leu Thr 6291                                              6318
CTT GAT TTG AAA GAT ATA CAG AGA CCA GAT TCA GAA CAT GGT CTA TCC CCT GAT
Leu Asp Leu Lys Asp Ile Gln Arg Pro Asp Ser Glu His Gly Leu Ser Pro Asp
```

FIG. 7V

```
TCA GAA AAT TTT GAT TGG AAA GCT ATT CAG GAA GGT GCA AAT TCC ATA GTA AGT
Ser Glu Asn Phe Asp Trp Lys Ala Ile Gln Glu Gly Ala Asn Ser Ile Val Ser
                6345                                                    6372

AGT TTA CAT CAA GCT GCT GCT GCA TGT TTA TCT AGA CAA GCT TCG TCT GAT
Ser Leu His Gln Ala Ala Ala Ala Cys Leu Ser Arg Gln Ala Ser Ser Asp
                6399                                                    6426

TCA GAT TCC ATC CTT TCC CTG AAA TCA GGA ATC TCT CTG GGA TCA CCA TTT CAT
Ser Asp Ser Ile Leu Ser Leu Lys Ser Gly Ile Ser Leu Gly Ser Pro Phe His
                6453                                                    6480

CTT ACA CCT GAT CAA GAA AAA CCC TTT ACA AGT AAT AAA GGC CCA CGA ATT
Leu Thr Pro Asp Gln Glu Lys Pro Phe Thr Ser Asn Lys Gly Pro Arg Ile
                6507                                                    6534

CTA AAA CCA GGG GAG AAA AGT ACA TTG GAA ACT AAA AAG ATA GAA TCT GAA AGT
Leu Lys Pro Gly Glu Lys Ser Thr Leu Glu Thr Lys Lys Ile Glu Ser Glu Ser
                6561                                                    6588

```
AAA GGA ATC AAA GGA GGA AAA GTT TAT AAA AGT TTG ATT ACT GGA AAA GTT
Lys Gly Ile Lys Gly Gly Lys Val Tyr Lys Ser Leu Ile Thr Gly Lys Val
                                                                    6696
CGA TCT AAT TCA GAA ATT TCA GGC CAA ATG AAA CAG CCC CTT CAA GCA AAC ATG
Arg Ser Asn Ser Glu Ile Ser Gly Gln MET Lys Gln Pro Leu Gln Ala Asn MET
6669                                                                 6750
CCT TCA ATC TCT CGA GGC AGG ACA ATG ATT CAT ATT CCA GGA GTT CGA AAT AGC
Pro Ser Ile Ser Arg Gly Arg Thr MET Ile His Ile Pro Gly Val Arg Asn Ser
6723                                                                 6804
TCC TCA AGT ACA AGT CCT GTT TCT AAA AAA GGC CCA CCC CTT AAG ACT CCA GCC
Ser Ser Ser Thr Ser Pro Val Ser Lys Lys Gly Pro Pro Leu Lys Thr Pro Ala
6777                                                                 6858
TCC AAA AGC CCT AGT GAA GGT CAA ACA GCC ACC ACT TCT CCT AGA GGA GCC AAG
Ser Lys Ser Pro Ser Glu Gly Gln Thr Ala Thr Thr Ser Pro Arg Gly Ala Lys
6831                                                                 6912
CCA TCT GTG AAA TCA GAA TTA AGC CCT GTT GCC AGG CAG ACA TCC CAA ATA GGT
Pro Ser Val Lys Ser Glu Leu Ser Pro Val Ala Arg Gln Thr Ser Gln Ile Gly
6885
```

FIG. 7X

```
                                                                                6939                                                                            6966
GGG TCA AGT AAA GCA CCT TCT AGA TCA GGA TCT AGA GAT TCG ACC CCT TCA AGA
Gly Ser Ser Lys Ala Pro Ser Arg Ser Gly Ser Arg Asp Ser Thr Pro Ser Arg 6993                                                                            7020
CCT GCC CAG CAA CCA TTA AGT AGA CCT ATA CAG TCT CCT GGC CGA AAC TCA ATT
Pro Ala Gln Gln Pro Leu Ser Arg Pro Ile Gln Ser Pro Gly Arg Asn Ser Ile 7047                                                                            7074
TCC CCT GGT AGA AAT GGA ATA AGT CCT AAC AAA TTA TCT CAA CTT CCA AGG
Ser Pro Gly Arg Asn Gly Ile Ser Pro Asn Lys Leu Ser Gln Leu Pro Arg 7101                                                                            7128
ACA TCA TCC CCT AGT ACT GCT TCA ACT AAG TCC TCA GGT TCT GGA AAA ATG TCA
Thr Ser Ser Pro Ser Thr Ala Ser Thr Lys Ser Ser Gly Ser Gly Lys MET Ser 7155                                                                            7182
TAT ACA TCT CCA GGT AGA CAG ATG AGC CAA CAG AAC CTT ACC AAA CAA ACA GGT
Tyr Thr Ser Pro Gly Arg Gln MET Ser Gln Gln Asn Leu Thr Lys Gln Thr Gly 7209                                                                            7236
TTA TCC AAG AAT GCC AGT AGT AGT ATT CCA AGA AGT GAG TCT GCC TCC AAA GGA CTA
```

FIG. 7Y

```
    Leu Ser Lys Asn Ala Ser Ser Ile Pro Arg Ser Glu Ser Ala Ser Lys Gly Leu
                                                 7263                              7290
    AAT CAG ATG AAT AAT GGT AAT GCC AAT AAA AAG GTA GAA CTT TCT AGA ATG
    Asn Gln MET Asn Asn Gly Asn Ala Asn Lys Lys Val Glu Leu Ser Arg MET
                                      7317                                         7344
    TCT TCA ACT AAA TCA AGT GGA AGT GAA TCT GAT AGA TCA GAA AGA CCT GTA TTA
    Ser Ser Thr Lys Ser Ser Gly Ser Glu Ser Asp Arg Ser Glu Arg Pro Val Leu
                     7371                                                          7398
    GTA CGC CAG TCA ACT TTC ATC AAA GAA GCT CCA AGC CCA ACC TTA AGA AGA AAA
    Val Arg Gln Ser Thr Phe Ile Lys Glu Ala Pro Ser Pro Thr Leu Arg Arg Lys
                                 7425                                              7452
    TTG GAG GAA TCT GCT TCA TTT GAA TCT CTT TCT CCA TCA TCT AGA CCA GCT TCT
    Leu Glu Glu Ser Ala Ser Phe Glu Ser Leu Ser Pro Ser Ser Arg Pro Ala Ser
                           7479                                                    7506
    CCC ACT AGG TCC CAG GCA CAA ACT CCA GTT TTA AGT CCT TCC CTT CCT GAT ATG
    Pro Thr Arg Ser Gln Ala Gln Thr Pro Val Leu Ser Pro Ser Leu Pro Asp MET
```

FIG. 7Z

```
                                                                        7560
TCT CTA TCC ACA CAT TCG TCT GTT CAG GCT GGT GGA TGG CGA AAA CTC CCA CCT
Ser Leu Ser Thr His Ser Ser Val Gln Ala Gly Gly Trp Arg Lys Leu Pro Pro

7614
AAT CTC AGT CCC ACT ATA GAG TAT AAT GAT GGA AGA CCA GCA AAG CGC CAT GAT
Asn Leu Ser Pro Thr Ile Glu Tyr Asn Asp Gly Arg Pro Ala Lys Arg His Asp

7668
ATT GCA CGG TCT CAT TCT GAA AGT CCT TCT AGA CTT CCA ATC AAT AGG TCA GGA
Ile Ala Arg Ser His Ser Glu Ser Pro Ser Arg Leu Pro Ile Asn Arg Ser Gly

7722
ACC TGG AAA CGT GAG CAC AGC AAA CAT TCA TCA TCC CTT CCT CGA GTA AGC ACT
Thr Trp Lys Arg Glu His Ser Lys His Ser Ser Ser Leu Pro Arg Val Ser Thr

7776
TGG AGA AGA ACT GGA AGT TCA TCT TCA ATT CTT TCT GCT TCA GAA TCC AGT
Trp Arg Arg Thr Gly Ser Ser Ser Ile Leu Ser Ala Ser Glu Ser Ser

7830
GAA AAA GCA AAA AGT GAG GAT GAA AAA CAT GTG AAC TCT ATT TCA GGA ACC AAA
Glu Lys Ala Lys Ser Glu Asp Glu Lys His Val Asn Ser Ile Ser Gly Thr Lys
```

FIG. 7AA

```
                                                        7857                                                              7884
CAA AGT AAA GAA AAC CAA GTA TCC GCA AAA GGA ACA TGG AGA AAA ATA AAA GAA
Gln Ser Lys Glu Asn Gln Val Ser Ala Lys Gly Thr Trp Arg Lys Ile Lys Glu 7911                                                              7938
AAT GAA TTT TCT CCC ACA AAT AGT ACT TCT CAG ACC GTT TCC TCA GGT GCT ACA
Asn Glu Phe Ser Pro Thr Asn Ser Thr Ser Gln Thr Val Ser Ser Gly Ala Thr 7965                                                              7992
AAT GGT GCT GAA TCA AAG ACT CTA ATT TAT CAA ATG GCA CCT GCT GTT TCT AAA
Asn Gly Ala Glu Ser Lys Thr Leu Ile Tyr Gln MET Ala Pro Ala Val Ser Lys 8019                                                              8046
ACA GAG GAT GTT TGG GTG AGA ATT GAG GAC TGT CCC ATT AAC AAT CCT AGA TCT
Thr Glu Asp Val Trp Val Arg Ile Glu Asp Cys Pro Ile Asn Asn Pro Arg Ser 8073                                                              8100
GGA AGA TCT CCC ACA GGT AAT ACT CCC CCG GTG ATT GAC AGT GTT TCA GAA AAG
Gly Arg Ser Pro Thr Gly Asn Thr Pro Pro Val Ile Asp Ser Val Ser Glu Lys 8127                                                              8154
GCA AAT CCA AAC ATT AAA GAT TCA AAA GAT AAT CAG GCA AAA CAA AAT GTG GGT
Ala Asn Pro Asn Ile Lys Asp Ser Lys Asp Asn Gln Ala Lys Gln Asn Val Gly
```

FIG. 7BB

```
                                                                              8208
AAT GGC AGT GTT CCC ATG CGT ACC GTG GGT TTG GAA AAT CGC CTG ACC TCC TTT
Asn Gly Ser Val Pro MET Arg Thr Val Gly Leu Glu Asn Arg Leu Thr Ser Phe

8262
ATT CAG GTG GAT GCC CCT GAC CAA GTA AAA GGA ACT GAG ATA AAA CCA GGA CAA AAT
Ile Gln Val Asp Ala Pro Asp Gln Val Lys Gly Thr Glu Ile Lys Pro Gly Gln Asn

8316
AAT CCT GTC CCT GTA TCA GAG ACT AAT GAA AGT CCT ATA GTG GAA CGT ACC CCA
Asn Pro Val Pro Val Ser Glu Thr Asn Glu Ser Pro Ile Val Glu Arg Thr Pro

8370
TTC AGT TCT AGC AGC TCA AGC AAA CAC AGT TCA CCT AGT GGG ACT GTT GCT GCC
Phe Ser Ser Ser Ser Ser Lys His Ser Ser Pro Ser Gly Thr Val Ala Ala

8424
AGA GTG ACT CCT TTT AAT TAC AAC CCA AGC CCT AGG AAA AGC AGC GCA GAT AGC
Arg Val Thr Pro Phe Asn Tyr Asn Pro Ser Pro Arg Lys Ser Ser Ala Asp Ser
```
        8181                  8235                  8289                  8343                  8397

FIG. 7CC

```
                                                                              8478
ACT TCA GCT CGG CCA TCT CAG ATC CCA ACT CCA GTG AAT AAC ACA AAG AAG
Thr Ser Ala Arg Pro Ser Gln Ile Pro Thr Pro Val Asn Asn Thr Lys Lys

8532
CGA GAT TCC AAA ACT GAC AGC ACA GAA TCC AGT GGA ACC CAA AGT CCT AAG CGC
Arg Asp Ser Lys Thr Asp Ser Thr Glu Ser Ser Gly Thr Gln Ser Pro Lys Arg

8559
CAT TCT GGG TCT TAC CTT GTG ACA TCT GTT TAA
His Ser Gly Ser Tyr Leu Val Thr Ser Val  .

8570      8580      8590      8600      8610
AAGAG AGGAAGAATG AAACTAAGAA AATTCTATGT TAATTACAAC 8620      8630      8640      8650      8660      8670      8680
TGCTATATAG ACATTTGTT TCAAATGAAA CTTTAAAGA CTGAAAAATT TTGTAAATAG GTTTGATTCT 8690      8700      8710      8720      8730      8740      8750
TGTTAGAGGG TTTTTGTTCT GGAAGCCATA TTTGATAGTA TACTTTGTCT TCACTGGTCT TATTTTGGGA 8760      8770      8780      8790      8800      8810      8820
GGCACTCTTG ATGGTTAGGS AAAAAATAGK AAAGCCAAGT ATGTTTGTAC AGTATGTTTT ACATGTATTT 8830      8840      8850      8860      8870      8880      8890
AAAGTAGCAT CCCATCCCAA CTTCCYTTAA TTATTGCTTG TCYTAAAATA ATGAACACTA CAGATAGGAA
```

FIG. 7DD

```
        8900        8910        8920        8930        8940        8950        8960
ATATGATATA  TTGCTGTTAT  CAATCATTTC  TAGATTATAA  ACTGACTAAA  CTTACATCAG  GGGAAAATTG 8970        8980        8990        9000        9010        9020        9030
GTATTTATGC  AAAAAAAAAA  TGTTTTTGTC  CTTGTGAGTC  CATCTAACAT  CATAATTAAT  CATGTGGCTG 9040        9050        9060        9070        9080        9090        9100
TGAAATTCAC  AGTAATATGG  TTCCCGATGA  ACAAGTTTAC  CCAGCCTGCT  TTGCTTNACT  GCATGAATGA 9110        9120        9130        9140        9150        9160        9170
AACTGATGGT  TCAATTTCAG  AAGTAAATGAT  TAACAGTTAT  GTGGTCACAT  GATGTGCATA  GAGATAGCTA 9180        9190        9200        9210        9220        9230        9240
CAGTGTAATA  ATTTACACTA  TTTTGTGCTC  CAAACAAAAC  AAAAATCTGT  GTAACTGTAA  AACATTGAAT 9250        9260        9270        9280        9290        9300        9310
GAAACTATTT  TACCTGAACT  AGATTTTATC  TGAAAGTAGG  TAGAATTTTT  GCTATGCTGT  AATTTGTTGT 9320        9330        9340        9350        9360        9370        9380
ATATTCTGGT  ATTTGAGGTG  AGATGGCTGC  TCTTTKATTA  ATGAGACATG  AATTGTGTCT  CAACAGAAAC 9390        9400        9410        9420        9430        9440        9450
TAAATGAACA  TTTCAGAATA  AATTATTGCT  GTATGTAAAC  TGTTACTGAA  ATTGGTATTT  GTTTGAAGGG 9460        9470        9480        9490        9500        9510        9520
TSTTGTTTCA  CATTTGTATT  AATTAATTGT  TTAAAATGCC  TCTTTTAAAA  GCTTATATAA  ATTTTTNCT
```

FIG. 7EE

```
           9530       9540       9550       9560       9570       9580       9590
TCAGCTTCTA TGCATTAAGA GTAAAATTCC TCTTACTGTA ATAAAAACAR TTGAAGAAGA CTGTTGCCAC 9600       9610       9620       9630       9640       9650       9660
TTAACCATTC CATGCGTTGG CACTTATCTA TTCCTGAAAT TTCTTTTATG TGATTAGCTC ATCTTGATTT 9670       9680       9690       9700       9710       9720       9730
TWAAYATTTT TCCACTTAAA CTTTTTTTTC TTACTCCACT GGAGCTCAGT AAAAGTAAAT TCATGTAATA 9740       9750       9760       9770       9780       9790       9800
GCAATGCAAG CAGCCTAGCA CAGACTAAGC ATTGAGCATA ATAGGCCCAC ATAATTTCCT CTTTCTTAAT 9810       9820       9830       9840       9850       9860       9870
AWTATAGAAT TCTGTACTTG AAATTRATTC TTAGACATTG CAGTCTCTTC GAGGCTTTAC AGTGTAAACT 9880       9890       9900       9910       9920       9930       9940
GTCTTGCCCC TTCATCTTCT TGTTGCAACT GGGTCTGACA TGAACACTTT TTATCACCCT GTATGTTAGG 9950       9960       9970       9980       9990       10000      10010
GCAAGATCTC AGCAGTGAAG TATAATCAGC ACTTTGCCAT GCTCANRAAA TTCAAATCAC ATGGAACTTT
```

FIG. 7FF

```
          10020      10030      10040      10050      10060      10070      10080
AGAGGTAGAT TTAATACGAT TAAGATATTC AGAAGTATAT TTTAGAATCC CTGCCTGTTA AGGAAACTTT 10090      10100      10110      10120      10130      10140      10150
ATTTGTGGTA GGTACAGTTC TGGGGTACAT GTTAAGTGTC CCCTTATACA GTGGAGGGAA GTCTTCCTTC 10160      10170      10180      10190      10200      10210      10220
CTGAAGGRAA ATAAACTGAC ACTTATTAAC TAAGATAATT TACTTAATAT ATCTYCCCTG ATTTGTTTTA 10230      10240      10250      10260      10270      10280      10290
AAAGATCAGA GGGTGACTGA TGATACATGC ATACATATTT GTTGAATAAA TGAAAATTTA TTTTTAGTGA 10300      10310      10320      10330      10340      10350      10360
TAAGANTCAT ACACTCTGTA TTTGGGGAGR GAAAACCTTT TTAAGCATGG TGGGGCACTC AGATAGGNGT 10370      10380
NAATACACCT ACCTGGTGGT CAT
```

DIAGNOSIS FOR MUTANT APC BY IMMUNOASSAY

This application is a division of application Ser. No. 08/289,548, Aug. 12, 1994, now issued as U.S. Pat. No. 5,648,212 which is a division of application Ser. No. 07/741,940 filed Aug. 8, 1991 (issued as U.S. Pat. No 5,352,775).

The U.S. Government has a paid-up license in this invention and The right in limited circumstances to require the patent owner to license others on reasonable terms as provided for by the terms of grants awarded by the National Institutes of Health.

TECHNICAL AREA OF THE INVENTION

The invention relates to the area of cancer diagnostics and therapeutics. More particularly, the invention relates to detection of the germline and somatic alterations of wild-type APC genes. In addition, it relates to therapeutic intervention to restore the function of APC gene product.

BACKGROUND OF THE INVENTION

According to the model of Knudson for tumorigenesis (Cancer Research, Vol. 45, p. 1482, 1985), there are tumor suppressor genes in all normal cells which, when they become non-functional due to mutation, cause neoplastic development. Evidence for this model has been found in the cases of retinoblastoma and colorectal tumors. The implicated suppressor genes in those tumors, RB, p53, DCC and MCC, were found to be deleted or altered in many cases of the tumors studied. (Hansen and Cavenee, Cancer Research, Vol. 47, pp. 5518–5527 (1987); Baker et al., Science, Vol. 244, p. 217 (1989); Fearon et al., Science, Vol. 247, p. 49 (1990); Kinzler et al. Science Vol. 251. p. 1366 (1991).)

In order to fully understand the pathogenesis of tumors, it will be necessary to identify the other suppressor genes that play a role in the tumorigenesis process. Prominent among these is the one(s) presumptively located at 5q21. Cytogenetic (Herrera et al., Am J. Med. Genet., Vol. 25, p. 473 (1986) and linkage (Leppert et al., Science, Vol. 238, p. 1411 (1987); Bodmer et al., Nature, Vol. 328, p. 614 (1987)) studies have shown that this chromosome region harbors the gene responsible for familial adenomatous polyposis (FAP) and Gardner's Syndrome (GS). FAP is an autosomal-dominant, inherited disease in which affected individuals develop hundreds to thousands of adenomatous polyps, some of which progress to malignancy. GS is a variant of FAP in which desmoid tumors, osteomas and other soft tissue tumors occur together with multiple adenomas of the colon and rectum. A less severe form of polyposis has been identified in which only a few (2–40) polyps develop. This condition also is familial and is linked to the same chromosomal markers as FAP and GS (Leppert et al., New England Journal of Medicine, Vol. 322, pp. 904–908, 1990.) Additionally, this chromosomal region is often deleted from the adenomas (Vogelstein et al., N. Engl. J. Med., Vol. 319, p. 525 (1988)) and carcinomas (Vogelstein et al., N. Engl. J. Med., Vol. 319, p. 525 (1988); Solomon et al., Nature, Vol. 328, p. 616 (1987); Sasaki et al., Cancer Research, Vol. 49, p. 4402 (1989); Delattre et al., Lancet, Vol. 2, p. 353 (1989); and Ashton-Rickardt et al., Oncogene, Vol. 4, p. 1169 (1989)) of patients without FAP (sporadic tumors). Thus, a putative suppressor gene on chromosome 5q21 appears to play a role in the early stages of colorectal neoplasia in both sporadic and familial tumors.

Although the MCC gene has been identified on 5q21 as a candidate suppressor gene, it does not appear to be altered in FAP or GS patients. Thus there is a need in the art for investigations of this chromosomal region to identify genes and to determine if any of such genes are associated with FAP and/or GS and the process of tumorigenesis.

SUMMARY OF THE INVENTION

It is an object of the present invention to provide a method for diagnosing and prognosing a neoplastic tissue of a human.

It is another object of the invention to provide a method of detecting genetic predisposition to cancer.

It is another object of the invention to provide a method of supplying wild-type APC gene function to a cell which has lost said gene function.

It is yet another object of the invention to provide a kit for determination of the nucleotide sequence of APC alleles by the polymerase chain reaction.

It is still another object of the invention to provide nucleic acid probes for detection of mutations in the human APC gene.

It is still another object of the invention to provide a cDNA molecule encoding the APC gene product.

It is yet another object of the invention to provide a preparation of the human APC protein.

It is another object of the invention to provide a method of screening for genetic predisposition to cancer.

It is an object of the invention to provide methods of testing therapeutic agents for the ability to suppress neoplasia.

It is still another object of the invention to provide animals carrying mutant APC alleles.

These and other objects of the invention are provided by one or more of the embodiments which are described below. In one embodiment of the present invention a method of diagnosing or prognosing a neoplastic tissue of a human is provided comprising: detecting somatic alteration of wild-type APC genes or their expression products in a sporadic colorectal cancer tissue, said alteration indicating neoplasia of the tissue.

In yet another embodiment a method is provided of detecting genetic predisposition to cancer in a human including familial adenomatous polyposis (FAP) and Gardner's Syndrome (GS), comprising: isolating a human sample selected from the group consisting of blood and fetal tissue; detecting alteration of wild-type APC gene coding sequences or their expression products from the sample, said alteration indicating genetic predisposition to cancer.

In another embodiment of the present invention a method is provided for supplying wild-type APC gene function to a cell which has lost said gene function by virtue of a mutation in the APC gene, comprising: introducing a wild-type APC gene into a cell which has lost said gene function such that said wild-type gene is expressed in the cell.

In another embodiment a method of supplying wild-type APC gene function to a cell is provided comprising: introducing a portion of a wild-type APC gene into a cell which has lost said gene function such that said portion is expressed in the cell, said portion encoding a part of the APC protein which is required for non-neoplastic growth of said cell. APC protein can also be applied to cells or administered to animals to remediate for mutant APC genes. Synthetic peptides or drugs can also be used to mimic APC function in cells which have altered APC expression.

In yet another embodiment a pair of single stranded primers is provided for determination of the nucleotide sequence of the APC gene by polymerase chain reaction. The sequence of said pair of single stranded DNA primers is derived from chromosome 5q band 21, said pair of primers allowing synthesis of APC gene coding sequences.

In still another embodiment of the invention a nucleic acid probe is provided which is complementary to human wild-type APC gene coding sequences and which can form mismatches with mutant APC genes, thereby allowing their detection by enzymatic or chemical cleavage or by shifts in electrophoretic mobility.

In another embodiment of the invention a method is provided for detecting the presence of a neoplastic tissue in a human. The method comprises isolating a body sample from a human; detecting in said sample alteration of a wild-type APC gene sequence or wild-type APC expression product, said alteration indicating the presence of a neoplastic tissue in the human.

In still another embodiment a cDNA molecule is provided which comprises the coding sequence of the APC gene.

In even another embodiment a preparation of the human APC protein is provided which is substantially free of other human proteins. The amino acid sequence of the protein is shown in FIG. 3 or 7.

In yet another embodiment of the invention a method is provided for screening for genetic predisposition to cancer, including familial adenomatous polyposis (FAP) and Gardner's Syndrome (GS), in a human. The method comprises: detecting among kindred persons the presence of a DNA polymorphism which is linked to a mutant APC allele in an individual having a genetic predisposition to cancer, said kindred being genetically related to the individual, the presence of said polymorphism suggesting a predisposition to cancer.

In another embodiment of the invention a method of testing therapeutic agents for the ability to suppress a neoplastically transformed phenotype is provided. The method comprises: applying a test substance to a cultured epithelial cell which carries a mutation in an APC allele; and determining whether said test substance suppresses the neoplastically transformed phenotype of the cell.

In another embodiment of the invention a method of testing therapeutic agents for the ability to suppress a neoplastically transformed phenotype is provided. The method comprises: administering a test substance to an animal which carries a mutant APC allele; and determining whether said test substance prevents or suppresses the growth of tumors.

In still other embodiments of the invention transgenic animals are provided. The animals carry a mutant APC allele from a second animal species or have been genetically engineered to contain an insertion mutation which disrupts an APC allele.

The present invention provides the art with the information that the APC gene, a heretofore unknown gene is, in fact, a target of mutational alterations on chromosome 5q21 and that these alterations are associated with the process of tumorigenesis. This information allows highly specific assays to be performed to assess the neoplastic status of a particular tissue or the predisposition to cancer of an individual. This invention has applicability to Familial Adenomatous Polyposis, sporadic colorectal cancers, Gardner's Syndrome, as well as the less severe familial polyposis discusses above.

The cDNA sequence of the TB2 gene was determined from the YS-39 clone derived as described in the text. This clone consisted of 2300 bp and defined an ORF of 185 amino acids beginning at nucleotide 1. Only the predicted amino acids are shown. The carboxy terminal end of the ORF has apparently been identified, but the 5' end of the TB2 transcript has not been precisely determined.

Figures 1, 1B, 2:
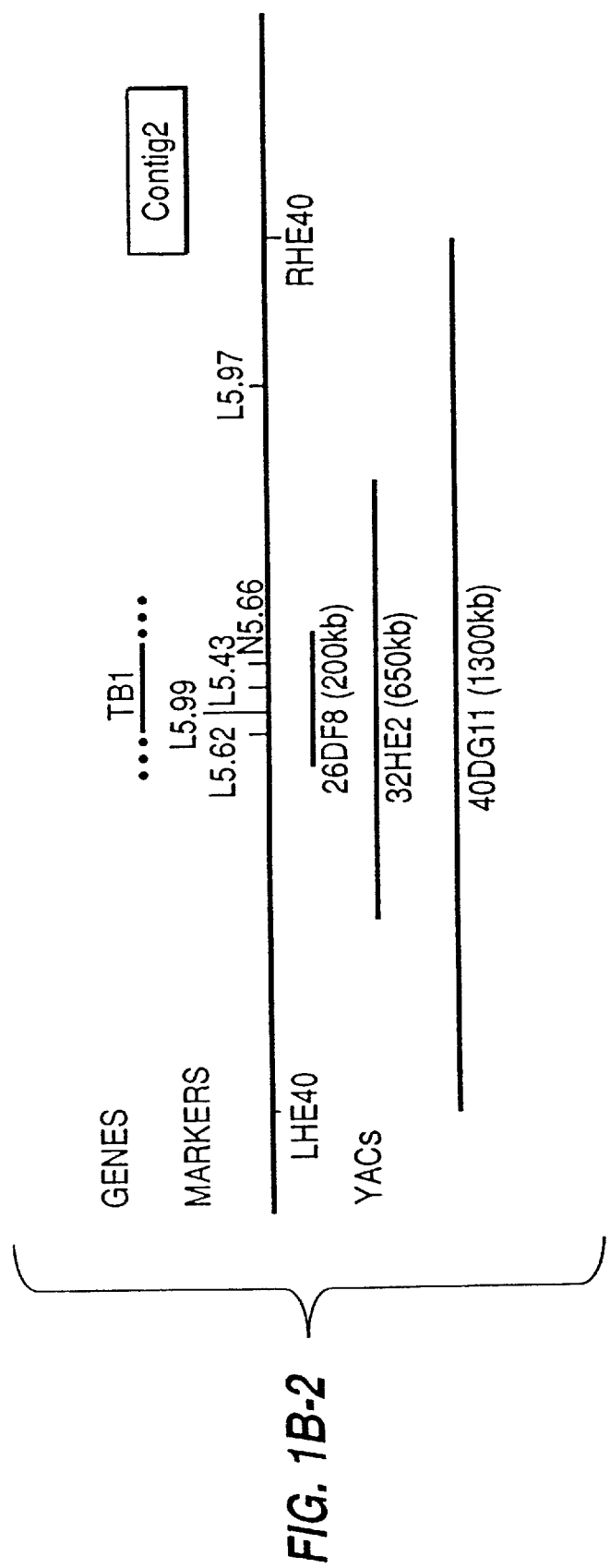
FIG. 1B shows a detailed map of the three central contigs. The position of the six identified genes from within the FAP region is shown; the 5' and 3' ends of the transcripts from these genes have in general not yet been isolated, as indicated by the string of dots surrounding the bars denoting the genes' positions. Selected restriction endonuclease recognition sites are indicated. B, BssH2; S, SstII; M, MluI; N, NruI.
Figures 1, 1B, 2, 3:
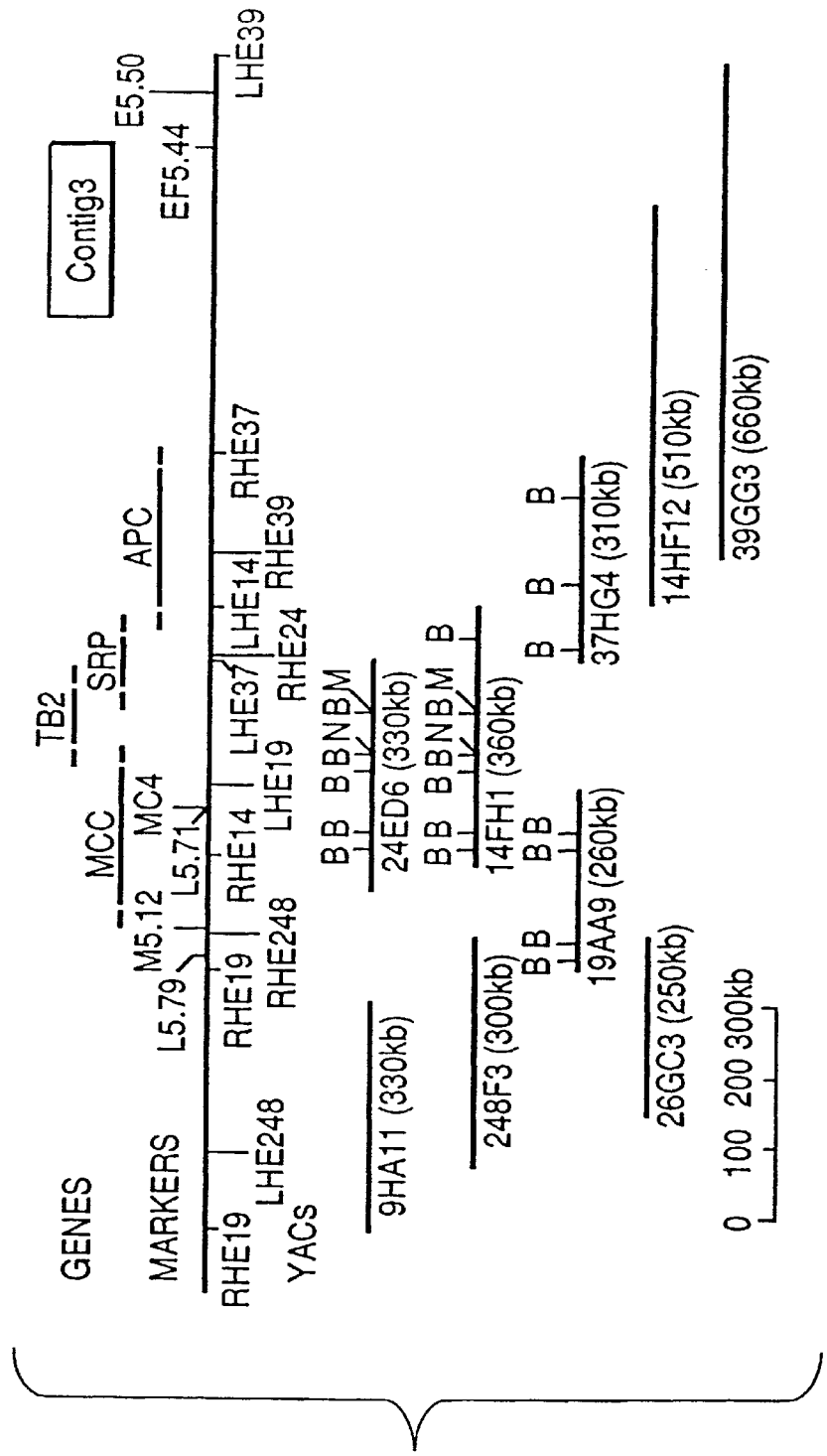

FIG. 3 shows the sequence of the APC gene product (SEQ ID NO: 7). The cDNA sequence was determined through the analysis of 87 cDNA clones derived from normal colon, liver, and brain. A total of 8973 bp were contained within overlapping cDNA clones, defining an ORF of 2842 amino acids. In frame stop codons surrounded this ORF, as described in the text, suggesting that the entire APC gene product was represented in the ORF illustrated. Only the predicted amino acids are shown.

FIGS. 4A & B show the local similarity between human APC (SEQ ID NO: 7) and ral2 of yeast (SEQ ID NO:8). Local similarity among the APC and MCC (SEQ ID NO:10) genes and the m3 muscarinic acetylcholine receptor (SEQ ID NO: 9) is shown. The region of the mAChR shown corresponds to that responsible for coupling the receptor to G proteins. The connecting lines indicate identities; dots indicate related amino acids residues.

Figure 5:
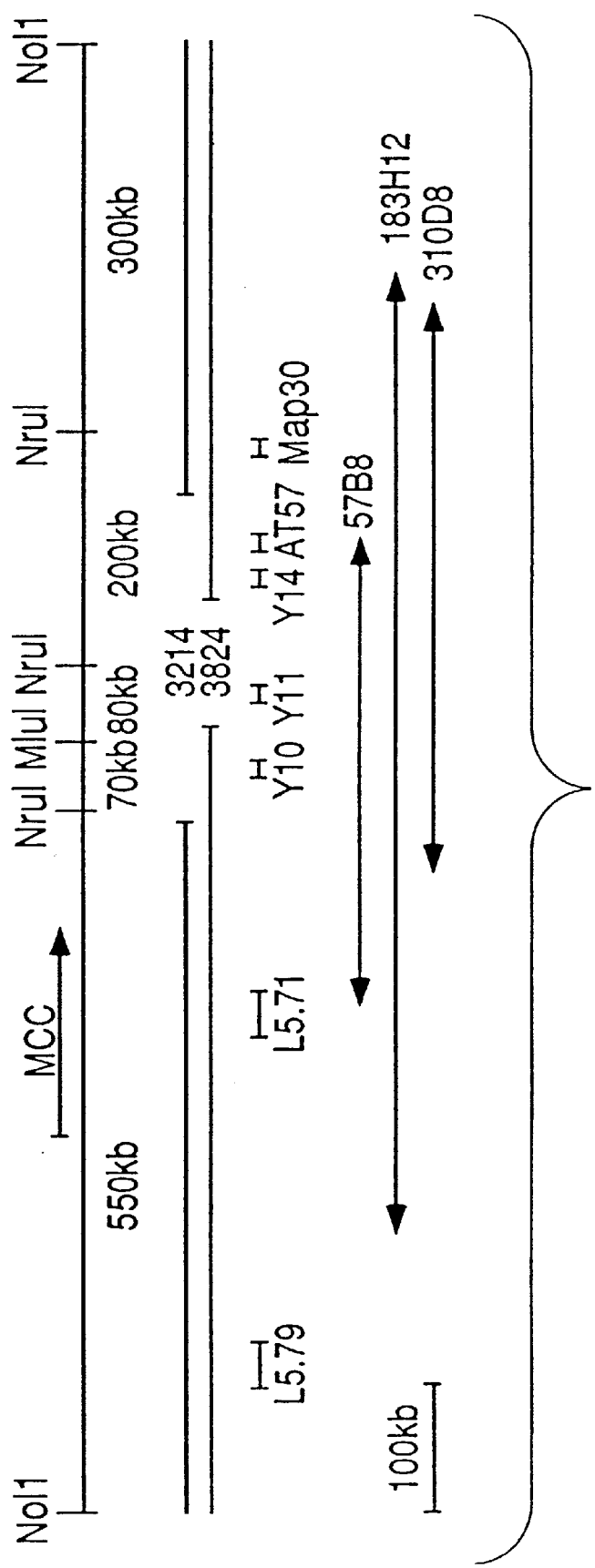

FIG. 5 shows the genomic map of the 1200 kb NotI fragment at the FAP locus. The NotI fragment is shown as a bold line. Relevant parts of the deletion chromosomes from patients 3214 and 3824 are shown as stippled lines. Probes used to characterize the NotI fragment and the deletions, and three YACs from which subclones were obtained, are shown below the restriction map. The chimeric end of YAC 183H12 is indicated by a dotted line. The orientation and approximate position of MCC are indicated above the map.

FIG. 6 shows the DNA sequence and predicted amino acid sequence of DP1 (TB2). The nucleotide numbering begins at the most 5' nucleotide isolated. A proposed initiation methionine (base 77) is indicated in bold type. The entire coding sequence is presented.

FIG. 7 shows the cDNA and predicted amino acid sequence of DP2.5 (APC). The nucleotide numbering begins at the proposed initiation methionine. The nucleotides and amino acids of the alternatively spliced exon (exon 9; nucleotide positions 934–1236) are presented in lower case letters. At the 3' end, a poly(A) addition signal occurs at 9530, and one cDNA clone has a poly(A) at 9563. Other cDNA clones extend beyond 9563, however, and their consensus sequence is included here.

Figure 8A:
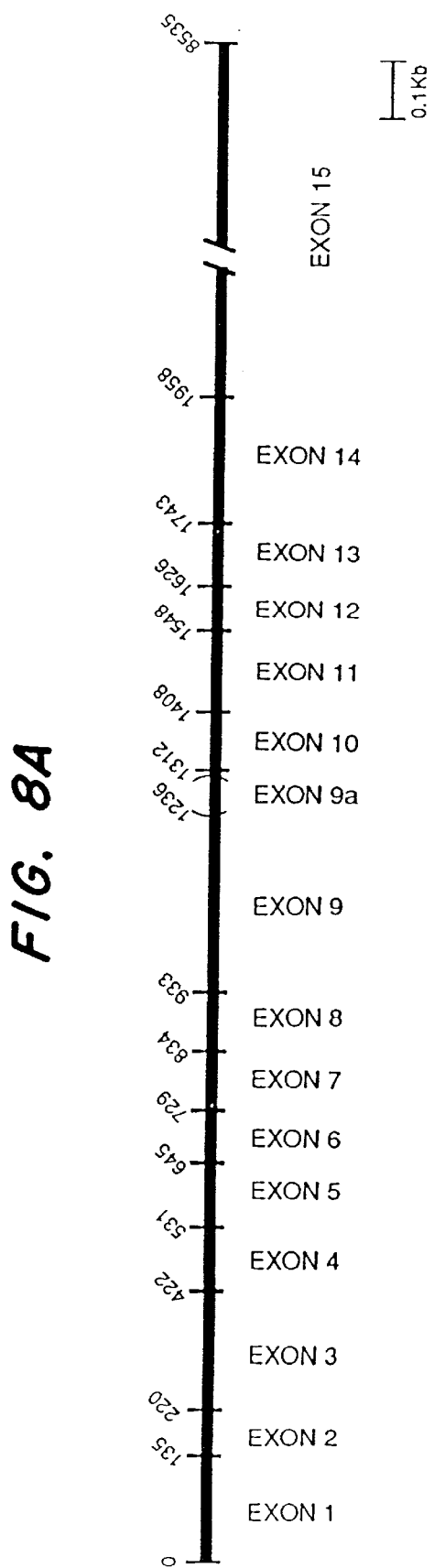
Figures 1, 8B:
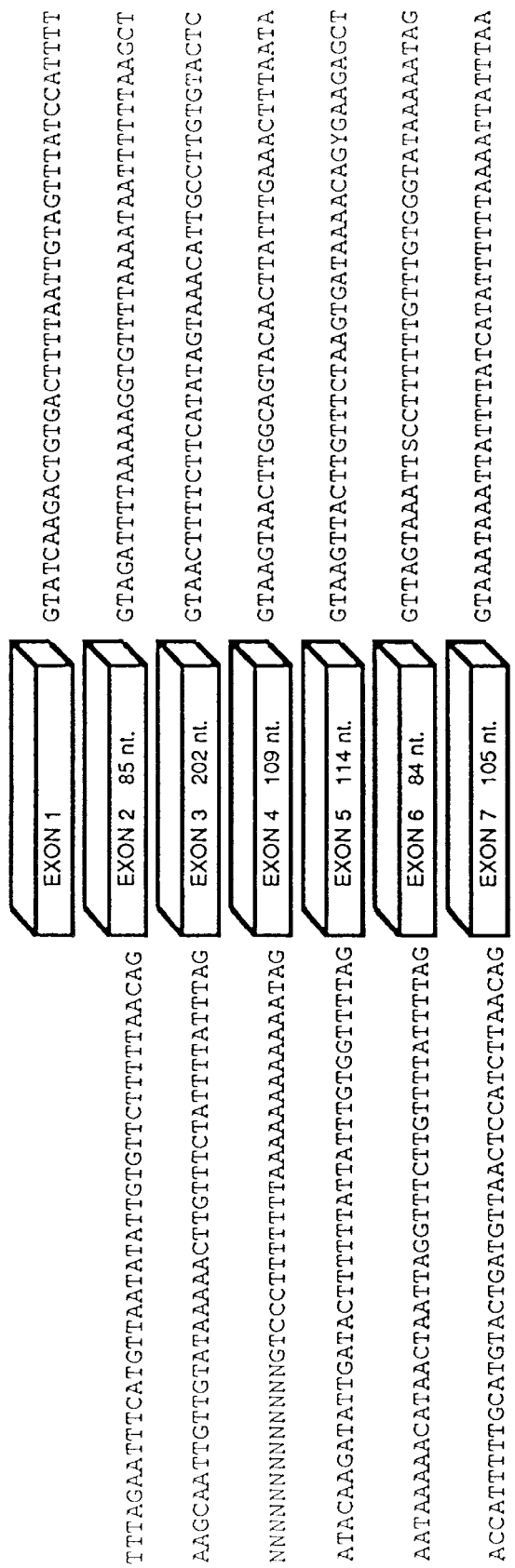
FIG. 1A shows an overview of yeast artificial chromosome (YAC) contigs. Genetic distances between selected RFLP markers from within the contigs are shown in centiMorgans.
Figures 2, 8B:
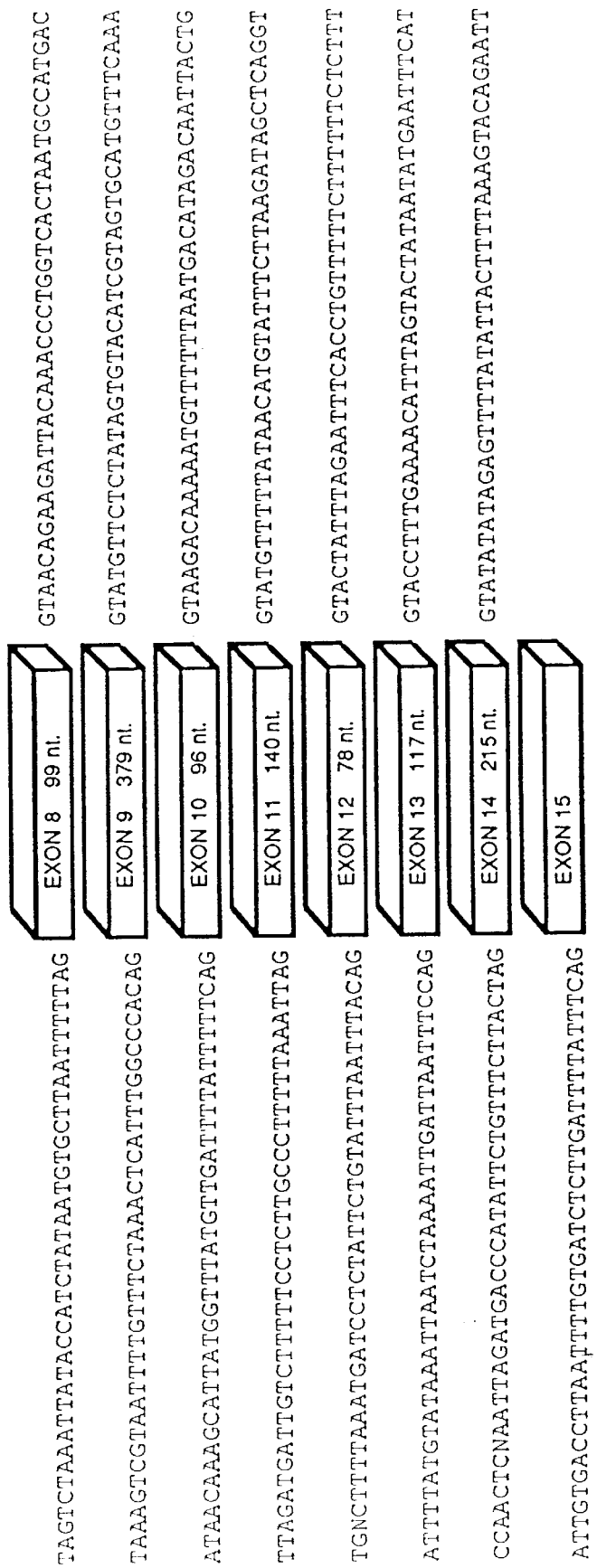
FIGS. 2A & B shows the sequence of TB1 and TB2 genes (SEQ ID NOs: 5 and 4, respectively). The cDNA sequence of the TB1 gene was determined from the analysis of 11 cDNA clones derived from normal colon and liver, as described in the text. A total of 2314 bp were contained within the overlapping cDNA clones, defining an ORF of 424 amino acids beginning at nucleotide 1. Only the predicted amino acids from the ORF are shown. The carboxy-terminal end of the ORF has apparently been identified, but the 5' end of the TB1 transcript has not yet been precisely determined.

FIG. 8 shows the arrangement of exons in DP2.5 (APC). (A) Exon 9 corresponds to nucleotides 933–1312; exon 9a corresponds to nucleotides 1236–1312. The stop codon in the cDNA is at nucleotide 8535. (B) Partial intronic sequence surrounding each exon is shown.

DETAILED DESCRIPTION

It is a discovery of the present invention that mutational events associated with tumorigenesis occur in a previously unknown gene on chromosome 5q named here the APC (Adenomatous Polyposis Coli) gene. Although it was previously known that deletion of alleles on chromosome 5q were common in certain types of cancers, it was not known that a target gene of these deletions was the APC gene. Further it was not known that other types of mutational events in the APC gene are also associated with cancers. The mutations of the APC gene can involve gross rearrangements, such as insertions and deletions. Point mutations have also been observed.

According to the diagnostic and prognostic method of the present invention, alteration of the wild-type APC gene is detected. "Alteration of a wild-type gene" according to the present invention encompasses all forms of mutations—including deletions. The alteration may be due to either rearrangements such as insertions, inversions, and deletions, or to point mutations. Deletions may be of the entire gene or only a portion of the gene. Somatic mutations are those which occur only in certain tissues, e.g., in the tumor tissue, and are not inherited in the germline. Germline mutations can be found in any of a body's tissues. If only a single allele is somatically mutated, an early neoplastic state is indicated. However, if both alleles are mutated then a late neoplastic state is indicated. The finding of APC mutations thus provides both diagnostic and prognostic information. An APC allele which is not deleted (e.g., that on the sister chromosome to a chromosome carrying an APC deletion) can be screened for other mutations, such as insertions, small deletions, and point mutations. It is believed that many mutations found in tumor tissues will be those leading to decreased expression of the APC gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to loss of expression of the APC gene product.

In order to detect the alteration of the wild-type APC gene in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These as well as other techniques for separating tumor from normal cells are well known in the art. If the tumor tissue is highly contaminated with normal cells, detection of mutations is more difficult.

Detection of point mutations may be accomplished by molecular cloning of the APC allele (or alleles) and sequencing that allele(s) using techniques well known in the art. Alternatively, the polymerase chain reaction (PCR) can be used to amplify gene sequences directly from a genomic DNA preparation from the tumor tissue. The DNA sequence of the amplified sequences can then be determined. The polymerase chain reaction itself is well known in the art. See, e.g., Saiki et al., Science, Vol. 239, p. 487, 1988; U.S. Pat. Nos. 4,683,203; and 4,683,195. Specific primers which can be used in order to amplify the gene will be discussed in more detail below. The ligase chain reaction, which is known in the art, can also be used to amplify APC sequences. See Wu et al., *Genomics,* Vol. 4, pp. 560–569 (1989). In addition, a technique known as allele specific PCR can be used. (See Ruano and Kidd, Nucleic Acids Research, Vol. 17, p. 8392, 1989.) According to this technique, primers are used which hybridize at their 3' ends to a particular APC mutation. If the particular APC mutation is not present, an amplification product is not observed. Amplification Refractory Mutation System (ARMS) can also be used as disclosed in European Patent Application Publication No. 0332435 and in Newton et al., Nucleic Acids Research, Vol. 17, p.7, 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening among kindred persons of an affected individual for the presence of the APC mutation found in that individual. Single stranded conformation polymorphism (SSCP) analysis can also be used to detect base change variants of an allele. (Orita et al., Proc. Natl. Acad. Sci. USA Vol. 86, pp. 2766–2770, 1989, and Genomics, Vol. 5, pp. 874–879, 1989.) Other techniques for detecting insertions and deletions as are known in the art can be used.

Alteration of wild-type genes can also be detected on the basis of the alteration of a wild-type expression product of the gene. Such expression products include both the APC mRNA as well as the APC protein product. The sequences of these products are shown in FIGS. 3 and 7. Point mutations may be detected by amplifying and sequencing the mRNA or via molecular cloning of cDNA made from the mRNA. The sequence of the cloned cDNA can be determined using DNA sequencing techniques which are well known in the art. The cDNA can also be sequenced via the polymerase chain reaction (PCR) which will be discussed in more detail below.

Mismatches, according to the present invention are hybridized nucleic acid duplexes which are not 100% homologous. The lack of total homology may be due to deletions, insertions, inversions, substitutions or frameshift mutations. Mismatch detection can be used to detect point mutations in the gene or its mRNA product. While these techniques are less sensitive than sequencing, they are simpler to perform on a large number of tumor samples. An example of a mismatch cleavage technique is the RNase protection method, which is described in detail in Winter et al., Proc. Natl. Acad. Sci. USA, Vol. 82, p. 7575, 1985 and Meyers et al., Science, Vol. 230, p. 1242, 1985. In the practice of the present invention the method involves the use of a labeled riboprobe which is complementary to the human wild-type APC gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of. the APC mRNA or gene but can be a segment of either. If the riboprobe comprises only a segment of the APC mRNA or gene it will be desirable to use a number of these probes to screen the whole mRNA sequence for mismatches.

In similar fashion, DNA probes can be used to detect mismatches, through enzymatic or chemical cleavage. See, e.g., Cotton et al., Proc. Natl. Acad. Sci. USA, Vol. 85, 4397, 1988; and Shenk et al., Proc. Natl. Acad. Sci. USA, Vol. 72, p. 989, 1975. Alternatively, mismatches can be detected by shifts in the electrophoretic mobility of mismatched duplexes relative to matched duplexes. See, e.g., Cariello, Human Genetics, Vol. 42, p. 726, 1988. With either riboprobes or DNA probes, the cellular mRNA or DNA which might contain a mutation can be amplified using PCR (see below) before hybridization. Changes in DNA of the APC gene can also be detected using Southern hybridization, especially if the changes are gross rearrangements, such as deletions and insertions.

DNA sequences of the APC gene which have been amplified by use of polymerase chain reaction may also be screened using allele-specific probes. These probes are nucleic acid oligomers, each of which contains a region of the APC gene sequence harboring a known mutation. For example, one oligomer may be about 30 nucleotides in length, corresponding to a portion of the APC gene sequence. By use of a battery of such allele-specific probes, PCR amplification products can be screened to identify the presence of a previously identified mutation in the APC gene. Hybridization of allele-specific probes with amplified APC sequences can be performed, for example, on a nylon filter. Hybridization to a particular probe under stringent hybridization conditions indicates the presence of the same mutation in the tumor tissue as in the allele-specific probe.

Alteration of APC mRNA expression can be detected by any technique known in the art. These include Northern blot analysis, PCR amplification and RNase protection. Diminished mRNA expression indicates an alteration of the wild-type APC gene.

Alteration of wild-type APC genes can also be detected by screening for alteration of wild-type APC protein. For example, monoclonal antibodies immunoreactive with APC can be used to screen a tissue. Lack of cognate antigen would indicate an APC mutation. Antibodies specific for products of mutant alleles could also be used to detect mutant APC gene product. Such immunological assays can be done in any convenient format known in the art. These include Western blots, immunohistochemical assays and ELISA assays. Any means for detecting an altered APC protein can be used to detect alteration of wild-type APC genes. Functional assays can be used, such as protein binding determinations. For example, it is believed that APC protein oligomerizes to itself and/or MCC protein or binds to a G protein. Thus, an assay for the ability to bind to wild type APC or MCC protein or that G protein can be employed. In addition, assays can be used which detect APC biochemical function. It is believed that APC is involved in phospholipid metabolism. Thus, assaying the enzymatic products of the involved phospholipid metabolic pathway can be used to determine APC activity. Finding a mutant APC gene product indicates alteration of a wild-type APC gene.

Mutant APC genes or gene products can also be detected in other human body samples, such as, serum, stool, urine and sputum. The same techniques discussed above for detection of mutant APC genes or gene products in tissues can be applied to other body samples. Cancer cells are sloughed off from tumors and appear in such body samples. In addition, the APC gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant APC genes or gene products.

The methods of diagnosis of the present invention are applicable to any tumor in which APC has a role in tumorigenesis. Deletions of chromosome arm 5q have been observed in tumors of lung, breast, colon, rectum, bladder, liver, sarcomas, stomach and prostate, as well as in leukemias and lymphomas. Thus these are likely to be tumors in which APC has a role. The diagnostic method of the present invention is useful for clinicians so that they can decide upon an appropriate course of treatment. For example, a tumor displaying alteration of both APC alleles might suggest a more aggressive therapeutic regimen than a tumor displaying alteration of only one APC allele.

The primer pairs of the present invention are useful for determination of the nucleotide sequence of a particular APC allele using the polymerase chain reaction. The pairs of single stranded DNA primers can be annealed to sequences within or surrounding the APC gene on chromosome 5q in order to prime amplifying DNA synthesis of the APC gene itself. A complete set of these primers allows synthesis of all of the nucleotides of the APC gene coding sequences, i.e., the exons. The set of primers preferably allows synthesis of both intron and exon sequences. Allele specific primers can also be used. Such primers anneal only to particular APC mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from APC sequences or sequences adjacent to APC except the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of the APC open reading frame shown in FIG. 7, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the APC gene or mRNA using other techniques. Mismatches can be detected using either enzymes (e.g., S1 nuclease), chemicals (e.g., hydroxylamine or osmium tetroxide and piperidine), or changes in electrophoretic mobility of mismatched hybrids as compared to totally matched hybrids. These techniques are known in the art. See, Cotton, supra, Shenk, supra, Myers, supra, Winter, supra, and Novack et al., Proc. Natl. Acad. Sci. USA, Vol. 83, p. 586, 1986. Generally, the probes are complementary to APC gene coding sequences, although probes to certain introns are also contemplated. An entire battery of nucleic acid probes is used to compose a kit for detecting alteration of wild-type APC genes. The kit allows for hybridization to the entire APC gene. The probes may overlap with each other or be contiguous.

If a riboprobe is used to detect mismatches with mRNA, it is complementary to the mRNA of the human wild-type APC gene. The riboprobe thus is an anti-sense probe in that it does not code for the APC protein because it is of the opposite polarity to the sense strand. The riboprobe generally will be labeled with a radioactive, calorimetric, or fluorometric material, which can be accomplished by any means known in the art. If the riboprobe is used to detect mismatches with DNA it can be of either polarity, sense or anti-sense. Similarly, DNA probes also may be used to detect mismatches.

Nucleic acid probes may also be complementary to mutant alleles of the APC gene. These are useful to detect similar mutations in other patients on the basis of hybridization rather than mismatches. These are discussed above and referred to as allele-specific probes. As mentioned above, the APC probes can also be used in Southern hybridizations to genomic DNA to detect gross chromosomal changes such as deletions and insertions. The probes can also be used to select cDNA clones of APC genes from tumor and normal tissues. In addition, the probes can be used to detect APC mRNA in tissues to determine if expression is diminished as a result of alteration of wild-type APC genes. Provided with the APC coding sequence shown in FIG. 7 (SEQ ID NO:1), design of particular probes is well within the skill of the ordinary artisan.

According to the present invention a method is also provided of supplying wild-type APC function to a cell which carries mutant APC alleles. Supplying such function should suppress neoplastic growth of the recipient cells. The wild-type APC gene or a part of the gene may be introduced into the cell in a vector such that the gene remains extrachromosomal. In such a situation the gene will be expressed by the cell from the extrachromosomal location. If a gene portion is introduced and expressed in a cell carrying a mutant APC allele, the gene portion should encode a part of the APC protein which is required for non-neoplastic growth of the cell. More preferred is the situation where the wild-type APC gene or a part of it is introduced into the mutant cell in such a way that it recombines with the endogenous mutant APC gene present in the cell. Such recombination requires a double recombination event which results in the correction of the APC gene mutation. Vectors for introduction of genes both for recombination and for extrachromosomal maintenance are known in the art and any suitable vector may be used. Methods for introducing DNA into cells such as electroporation, calcium phosphate co-precipitation and viral transduction are known in the art and the choice of method is within the competence of the routineer. Cells transformed with the wild-type APC gene can be used as model systems to study cancer remission and drug treatments which promote such remission.

Similarly, cells and animals which carry a mutant APC allele can be used as model systems to study and test for substances which have potential as therapeutic agents. The cells are typically cultured epithelial cells. These may be isolated from individuals with APC mutations, either somatic or germline. Alternatively, the cell line can be engineered to carry the mutation in the APC allele. After a test substance is applied to the cells, the neoplastically transformed phenotype of the cell will be determined. Any trait of neoplastically trans-formed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant APC alleles, usually from a second animal species, as well as insertion of disrupted homologous genes. Alternatively, the endogenous APC gene(s) of the animals may be disrupted by insertion or deletion mutation. After test substances have been administered to the animals, the growth of tumors must be assessed. If the test substance prevents or suppresses the growth of tumors, then the test substance is a candidate therapeutic agent for the treatment of FAP and/or sporadic cancers.

Polypeptides which have APC activity can be supplied to cells which carry mutant or missing APC alleles. The sequence of the APC protein is disclosed in FIG. 3 or 7 (SEQ ID NO: 2 or 7). These two sequences differ slightly and appear to be indicate the existence of two different forms of the APC protein. Protein can be produced by expression of the cDNA sequence in bacteria, for example, using known expression vectors. Alternatively, APC can be extracted from APC-producing mammalian cells such as brain cells. In addition, the techniques of synthetic chemistry can be employed to synthesize APC protein. Any of such techniques can provide the preparation of the present invention which comprises the APC protein. The preparation is substantially free of other human proteins. This is most readily accomplished by synthesis in a microorganism or in vitro.

Active APC molecules can be introduced into cells by microinjection or by use of liposomes, for example. Alternatively, some such active molecules may be taken up by cells, actively or by diffusion. Extracellular application of APC gene product may be sufficient to affect tumor growth. Supply of molecules with APC activity should lead to a partial reversal of the neoplastic state. Other molecules with APC activity may also be used to effect such a reversal, for example peptides, drugs, or organic compounds.

The present invention also provides a preparation of antibodies immunoreactive with a human APC protein. The antibodies may be polyclonal or monoclonal and may be raised against native APC protein, APC fusion proteins, or mutant APC proteins. The antibodies should be immunoreactive with APC epitopes, preferably epitopes not present on other human proteins. In a preferred embodiment of the invention the antibodies will immunoprecipitate APC proteins from solution as well as react with APC protein on Western or immunoblots of polyacrylamide gels. In another preferred embodiment, the antibodies will detect APC proteins in paraffin or frozen tissue sections, using immunocytochemical techniques. Techniques for raising and purifying antibodies are well known in the art and any such techniques may be chosen to achieve the preparation of the invention.

Predisposition to cancers as in FAP and GS can be ascertained by testing any tissue of a human for mutations of the APC gene. For example, a person who has inherited a germline APC mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells, or amniotic fluid for mutations of the APC gene. Alteration of a wild-type APC allele, whether for example, by point mutation or by deletion, can be detected by any of the means discussed above.

Molecules of cDNA according to the present invention are intron-free, APC gene coding molecules. They can be made by reverse transcriptase using the APC mRNA as a template. These molecules can be propagated in vectors and cell lines as is known in the art. Such molecules have the sequence shown in SEQ ID NO: 7. The cDNA can also be made using the techniques of synthetic chemistry given the sequence disclosed herein.

A short region of homology has been identified between APC and the human m3 muscarinic acetylcholine receptor (mAChR). This homology was largely confined to 29 residues in which 6 out of 7 amino acids (EL(GorA)GLQA) were identical (See FIG. 4). Initially, it was not known whether this homology was significant, because many other proteins had higher levels of global homology (though few had six out of seven contiguous amino acids in common). However, a study on the sequence elements controlling G protein activation by mAChR subtypes (Lechleiter et al., EMBO J., p. 4381 (1990)) has shown that a 21 amino acid region from the m3 mAChR completely mediated G protein specificity when substituted for the 21 amino acids of m2 mAChR at the analogous protein position. These 21 residues overlap the 19 amino acid homology between APC and m3 mAChR.

This connection between APC and the G protein activating region of mAChR is intriguing in light of previous investigations relating G proteins to cancer. For example, the RAS oncogenes, which are often mutated in colorectal cancers (Vogelstein, et al., N. Engl. J. Med., Vol. 319, p. 525 (1988); Bos et al., Nature Vol. 327, p. 293 (1987)), are members of the G protein family (Bourne, et al., Nature, Vol. 348, p. 125 (1990)) as is an in vitro transformation suppressor (Noda et al., Proc. Natl. Acad. Sci. USA, Vol. 86, p. 162 (1989)) and genes mutated in hormone producing tumors (Candis et al., Nature, Vol. 340, p. 692 (1989); Lyons et al., Science, Vol. 249, p. 655 (1990)). Additionally, the gene responsible for neurofibromatosis (presumably a tumor suppressor gene) has been shown to activate the GTPase activity of RAS (Xu et al., Cell, Vol. 63, p. 835 (1990); Martin et al., Cell, Vol. 63, p. 843 (1990); Ballester et al., Cell, Vol. 63, p. 851 (1990)). Another interesting link between G proteins and colon cancer involves the drug sulindac. This agent has been shown to inhibit the growth of benign colon tumors in patients with FAP, presumably by virtue of its activity as a cyclooxygenase inhibitor (Waddell et al., J. Surg. Oncology 24(1), 83 (1983); Wadell, et al., Am. J. Surg.,157(1), 175 (1989); Charneau et al., Gastroenterologie Clinique at Biologique 14(2), 153 (1990)). Cyclooxygenase is required to convert arachidonic acid to prostaglandins and other biologically active molecules. G proteins are known to regulate phospholipase A2 activity, which generates arachidonic acid from phospholipids (Role et al., Proc. Natl. Acad. Sci. USA, Vol. 84, p. 3623 (1987); Kurachi et al., Nature, Vol. 337, 12 555 (1989)). Therefore we propose that wild-type APC protein functions by interacting with a G protein and is involved in phospholipid metabolism.

The following are provided for exemplification purposes only and are not intended to limit the scope of the invention which has been described in broad terms above.

EXAMPLE 1

This example demonstrates the isolation of a 5.5 Mb region of human DNA linked to the FAP locus. Six genes are identified in this region, all of which are expressed in. normal colon cells and in colorectal, lung, ad bladder tumors.

The cosmid markers YN5.64 and YN5.48 have previously been shown to delimit an 8 cM region containing the locus for FAP (Nakamura et al., Am. J. Hum. Genet. Vol. 43, p. 638 (1988)). Further linkage and pulse-field gel electrophoresis (PFGE) analysis with additional markers has shown that the FAP locus is contained within a 4 cM region bordered by cosmids EF5.44 and L5.99. In order to isolate clones representing a significant portion of this locus, a yeast artificial chromosome (YAC) library was screened with various 5q21 markers. Twenty-one YAC clones, distributed within six contigs and including 5.5 Mb from the region between YN5.64 and YN5.48, were obtained (FIG. 1A).

Three contigs encompassing approximately 4 Mb were contained within the central portion of this region. The YAC's constituting these contigs, together with the markers used for their isolation and orientations, are shown in FIG. 1. These YAC contigs were obtained in the following way. To initiate each contig, the sequence of a genomic marker cloned from chromosome 5q21 was determined and used to design primers for PCR. PCR was then carried out on pools of YAC clones distributed in microtiter trays as previously described (Anand et al., Nucleic Acids Research, Vol. 18, p. 1951 (1980)). Individual YAC clones from the positive pools were identified by further PCR or hybridization based assays, and the YAC sizes were determined by PFGE.

To extend the areas covered by the original YAC clones, "chromosomal walking" was performed. For this purpose, YAC termini were isolated by a PCR based method and sequenced (Riley et al., Nucleic Acids Research, Vol. 18, p. 2887 (1990)). PCR primers based on these sequences were then used to rescreen the YAC library. For example, the sequence from an intron of the FER gene (Hao et al., Mol. Cell. Biol., Vol. 9, p. 1587 (1989)) was used to design PCR primers for isolation of the 28EC1 and 5EH8 YACs. The termini of the 28EC1 YAC were sequenced to derive markers RHE28 and LHE28, respectively. The sequences of these two markers were then used to isolate YAC clones 15CH12 (from RHE28) and 40CF1 and 29EF1 (from LHE28). These five YAC's formed a contig encompassing 1200 kb (contig 1, FIG. 1B).

Similarly, contig 2 was initiated using cosmid N5.66 sequences, and contig 3 was initiated using sequences both from the MCC gene and from cosmid EF5.44. A walk in the telomeric direction from YAC 14FH1 and a walk in the opposite direction from YAC 39GG3 allowed connection of the initial contig 3 clones through YAC 37HG4 (FIG. 1B).

Multipoint linkage analysis with the various markers used to define the contigs, combined with PFGE analysis, showed that contigs 1 and 2 were centromeric to contig 3. These contigs were used as tools to orient and/or identify genes which might be responsible for FAP. Six genes were found to lie within this cluster of YAC's , as follows:

Contig #1: FER—The FER gene was discovered through its homology to the viral oncogene ABL (Hao et al., supra). It has an intrinsic tyrosine kinase activity, and in situ hybridization with an FER probe showed that the gene was located at 5q11–23 (Morris et al., Cytogenet. Cell. Genet., Vol. 53, p. 4, (1990)). Because of the potential role of this oncogene-related gene in neoplasia, we decided to evaluate it further with regards to the FAP locus. A human genomic clone from FER was isolated (MF 2.3) and used to define a restriction fragment length polymorphism (RFLP), and the RFLP in turn used to map FER by linkage analysis using a panel of three generation families. This showed that FER was very tightly linked to previously defined polymorphic markers for the FAP locus. The genetic mapping of FER was complemented by physical mapping using the YAC clones derived from FER sequences (FIG. 1B). Analysis of YAC contig 1 showed that FER was within 600 kb of cosmid marker M5.28, which maps to within 1.5 Mb of cosmid L5.99 by PFGE of human genomic DNA. Thus, the YAC mapping results were consistent with the FER linkage data and PFGE analyses.

Contig 2: TB1—TB1 was identified through a cross-hybridization approach. Exons of genes are often evolutionarily conserved while introns and intergenic regions are much less conserved. Thus, if a human probe cross-hybridizes strongly to the DNA from non-primate species, there is a reasonable chance that it contains exon sequences. Subclones of the cosmids shown in FIG. 1 were used to screen Southern blots containing rodent DNA samples. A subclone of cosmid N5.66 (p 5.66–4) was shown to strongly hybridize to rodent DNA, and this clone was used to screen cDNA libraries derived from normal adult colon and fetal liver. The ends of the initial cDNA clones obtained in this screen were then used to extend the cDNA sequence. Eventually, 11 cDNA clones were isolated, covering 2314 bp. The gene detected by these clones was named TB1. Sequence analysis of the overlapping clones revealed an open reading frame (ORF) that extended for 1302 bp starting from the most 5' sequence data obtained (FIG. 2A). If this entire open reading frame were translated, it would encode 434 amino acids. The product of this gene was not globally homologous to any other sequence in the current database but showed two significant local similarities to a family of ADP, ATP carrier/translocator proteins and mitochondrial brown fat uncoupling proteins which are widely distributed from yeast to mammals. These conserved regions of TB1 (underlined in FIG. 2A) may define a predictive motif for this sequence family. In addition, TB1 appeared to contain a signal peptide (or mitochondrial targeting sequence) as well as at least 7 transmembrane domains.

Contig 3: MCC, TB2, SRP and APC—The MCC gene was also discovered through a cross-hybridization approach, as described previously (Kinzler et al., Science Vol. 251, p. 1366 (1991)). The MCC gene was considered a candidate for causing FAP by virtue of its tight genetic linkage to FAP susceptibility and its somatic mutation in sporadic colorectal carcinomas. However, mapping experiments suggested that the coding region of MCC was approximately 50 kb proximal to the centromeric end of a 200 kb deletion found in an FAP patient. MCC cDNA probes detected a 10 kb mRNA transcript on Northern blot analysis of which 4151 bp, including the entire open reading frame, have been cloned. Although the 3' non-translated portion or an alternatively spliced form of MCC might have extended into this deletion, it was possible that the deletion did not affect the MCC gene product. We therefore used MCC sequences to initiate a YAC contig, and subsequently used the YAC clones to identify genes 50 to 250 kb distal to MCC that might be contained within the deletion.

In a first approach, the insert from YAC24ED6 (FIG. 1B) was radiolabelled and hybridized to a cDNA library from normal colon. One of the eDNA clones (YS39) identified in this manner detected a 3.1 kb mRNA transcript when used as a probe for Northern blot hybridization. Sequence analysis of the YS39 clone revealed that it encompassed 2283 nucleotides and contained an ORF that extended for 555 bp from the most 5' sequence data obtained. If all of this ORF were translated, it would encode 185 amino acids (FIG. 2B). The gene detected by YS39 was named TB2. Searches of nucleotide and protein databases revealed that the TB2 gene was not identical to any previously reported sequences nor were there any striking similarities.

Another clone (YS11) identified through the YAC 24ED6 screen appeared to contain portions of two distinct genes. Sequences from one end of YS11 were identical to at least 180 bp of the signal recognition particle protein SRP19 (Lingelbach et al. Nucleic Acids Research, Vol. 16, p. 9431 (1988). A second ORF, from the opposite end of clone YS11, proved to be identical to 78 bp of a novel gene which was independently identified through a second YAC-based approach. For the latter, DNA from yeast cells containing YAC 14FH1 (FIG. 1B) was digested with EcoRI and subcloned into a plasmid vector. Plasmids that contained human DNA fragments were selected by colony hybridization using total human DNA as a probe. These clones were then used to search for cross-hybridizing sequences as described above for TB1, and the cross-hybridizing clones were subsequently used to screen cDNA libraries. One of the cDNA clones discovered in this way (FH38) contained a long ORF (2496 bp), 78 bp of which were identical to the above-noted sequences in YS11. The ends of the FH38 cDNA clone were then used to initiate cDNA walking to extend the sequence. Eventually, 85 cDNA clones were isolated from normal colon, brain and liver cDNA libraries and found to encompass 8973 nucleotides of contiguous transcript. The gene corresponding to this transcript was named APC. When used as probes for Northern blot analysis, APC cDNA clones hybridized to a single transcript of approximately 9.5 kb, suggesting that the great majority of the gene product was represented in the cDNA clones obtained. Sequences from the 5' end of the APC gene were found in YAC 37HG4 but not in YAC 14FH1. However, the 3' end of the APC gene was found in 14FH1 as well as 37HG4. Analogously, the 5' end of the MCC coding region was found in YAC clones 19AA9 and 26GC3 but not 24ED6 or 14FH1, while the 3' end displayed the opposite pattern. Thus, MCC and APC transcription units pointed in opposite directions, with the direction of transcription going from centromeric to telomeric in the case of MCC, and telomeric to centromeric in the case of APC. PFGE analysis of YAC DNA digested with various restriction endonucleases showed that TB2 and SRP were between MCC and APC, and that the 3' ends of the coding regions of MCC and APC were separated by approximately 150 kb (FIG. 1B).

Sequence analysis of the APC cDNA clones revealed an open reading frame of 8,535 nucleotides. The 5' end of the ORF contained a methionine codon (codon 1) that was preceded by an in-frame stop codon 9 bp upstream, and the 3' end was followed by several in-frame stop codons. The protein produced by initiation at codon 1 would contain 2,842 amino acids (FIG. 3). The results of database searching with the APC gene product were quite complex due to the presence of large segments with locally biased amino acid compositions. In spite of this, APC could be roughly divided into two domains. The N-terminal 25% of the protein had a high content of leucine residues (12%) and showed local sequence similarities to myosins, various intermediate filament proteins (e.g., desmin, vimentin, neurofilaments) and Drosophila armadillo/human plakoglobin. The latter protein is a component of adhesive junctions (desmosomes) joining epithelial cells (Franke et al., Proc. Natl. Acad. Sci. U.S.A., Vol. 86, p. 4027 (1989); Perfer et al., Cell, Vol. 63, p. 1167 (1990)) The C-terminal 75% of APC (residues 731–2832) is 17% serine by composition with serine residues more or less uniformly distributed. This large domain also contains local concentrations of charged (mostly acidic) and proline residues. There was no indication of potential signal peptides, transmembrane regions, or nuclear targeting signals in APC, suggesting a cytoplasmic localization.

To detect short similarities to APC, a database search was performed using the PAM-40 matrix (Altschul. J. Mol. Bio., Vol. 219, p. 555 (1991). Potentially interesting matches to several proteins were found. The most suggestive of these involved the ral2 gene product of yeast, which is implicated in the regulation of ras activity (Fukul et al., Mol. Cell. Biol., Vol. 9, p. 5617 (1989)). Little is known about how ral2 might interact with ras but it is interesting to note the positively-charged character of this region in the context of the negatively-charged GAP interaction region of ras. A specific electrostatic interaction between ras and GAP-related proteins has been proposed.

Because of the proximity of the MCC and APC genes, and the fact that both are implicated in colorectal tumorigenesis, we searched for similarities between the two predicted proteins. Bourne has previously noted that MCC has the potential to form alpha helical coiled coils (Nature, Vol. 351, p. 188 (1991). Lupas and colleagues have recently developed a program for predicting coiled coil potential from primary sequence data (Science, Vol. 252, p. 1162 (1991) and we have used their program to analyze both MCC and APC. Analysis of MCC indicated a discontinuous pattern of coiled-coil domains separated by putative "hinge" or "spacer" regions similar to those seen in laminin and other intermediate filament proteins. Analysis of the APC sequence revealed two regions in the N-terminal domain which had strong coiled coil-forming potential, and these regions corresponded to those that showed local similarities with myosin and IF proteins on database searching. In addition, one other putative coiled coil region was identified in the central region of APC. The potential for both APC and MCC to form coiled coils is interesting in that such structures often mediate homo- and hetero-oligomerization.

Finally, it had previously been noted that MCC shared a short similarity with the region of the m3 muscarinic acetylcholine receptor (mAChR) known to regulate specificity of G-protein coupling. The APC gene also contained a local similarity to the region of the m3 mAChR that overlapped with the MCC similarity (FIG. 4B). Although the similarities to ral2 (FIG. 4A) and m3 mAChR (FIG. 4B) were not statistically significant, they were intriguing in light of previous observations relating G-proteins to neoplasia.

Each of the six genes described above was expressed in normal colon mucosa, as indicated by their representation in colon cDNA libraries. To study expression of the genes in neoplastic colorectal epithelium, we employed reverse transcription-polymerase chain reaction (PCR) assays. Primers based on the sequences of FER., TB1, TB2, MCC, and APC were each used to design primers for PCR performed with cDNA templates. Each of these genes was found to be expressed in normal colon, in each of ten cell lines derived from colorectal cancers, and in tumor cell lines derived from lung and bladder tumors. The ten colorectal cancer cell lines included eight from patients with sporadic CRC and two from patients with FAP.

EXAMPLE 2

This example demonstrates a genetic analysis of the role of the FER gene in FAP and sporadic colorectal cancers.

We considered FER as a candidate because of its proximity to the FAP locus as judged by physical and genetic criteria (see Example 1), and its homology to known tyrosine kinases with oncogenic potential. Primers were designed to PCR-amplify the complete coding sequence of FER from the RNA of two colorectal cancer cell lines derived from FAP patients. cDNA was generated from RNA and used as a template for PCR. The primers used were 5'-AGAAGGATCCCTTGTGCAGTGTGGA-3' (SEQ ID NO: 95) and 5'-GACAGGATCCTGAAGCTGAGTTTG-3' (SEQ ID NO: 96). The underlined nucleotides were altered from the true FER sequence to create BamHI sites. The cell lines used were JW and Difi, both derived from colorectal cancers of FAP patients. (C. Paraskeva, B. G. Buckle, D. Sheer, C. B. Wigley, Int. J. Cancer 34, 49 (1984); M. E. Gross et al., Cancer Res. 51, 1452 (1991). The resultant 2554 basepair fragments were cloned and sequenced in their entirety. The PCR products were cloned in the BamHI site of Bluescript SK (Stratagene) and pools of at least 50 clones were sequenced en masse using T7 polymerase, as described in Nigro et al., Nature 342, 705 (1989).

Only a single conservative amino acid change (GTG-fCTG, creating a val to leu substitution at codon 439) was observed. The region surrounding this codon was then amplified from the DNA of individuals without FAP and this substitution was found to be a common polymorphism, not specifically associated with FAP. Based on these results, we considered it unlikely (though still possible) the FER gene was responsible for FAP. To amplify the regions surrounding codon 439, the following primers were used: 5'-TCAGAAAGTGCTGAAGAG-3' (SEQ ID NO: 97) and 5'-GGAATAATTAGGTCTCCAA-3' (SEQ ID NO: 98). PCR products were digested with PstI, which yields a 50 bp fragment if codon 439 is leucine, but 26 and 24 bp fragments if it is valine. The primers used for sequencing were chosen from the FER cDNA sequence in Hao et al., supra.

EXAMPLE 3

This example demonstrates the genetic analysis of MCC, TB2, SRP and APC in FAP and sporadic colorectal tumors. Each of these genes is linked and encompassed by contig 3 (see FIG. 1).

Several lines of evidence suggested that this contig was of particular interest. First, at least three of the four genes in this contig were within the deleted region identified in two FAP patients. (See Example 5 infra.) Second, alleic deletions of chromosome 5q21 in sporadic cancers appeared to be centered in this region. (Ashton-Rickardt et al., Oncogene, in press; and Miki et al., Japn. J. Cancer Res., in press.) Some tumors exhibited loss of proximal RFLP markers (up to and potentially including the 5' end of MCC), but no loss of markers distal to MCC. Other tumors exhibited loss of markers distal to and perhaps including the 3' end of MCC, but no loss of sequences proximal to MCC. This suggested either that different ends of MCC were affected by loss in all such cases, or alternatively, that two genes (one proximal to and perhaps including MCC, the other distal to MCC) were separate targets of deletion. Third, clones from each of the six FAP region genes were used as probes on Southern blots containing tumor DNA from patients with sporadic CRC. Only two examples of somatic changes were observed in over 200 tumors studied: a rearrangement/deletion whose centromeric end was located within the MCC gene (Kinzler et al., supra) and an 800 bp insertion within the APC gene between nucleotides 4424 and 5584. Fourth, point mutations of MCC were observed in two tumors (Kinzler et al.) supra strongly suggesting that MCC was a target of mutation in at least some sporadic colorectal cancers.

Based on these results, we attempted to search for subtle alterations of contig 3 genes in patients with FAP. We chose to examine MCC and APC, rather than TB2 or SRP, because of the somatic mutations in MCC and APC noted above. To facilitate the identification of subtle alterations, the genomic sequences of MCC and APC exons were determined (see Table 1; SEQ ID NOs: 24–38). These sequences were used to design primers for PCR analysis of constitutional DNA from FAP patients.

We first amplified eight exons and surrounding introns of the MCC gene in affected individuals from 90 different FAP kindreds. The PCR products were analyzed by a ribonuclease (RNase) protein assay. In brief, the PCR products were hybridized to in vitro transcribed RNA probes representing the normal genomic sequences. The hybrids were digested with RNase A, which can cleave at single base pair mismatches within DNA-RNA hybrids, and the cleavage products were visualized following denaturing gel electrophoresis. Two separate RNase protection analyses were performed for each exon, one with the sense and one with the antisense strand. Under these conditions, approximately 40% of all mismatches are detectable. Although some amino acid variants of MCC were observed in FAP patients, all such variants were found in a small percentage of normal individuals. These variants were thus unlikely to be responsible for the inheritance of FAP.

We next examined three exons of the APC gene. The three exons examined included those containing nt 822–930, 931–1309, and the first 300 nt of the most distal exon (nt 1956–2256). PCR and RNase protection analysis were performed as described in Kinzler et al. supra, using the primers underlined in Table 1. The primers for nt 1956–2256 were 5'-GCAAATCCTAAGAGAGAACAA-3' (SEQ ID NO: 99) and 5'-GATGGCAAGCTTGAGCCAG-3' (SEQ ID NO: 100).

In 90 kindreds, the RNase protection method was used to screen for mutations and in an additional 13 kindreds, the PCR products were cloned and sequenced to search for mutations not detectable by RNase protection. PCR products were cloned into a Bluescript vector modified as described in T. A. Holton and M. W. Graham, Nucleic Acids Res. 19, 1156 (1991). A minimum of 100 clones were pooled and sequenced. Five variants were detected among the 103 kindreds analyzed. Cloning and subsequent DNA sequencing of the PCR product of patient P21 indicated a C to T transition in codon 413 that resulted in a change from arginine to cysteine. This amino acid variant was not observed in any of 200 DNA samples from individuals without FAP. Cloning and sequencing of the PCR product from patients P24 and P34, who demon- strated the same abnormal RNase protection pattern indicated that both had a C to T transition at codon 301 that resulted in a change from arginine (CGA) to a stop codon (TGA). This change was not present in 200 individuals without FAP. As this point mutation resulted in the predicted loss of the recognition site for the enzyme Taq 1, appropriate PCR products could be digested with Taq 1 to detect the mutation. This allowed us to determine that the stop codon co-segregated with disease phenotype in members of the family of P24. The inheritance of this change in affected members of the pedigree provides additional evidence for the importance of the mutation.

Cloning and sequencing of the PCR product from FAP patient P93 indicated a C to G transversion at codon 279, also resulting in a stop codon (change from TCA to TGA). This mutation was not present in 200 individuals without FAP. Finally, one additional mutation resulting in a serine (TCA) to stop codon (TGA) at codon 712 was detected in a single patient with FAP (patient P60).

The five germline mutations identified are summarized in Table IIA, as well as four others discussed in Example 9. In addition to these germline mutations, we identified several somatic mutations of MCC and APC in sporadic CRC's . Seventeen MCC exons were examined in 90 sporadic colorectal cancers by RNase protection analysis. In each case where an abnormal RNase protection pattern was observed, the corresponding PCR products were cloned and sequenced. This led to the identification of six point mutations (two described previously) (Kinzler et al., supra), each of which was not found in the germline of these patients (Table IIB). Four of the mutations resulted in amino acid substitutions and two resulted in the alteration of splice site consensus elements. Mutations at analogous splice site positions in other genes have been shown to alter RNA processing in vivo and in vitro.

Three exons of APC were also evaluated in sporadic tumors. Sixty tumors were screened by RNase protection, and an additional 98 tumors were evaluated by sequencing. The exons examined included nt 822–930, 931–1309, and 1406–1545 (Table I). A total of three mutations were identified, each of which proved to be somatic. Tumor T27 contained a somatic mutation of CGA (arginine) to TGA (stop codon) at codon 33. Tumor T135 contained a GT to GC change at a splice donor site. Tumor T34 contained a 5 bp insertion (CAGCC between codons 288 and 289) resulting in a stop at codon 291 due to a frameshift.

We serendipitously discovered one additional somatic mutation in a colorectal cancer. During our attempt to define the sequences and splice patterns of the MCC and APC gene products in colorectal epithelial cells, we cloned cDNA from the colorectal cancer cell line SW480. The amino acid sequence of the MCC gene from SW480 was identical to that previously found in clones from human brain. The sequence of APC in SW480 cells, however, differed significantly, in that a transition at codon 1338 resulted in a change from glutamine (CAG) to a stop codon (TAG). To determine if this mutation was somatic, we recovered DNA from archival paraffin blocks of the original surgical specimen (T201) from which the tumor cell line was derived 28 years ago.

DNA was purified from paraffin sections as described in S. E. Goelz, S. R. Hamilton, and B. Vogelstein. Biochem. Biophys. Res. Comm. 130, 118 (1985). PCR was performed as described in reference 24, using the primers 5'-GTTCCAGCAGTGTCACAG-3' (SEQ ID NO: 101) and 5'-GGGAGATTTCGCTCCTGA-3' (SEQ ID NO: 102). A PCR product containing codon 1338 was amplified from the archival DNA and used to show that the stop codon represented a somatic mutation present in the original primary tumor and in cell lines derived from the primary and metastatic tumor sites, but not from normal tissue of the patient.

The ten point mutations in the MCC and APC genes so far discovered in sporadic CRCs are summarized in Table IIB. Analysis of the number of mutant and wild-type PCR clones obtained from each of these tumors showed that in eight of the ten cases, the wild-type sequence was present in approximately equal proportions to the mutant. This was confirmed by RFLP analysis using flanking markers from chromosome 5q which demonstrated that only two of the ten tumors (T135 and T201) exhibited an allelic deletion on chromosome Sq. These results are consistent with previous observations showing that 20–40% of sporadic colorectal tumors had allelic deletions of chromosome Sq. Moreover, these data suggest that mutations of 5q21 genes are not limited to those colorectal tumors which contain allelic deletions of this chromosome.

EXAMPLE 4

This example characterizes small, nested deletions in DNA from two unrelated FAP patients.

DNA from 40 FAP patients was screened with cosmids that has been mapped into a region near the APC locus to identify small deletions or rearrangements. Two of these cosmids, L5.71 and L5.79, hybridized with a 1200 kb NotI fragment in DNAs from most of the FAP patients screened.

The DNA of one FAP patient, 3214, showed only a 940 kb NotI fragment instead of the expected 1200 kb fragment. DNA was analyzed from four other members of the patient's immediate family; the 940 kb fragment was present in her affected mother (4711), but not in the other, unaffected family members. The mother also carried a normal 1200 kb NotI fragment that was transmitted to her two unaffected offspring. These observations indicated that the mutant polyposis allele is on the same chromosome as the 940 kb NotI fragment. A simple interpretation is that APC patients 3214 and 4711 each carry a 260 kb deletion within the APC locus.

If a deletion were present, then other enzymes might also be expected to produce fragments with altered mobilities. Hybridization of L5.79 to NruI-digested DNAs from both affected members of the family revealed a novel NruI fragment of 1300 kb, in addition to the normal 1200 kb NruI fragment. Furthermore, MluI fragments in patients 3214 and 4711 also showed an increase in size consistent with the deletion of an MluI site. The two chromosome 5 homologs of patient 3214 were segregated in somatic cell hybrid lines; HHW1155 (deletion hybrid) carried the abnormal homolog and HHW1159 (normal hybrid) carried the normal homolog.

Because patient 3214 showed only a 940 kb NotI fragment, she had not inherited the 1200 kb fragment present in the unaffected father's DNA. This observation suggests that he must be heterozygous for, and have transmitted, either a deletion of the L5.79 probe region or a variant NotI fragment too large to resolve on the gel system. As expected, the hybrid cell line HHW1159, which carries the paternal homolog, revealed no resolved Not fragment when probed with L5.79. However, probing of HHW1159 DNA with L5.79 following digestion with other enzymes did reveal restriction fragments, demonstrating the presence of DNA homologous to the probe. The father is, therefore, interpreted as heterozygous for a polymorphism at the NotI site, with one chromosome 5 having a 1200 kb NotI fragment and the other having a fragment too large to resolve consistently on the gel. The latter was transmitted to patient 3214.

When double digests were used to order restriction sites within the 1200 kb NotI fragment, L5.71 and L5.79 were both found to lie on a 550 kb NotI-NruI fragment and, therefore, on the same side of an NruI site in the 1200 kb NotI fragment. To obtain genomic representation of sequences present over the entire 1200 kb NotI fragment, we constructed a library of small-fragment inserts enriched for sequences from this fragment. DNA from the somatic cell hybrid HHW141, which contains about 40% of chromosome 5, was digested with NotI and electrophoresed under pulsed-field gel (PFG) conditions; EcoRI fragments from the 1200 kb region of this gel were cloned into a phage vector. Probe Map30 was isolated from this library. In normal individuals probe Map30 hybridizes to the 1200 kb NotI fragment and to a 200 kb NruI fragment. This latter hybridization places Map30 distal, with respect to the locations of L5.71 and L5.79, to the NruI site of the 550 kb NotI-NruI fragment.

Because Map30 hybridized to the abnormal, 1300 kb NruI fragment of patient 3214, the locus defined by Map30 lies outside the hypothesized deletion. Furthermore, in normal chromosomes Map30 identified a 200 kb NruI fragment and L5.79 identified a 1200 kb NruI fragment; the hypothesized deletion must, therefore, be removing an NruI site, or sites, lying between Map30 and L5.79, and these two probes must flank the hypothesized deletion. A restriction map of the genomic region, showing placement of these probes, is shown in FIG. 5.

A NotI digest of DNA from another FAP patient, 3824, was probed with L5.79. In addition to the 1200 kb normal NotI fragment, a fragment of approximately 1100 kb was observed, consistent with the presence of a 100 kb deletion in one chromosome 5. In this case, however, digestion with NruI and MluI did not reveal abnormal bands, indicating that if a deletion were present, its boundaries must lie distal to the NruI and MluI sites of the fragments identified by L5.79. Consistent with this expectation, hybridization of Map30 to DNA from patient 3824 identified a 760 kb MluI fragment in addition to the expected 860 kb fragment, supporting the interpretation of a 100 kb deletion in this patient. The two chromosome 5 homologs of patient 3824 were segregated in somatic cell hybrid lines; HHW1291 was found to carry only the abnormal homolog and HHW1290 only the normal homolog.

That the 860 kb MluI fragment identified by Map30 is distinct from the 830 kb MluI fragment identified previously by L5.79 was demonstrated by hybridization of Map30 and L5.79 to a NotI-MluI double digest of DNA from the hybrid cell (HHW1159) containing the nondeleted chromosome 5 homolog of patient 3214. As previously indicated, this hybrid is interpreted as missing one of the NotI sites that define the 1200 kb fragment. A 620 kb NotI-MluI fragment was seen with probe L5.79, and an 860 kb fragment was seen with Map30. Therefore, the 830 kb MluI fragment recognized by probe L5.79 must contain a NotI site in HHW1159 DNA; because the 860 kb MluI fragment remains intact, it does not carry this NotI site and must be distinct from the 830 kb MluI fragment.

EXAMPLE 5

This example demonstrates the isolation of human sequences which span the region deleted in the two unrelated FAP patients characterized in Example 4.

A strong prediction of the hypothesis that patients 3214 and 3824 carry deletions is that some sequences present on normal chromosome 5 homologs would be missing from the hypothesized deletion homologs. Therefore, to develop genomic probes that might confirm the deletions, as well as to identify genes from the region, YAC clones from a contig seeded by cosmid L5.79 were localized from a library containing seven haploid human genome equivalents (Albertsen et al., Proc. Natl. Acad. Sci. U.S.A., Vol. 87, pp. 4256–4260 (1990)) with respect to the hypothesized deletions. Three clones, YACs 57B8, 310D8, and 183H12, were found to overlap the deleted region.

Importantly, one end of YAC 57B8 (clone AT57) was found to lie within the patient 3214 deletion. Inverse polymerase chain reaction (PCR) defined the end sequences of the insert of YAC 57B8. PCR primers based on one of these end sequences repeatedly failed to amplify DNA from the somatic cell hybrid (HHW1155) carrying the deleted homolog of patient 3214, but did amplify a product of the expected size from the somatic cell hybrid (HHW1159) carrying the normal chromosome 5 homolog. This result supported the interpretation that the abnormal restriction fragments found in the DNA of patient 3214 result from a deletion.

Additional support for the hypothesis of deletion in DNA from patient 3214 came from subcloned fragments of YAC 183H12, which spans the region in question. Y11, an EcoRI fragment cloned from YAC 183H12, hybridized to the normal, 1200 kb NotI fragment of patient 4711, but failed to hybridize to the abnormal, 940 kb NotI fragment of 4711 or to DNA from deletion cell line HHW1155. This result confirmed the deletion in patient 3214.

Two additional EcoRI fragments from YAC 183H12, Y10 and Y14, were localized within the patient 3214 deletion by their failure to hybridizie to DNA from HHW1155. Probe Y10 hybridizes to a 150 kb NruI fragment in normal chromosome 5 homologs. Because the 3214 deletion creates the 1300 kb NruI fragment seen with the probes L5.79 and Map30 that flank the deletion, these NruI sites and the 150 kb NruI fragment lying between must be deleted in patient 3214. Furthermore, probe Y10 hybridizes to the same 620 kb NotI-MluI fragment seen with probe L5.79 in normal DNA, indicating its location as L5.79-proximal to the deleted MluI site and placing it between the MluI site and the L5.79-proximal NruI site. The MluI site must, therefore, lie between the NruI sites that define the 150 kb NruI fragment (see FIG. 5).

Probe Y11 also hybridized to the 150 kb NruI fragment in the normal chromosome 5 homolog, but failed to hybridize to the 620 kb NotI-MluI fragment, placing it L5.79 distal to the MluI site, but proximal to the second NruI site. Hybridization to the same (860 kb) MluI fragment as Map30 confirmed the localization of probe Y11 L5.79-distal to the MluI site.

Probe Y14 was shown to be L5.79-distal to both deleted NruI sites by virtue of its hybridization to the same 200 kb NruI fragment of the normal chromosome 5 seen with Map30. Therefore, the order of these EcoRI fragments derived from YAC 183H12 and delected in patient 3214, with respect to L5.79 and Map30, is L5.79-Y10-Y11-Y14-Map30.

The 100 kb deletion of patient 3824 was confirmed by the failure of aberrant restriction fragments in this DNA to hybridize with probe Y11, combined with positive hybridizations to probes Y10 and/or Y14. Y10 and Y14 each hybridized to the 1100 kb NotI fragment of patient 3824 as well as to the normal 1200 kb NotI fragment, but Y11 hybridized to the 1200 kb fragment only. In the MluI digest, probe Y14 hybridized to the 860 kb and 760 kb fragments of patient 3824 DNA, but probe Y11 hybridized only to the 860 kb fragment. We conclude that the basis for the alteration in fragment size in DNA from patient 3824 is, indeed, a deletion. Furthermore, because probes Y10 and Y14 are missing from the deleted 3214 chromosome, but present on the deleted 3824 chromosome, and they have been shown to flank probe Y11, the deletion in patient 3824 must be nested within the patient 3214 deletion.

Probes Y10, Y11, Y14 and Map30 each hybridized to YAC 310D8, indicating that this YAC spanned the patient 3824 deletion and at a minimum, most of the 3214 deletion. The YAC characterizations, therefore, confirmed the presence of deletions in the patients and provided physical representation of the deleted region.

EXAMPLE 6

This example demonstrates that the MCC coding sequence maps outside of the region deleted in the two FAP patients characterized in Example 4.

An intriguing FAP candidate gene, MCC, recently was ascertained with cosmid L5.71 and was shown to have undergone mutation in colon carcinomas (kinzler et al., supra). It was therefore of interest to map this gene with respect to the deletions in APC patients. Hybridization of MCC probes with an overlapping series of YAC clones extending in either direction from L5.71 showed that the 3' end of MCC must be oriented toward the region of the two APC deletions.

Therefore, two 3' cDNA clones from MCC were mapped with respect to the deletions: clone 1CI (bp 2378–4181) and clone 7 (bp 2890–3560). Clone 1CI contains sequences from the C-terminal end of the open reading frame, which stops at nucleotide 2708, as well as 3' untranslated sequence. Clone 7 contains sequence that is entirely 3' to the open reading frame. Importantly, the entire 3' untranslated sequence contained in the EDNA clones consists of a single 2.5 kb exon. These two clones were hybridized to DNAs from the YACs spanning the FAP region. Clone 7 fails to hybridize to YAC 310D8, although it does hybridize to YACs 183H12 and 57B8; the same result was obtained with the cDNA 1CI. Furthermore, these probes did show hybridization to DNAs from both hybrid cell lines (HWW1159 and HWW1155) and the lymphoblastoid cell line from patient 3214, confirming their locations outside the deleted region. Additional mapping experiments suggested that the 3' end of the MCC cDNA clone contig is likely to be located more than 45 kb from the deletion of patient 3214 and, therefore, more than 100 kb from the deletion of patient 3824.

EXAMPLE 7

This example identifies three genes within the deleted region of chromosome 5 in the two unrelated FAP patients characterized in Example 4.

Genomic clones were used to screen cDNA libraries in three separate experiments. One screening was done with a phage clone derived from YAC 310D8 known to span the 260 kb deletion of patient 3214. A large-insert phage library was constructed from this YAC; screening with Y11 identified X205, which mapped within both deletions. When clone X205 was used to probe a random-, plus oligo(dT)-, primed fetal brain eDNA library (approximately 300,000 phage), six cDNA clones were isolated and each of them mapped entirely within both deletions. Sequence analysis of these six clones formed a single cDNA contig, but did not reveal an extended open reading frame. One of the six cDNAs was used to isolate more cDNA clones, some of which crossed the L5.71-proximal breakpoint of the 3824 deletion, as indicated by hybridization to both chromosome of this patient. These clones also contained an open reading frame, indicating a transcriptional orientation proximal to distal with respect to L5.71. This gene was named DP1 (deleted in polyposis 1). This gene is identical to TB2 described above.

cDNA walks yielded a eDNA contig of 3.0–3.5 kb, and included two clones containing terminal poly(A) sequences. This size corresponds to the 3.5 kb band seen by Northern analysis. Sequencing of the first 3163 bp of the cDNA contig revealed an open reading frame extending from the first base to nucleotide 631, followed by a 2.5 kb 3' untranslated region. The sequence surrounding the methionine codon at base 77 conforms to the Kozak consensus of an initiation methionine (Kozak, 1984). Failed attempts to walk farther, coupled with the similarity of the lengths of isolated cDNA and mRNA, suggested that the $NH_2$-terminus of the DP1 protein had been reached. Hybridization to a combination of genomic and YAC DNAs cut with various enzymes indicated the genomic coverage of DP1 to be approximately 30 kb.

Two additional probes for the locus, YS-11 and YS-39, which had been ascertained by screening of a cDNA library with an independent YAC probe identified with MCC sequences adjacent to L5.71, were mapped into the deletion region. YS-39 was shown to be a cDNA identical in sequence to DP1. Partial characterization of YS-11 had shown that 200 bp of DNA sequence at one end was identical to sequence coding for the 19 kd protein of the ribosomal signal recognition particle, SRP19 (Lingelbach et al., supra). Hybridization experiments mapped YS-11 within both deletions. The sequence of this clone, however, was found to be complex. Although 454 bp of the 1032 bp sequence of YS-11 were identical to the GenBank entry for the SRP19 gene, another 578 bp appended 5' to the SRP19 sequence was found to consist of previously unreported sequence containing no extended open reading frames. This suggested that YS-11 was either a chimeric clone containing two independent inserts or a clone of an incompletely processed or aberrant message. If YS-11 were a conventional chimeric clone, the independent segments would not be expected to map to the same physical region. The segments resulting from anomalous processing of a continuous transcript, however, would map to a single chromosomal region.

Inverse PCR with primers specific to the two ends of YS-11, the SRP19 end and the unidentified region, verified that both sequences map within the YAC 310D8; therefore, YS-11 is most likely a clone of an immature or anomalous mRNA species. Subsequently, both ends were shown to lie with the deleted region of patient 3824, and YS-11 was used to screen for additional cDNA clones.

Of the 14 cDNA clones selected from the fetal brain library, one clone, V5, was of particular interest in that it contained an open reading frame throughout, although it included only a short identity to the first 78 5' bases of the YS-11 sequence. Following the 78 bp of identical sequence, the two cDNA sequences diverged at an AG. Furthermore, divergence from genomic sequence was also seen after these 78 bp, suggesting the presence of a splice junction, and supporting the view that YS-11 represents an irregular message.

Starting with V5, successive 5' and 3' walks were performed; the resulting cDNA contig consisted of more than 100 clones, which defined a new transcript, DP2. Clones walking in the 5' direction crossed the 3824 deletion breakpoint farthest from L5.71; since its 3' end is closer to this cosmid than its 5' end, the transcriptional orientation of DP2 is opposite to that of MCC and DP1.

The third screening approach relied on hybridization with a 120 kb MluI fragment from YAC 57B8. This fragment hybridizes with probe Y11 and completely spans the 100 kb deletion in patient 3824. the fragment was purified on two preparative PFGs, labeled, and used to screen a fetal brain eDNA library. A number of eDNA clones previously identified in the development of the DP1 and DP2 contigs were reascertained. However, 19 new cDNA clones mapped into the patient 3824 deletion. Analysis indicated that these 19 formed a new contig, DP3, containing a large open reading frame.

A clone from the 5' end of this new cDNA contig hybridized to the same EcoRI fragment as the 3' end of DP2. Subsequently, the DP2 and DP3 contigs were connected by a single 5' walking step from DP3, to form the single contig DP2.5. The complete nucleotide sequence of DP2.5 is shown in FIG. 9.

The consensus cDNA sequence of DP2.5 suggests that the entire coding sequence of DP2.5 has been obtained and is 8532 bp long. The most 5' ATG codon occurs two codons from an in-frame stop and conforms to the Kozak initiation consensus (Kozak, Nucl. Acids. Res., Vol. 12, p. 857–872 1984). The 3' open reading frame breaks down over the final 1.8 kb, giving multiple stops in all frames. A poly(A) sequence was found in one clone approximately 1 kb into the 3' untranslated region, associated with a polyadenylation signal 33 bp upstream (position 9530). The open reading frame is almost identical to that identified as APC above.

An alternatively spliced exon at nucleotide 934 of the DP2.5 transcript is of potential interest. it was first discovered by noting that two classes of cDNA had been isolated. The more abundant cDNA class contains a 303 bp exon not included in the other. The presence in vivo of the two transcripts was verified by an exon connection experiment. Primers flanking the alternatively spliced exon were used to amplify, by PCR, cDNA prepared from various adult tissues. Two PCR products that differed in size by approximately 300 bases were amplified from all the tissues tested; the larger product was always more abundant than the smaller.

EXAMPLE 8

This example demonstrates the primers used to identify subtle mutations in DP1, SRP19, and DP25.

To obtain DNA sequence adjacent to the exons of the genes DP1, DP2.5, and SRP19, sequencing substrate was obtained by inverse PCR amplification of DNAs from two YACs, 310D8 and 183H12, that span the deletions. Ligation at low concentration cyclized the restriction enzyme-digested YAC DNAs. Oligonucleotides with sequencing tails, designed in inverse orientation at intervals along the cDNAs, primed PCR amplification from the cyclized templates. Comparison of these DNA sequences with the cDNA sequences placed exon boundaries at the divergence points. SRP19 and DP1 were each shown to have five exons. DP2.5 consisted of 15 exons. The sequences of the oligonucleotides synthesized to provide PCR amplification primers for the exons of each of these genes are listed in Table 111 (SEQ ID NO: 39–94). With the exception of exons 1, 3, 4, 9, and 15 of DP2.5 (see below), the primer sequences were located in intron sequences flanking the exons. The 5' primer of exon 1 is complementary to the cDNA sequence, but extends just into the 5' Kozak consensus sequence for the initiator methionine, allowing a survey of the translated sequences. The 5' primer of exon 3 is actually in the 5' coding sequences of this exon, as three separate intronic primers simply would not amplify. The 5' primer of exon 4 just overlaps the 5' end of this exon, and we thus fail to survey the 19 most 5' bases of this exon. For exon 9, two overlapping primer sets were used, such that each had one end within the exon. For exon 15, the large 3' exon of DP2.5, overlapping primer pairs were placed along the length of the exon; each pair amplified a product of 250–400 bases.

EXAMPLE 9

This example demonstrates the use of single stranded conformation polymorphism (SSCP) analysis as described by Orita et al. Proc. Natl. Acad. Sci. U.S.A., Vol. 86, pp. 2766–70 (1989) and Genomics, Vol. 5, pp. 874–879 (1989) as applied to DP1, SRP19 and DP2.5.

SSCP analysis identifies most single- or multiple-base changes in DNA fragments up to 400 bases in length. Sequence alterations are detected as shifts in electrophoretic mobility of single-stranded DNA on nondenaturing acrylamide gels; the two complementary strands of a DNA segment usually resolve as two SSCP conformers of distinct mobilities. However, if the sample is from an individual heterozygous for a base-pair variant within the amplified segment, often three or more bands are seen. In some cases, even the sample from a homozygous individual will show multiple bands. Base-pair-change variants are identified by differences in pattern among the DNAs of the sample set.

Exons of the candidate genes were amplified by PCR from the DNAs of 61 unrelated FAP patients and a control set of 12 normal individuals. The five exons from DP1 revealed no unique conformers in the FAP patients, although common conformers were observed with exons 2 and 3 in some individuals of both affected and control sets, indicating the presence of DNA sequence polymorphisms. Likewise, none of the five exons of SRP19 revealed unique conformers in DNA from FAP patients in the test panel.

Testing of exons 1 through 14 and primer sets A through N of exon 15 of the DP2.5 gene, however, revealed variant conformers specific to FAP patients in exons 7, 8, 10, 11, and 15. These variants were in the unrelated patients 3746, 3460, 3827, 3712, and 3751, respectively. The PCR-SSCP procedure was repeated for each of these exons in the five affected individuals and in an expanded set of 48 normal controls. The variant bands were reproducible in the FAP patients but were not observed in any of the control DNA samples. Additional variant conformers in exons 11 and 15 of the DP2.5 gene were seen; however, each of these was found in both the affected and control DNA sets. The five sets of conformers unique to the FAP patients were sequenced to determine the nucleotide changes responsible for their altered mobilities. The normal conformers from the host individuals were sequenced also. Bands were cut from the dried acrylamide gels, and the DNA was eluted. PCR amplification of these DNAs provided template for sequencing.

The sequences of the unique conformers from exons 7, 8, 10, and 11 of DP2.5 revealed dramatic mutations in the DP2.5 gene. The sequence of the new mutation creating the exon 7 conformer in patient 3746 was shown to contain a deletion of two adjacent nucleotides, at positions 730 and 731 in the cDNA sequence (FIG. 7). The normal sequence at this splice junction is CAGGGTCA (intronic sequence underlined), with the intron-exon boundary between the two repetitions of AG. The mutant allele in this patient has the sequence CAGGTCA. Although this change is at the 5' splice site, comparison with known consensus sequences of splice junctions would suggest that a functional splice junction is maintained. If this new splice junction were functional, the mutation would introduce a frameshift that creates a stop codon 15 nucleotides downstream. If the new splice junction were not functional, messenger processing would be significantly altered.

To confirm the 2-base deletion, the PCR product from FAP patient 3746 and a control DNA were electrophoresed on an acrylamide-urea denaturing gel, along with the products of a sequencing reaction. The sample from patient 3746 showed two bands differing in size by 2 nucleotides, with the larger band identical in mobility to the control sample; this result was independent confirmation that patient 3746 is heterozygous for a 2 bp deletion.

The unique conformer found in exon 8 of patient 3460 was found to carry a C-T transition, at position 904 in the cDNA sequence of DP2.5 (shown in FIG. 7), which replaced the normal sequence of CGA with TGA. This point mutation, when read in frame, results in a stop codon replacing the normal arginine codon. This single-base change had occurred within the context of a CG dimer, a potential hot spot for mutation (Barker et al., 1984).

The conformer unique to FAP patient 3827 in exon 10 was found to contain a deletion of one nucleotide (1367, 1368, or 1369) when compared to the normal sequence found in the other bands on the SSCP gel. This deletion, occurring within a set of three T's, changed the sequence from CTTTCA to CTTCA; this 1 base frameshift creates a downstream stop within 30 bases. The PCR product amplified from this patient's DNA also was electrophoresed on an acrylamide-urea denaturing gel, along with the PCR product from a control DNA and products from a sequencing reaction. The patient's PCR product showed two bands differing by 1 bp in length, with the larger identical in mobility to the PCR product from the normal DNA; this result confirmed the presence of a 1 bp deletion in patient 3827.

Sequence analysis of the variant conformer of exon 11 from patient 3712 revealed the substitution of a T by a G at position 1500, changing the normal tyrosine codon to a stop codon.

The pair of conformers observed in exon 15 of the DP2.5 gene for FAP patient 3751 also was sequenced. These conformers were found to carry a nucleotide substitution of C to G at position 5253, the third base of a valine codon. No amino acid change resulted from this substitution, suggesting that this conformer reflects a genetically silent polymorphism.

The observation of distinct inactivating mutations in the DP2.5 gene in four unrelated patients strongly suggested that DP2.5 is the gene involved in FAP. These mutations are summarized in Table IIA.

EXAMPLE 10

This example demonstrates that the mutations identified in the DP2.5 (APC) gene segregate with the FAP phenotype.

Patient 3746, described above as carrying an APC allele with a frameshift mutation, is an affected offspring of two normal parents. Colonoscopy revealed no polyps in either parent nor among the patient's three siblings.

DNA samples from both parents, from the patient's wife, and from their three children were examined. SSCP analysis of DNA from both of the patient's parents displayed the normal pattern of conformers for exon 7, as did DNA from the patients's wife and one of his offspring. The two other children, however, displayed the same new conformers as their affected father. Testing of the patient and his parents with highly polymorphic VNTR (variable number of tandem repeat) markers showed a 99.98% Likelihood that they are his biological parents.

These observations confirmed that this novel conformer, known to reflect a 2 bp deletion mutation in the DP2.5 gene, appeared spontaneously with FAP in this pedigree and was transmitted to two of the children of the affected individual.

EXAMPLE 11

This example demonstrates polymorphisms in the APC gene which appear to be unrelated to disease (FAP).

Sequencing of variant conformers found among controls as well as individuals with APC has revealed the following polymorphisms in the APC gene: first, in exon 11, at position 1458, a substitution of T to C creating an RsaI restriction site but no amino acid change; and second, in exon 15, at positions 5037 and 5271, substitutions of A to G and G to T, respectively, neither resulting in amino acid substitutions. These nucleotide polymorphisms in the APC gene sequence may be useful for diagnostic purposes.

EXAMPLE 12

This example shows the structure of the APC gene.

The structure of the APC gene is schematically shown in FIG. 8, with flanking intron sequences indicated.

The continuity of the very large (6.5 kb), most 3' exon in DP2.5 was shown in two ways. First, inverse PCR with primers spanning the entire length of this exon revealed no divergence of the cDNA sequence from the genomic sequence. Second, PCR amplification with converging primers placed at intervals along the exon generated products of the same size whether amplified from the originally isolated cDNA, cDNA from various tissues, or genomic template. Two forms of exon 9 were found in DP2.5: one is the complete exon; and the other, labeled exon 9A, is the result of a splice into the interior of the exon that deletes bases 934 to 1236 in the mRNA and removes 101 amino acids from the predicted protein (see FIG. 7).

EXAMPLE 13

This example demonstrates the mapping of the FAP deletions with respect to the APC exons.

Somatic cell hybrids carrying the segregated chromosomes 5 from the 100 kb (HHW1291) and 260 kb (HHW1155) deletion patients were used to determine the distribution of the APC genes exons across the deletions. DNAs from these cell lines were used as template, along with genomic DNA from a normal control, for PCR-based amplification of the APC exons.

PCR analysis of the hybrids from the 260 kb deletion of patient 3214 showed that all but one (exon 1) of the APC exons are removed by this deletion. PCR analysis of the somatic cell hybrid HHW1291, carrying the chromosome 5 homolog with the 100 kb deletion from patient 3824, revealed that exons 1 through 9 are present but exons 10 through 15 are missing. This result placed the deletion breakpoint either between exons 9 and 10 or within exon 10.

EXAMPLE 14

This example demonstrates the expression of alternately spliced APC messenger in normal tissues and in cancer cell lines.

Tissues that express the APC gene were identified by PCR amplification of cDNA made to mRNA with primers located within adjacent APC exons. In addition, PCR primers that flank the alternatively spliced exon 9 were chosen so that the expression pattern of both splice forms could be assessed. All tissue types tested (brain, lung, aorta, spleen, heart, kidney, liver, stomach, placenta, and colonic mucosa) and cultured cell lines (lymphoblasts, HL60, and choriocarcinoma) expressed both splice forms of the APC gene. We note, however, that expression by lymphocytes normally residing in some tissues, including colon, prevents unequivocal assessment of expression. The large mRNA, containing the complete exon 9 rather than only exon 9A, appears to be the more abundant message.

Northern analysis of poly(A)-selected RNA from lymphoblasts revealed a single band of approximately 10 kb, consistent with the size of the sequenced cDNA.

EXAMPLE 15

This example discusses structural features of the APC protein predicted from the sequence.

The cDNA consensus sequence of APC predicts that the longer, more abundant form of the message codes for a 2842 or 28444 amino acid peptide with a mass of 311.8 kd. This predicted APC peptide was compared with the current data bases of protein and DNA sequences using both Intelligenetics and GCG software packages. No genes with a high degree of amino acid sequence similarity were found. Although many short (approximately 20 amino acid) regions of sequence similarity were uncovered, none was sufficently strong to reveal which, if any, might represent functional homology. Interestingly, multiple similarities to myosins and keratins did appear. The APC gene also was scanned for sequence motifs of known function; although multiple glycosylation, phosphorylation, and myristoylation sites were seen, their significance is uncertain.

Analysis of the APC peptide sequence did identify features important in considering potential protein structure. Hydropathy plots (Kyte and Doolittle, J. Mol. Biol. Vol. 157, pp. 105–132 (1982)) indicate that the APC protein is notably hydrophilic. No hydrophobic domains suggesting a signal peptide or a membrane-spanning domain were found. Analysis of the first 1000 residues indicates that α-helical rods may form (Cohen and Parry, Trends Biochem, Sci. Vol. 77, pp. 245–248 (1986); there is a scarcity of proline residues and, there are a number of regions containing heptad repeats (apolar-X-X-apolar-X-X-X). Interestingly, in exon 9A, the deleted form of exon 9, two heptad repeat regions are reconnected in the proper heptad repeat frame, deleting the intervening peptide region. After the first 1000 residues, the high proline content of the remainder of the peptide suggests a compact rather than a rod-like structure.

The most prominent feature of the second 1000 residues is a 20 amino acid repeat that is iterated seven times with semiregular spacing (Table IV; SEQ ID NO: 7). The intervening sequences between the seven repeat regions contained 114, 116, 151, 205, 107, and 58 amino acids, respectively. Finally, residues 2200–24000 contain a 200 amino acid basic domain.

TABLE I

APC EXONS

| EXON NUCLEOTIDES[1] | EXON BOUNDARY SEQUENCE[2] |
|---|---|
| 822 to 930 | catgatgttatctgtatttacctatagtctaaattataccatctataatgtgcttaatttttag/GGTTCA... <br> ...ACCAAG/gtaacagaagattacaaaccctggtcactaatgccatgactactttgctaag |
| 931 to 1309 | ggatattaaagtcgtaattttgtttctaaactcatttggcccacag/GTGGAA... <br> ...ATCCAA/gtatgttctctatagtgtacatcgtagtgcatg |
| 1310 to 1405 | catcattgctcttcaaataacaaagcattatggtttatgttgattttattttttcag/TGCCAG... <br> ...AACTAG/gtaagacaaaaatgttttttaatgacatagacaattactggtg |
| 1406 to 1545 | tagatgattgtcttttttcctcttgcccttttttaaattag/GGGGAC... <br> ...AACAAG/gtatgtttttataacatgtatttcttaagatagctcaggtatga |
| 1546 to 1623 | gcttggcttcaagttgtcttttaatgatcctctattctgtatttaatttacag/GCTACG... <br> ...CAGCAG/gtactatttagaatttcacctgtttttcttttttctcttttttctttgaggcagggtctcactctg |
| 1624 to 1740 | gcaactagtatgattttatgtataaattaatctaaaattgattaatttgcag/GTTATT... <br> ...AAAAAG/gtaccttttgaaaacatttagtactataatatgaatttcatgt |

TABLE I-continued

APC EXONS

| EXON NUCLEOTIDES[1] | EXON BOUNDARY SEQUENCE[2] |
|---|---|
| 1741 to 1955 | caactctaattagatgacccatattcagaaacttactag/GAATCA... ...CCACAG/gtatatatagagtttatattacttttaaagtacagaattcatactctcaaaaa |
| 1956 to 8973 | tcttgatttttatttcag/GCAAAT... ...GGTATTTATGCAAAAAAAAATGTTTTTGT |

[1]Relative to predicted translation initiation site
[2]Small case letters represent introns, large case letters represent exons
The entire 3' end of the cloned APC cDNA (nt 1956–8973) appeared to be encoded in this exon, as indicated by restriction endonuclease mapping and sequencing of cloned genomic DNA. The ORF ended at nt 8535. The extreme 3' end of the APC transcript has not yet been identified.

TABLE IIA

Germline mutations of the APC gene in FAP and GS Patients

EXTRA-COLONIC

| PATIENT | CODON | NUCLEOTIDE CHANGE | AMINO CHANGE | AGE | DISEASE ACID |
|---|---|---|---|---|---|
| 93 Osteoma | 279 | TCA->TGA | Ser->Stop | 39 | Mandibular |
| 24 | 301 | CGA->TGA | Arg->Stop | 46 | None |
| 34 Tumor | 301 | CGA->TGA | Arg->Stop | 27 | Desmoid |
| 21 Osteoma | 413 | CGC->TGC | Arg->Cys | 24 | Mandibular |
| 60 Osteoma | 712 | TCA->TGA | Ser->Stop | 37 | Mandibular |
| 3746 | 243 | CAGAG->CAG | splice-junction | | |
| 3460 | 301 | CGA->TGA | Arg->Stop | | |
| 3827 | 456 | CTTTCA->CTTCA | frameshift | | |
| 3712 | 500 | T->G | Tyr->Stop | | |

*The mutated nucleotides are underlined.

TABLE IIB

Somatic Mutations in Sporadic CRC Patients

| PATIENT | CODON[1] | NUCLEOTIDE CHANGE | AMINO ACID CHANGE |
|---|---|---|---|
| T35 | MCC 12 | GAG/gtaaga->GAG/gtaaga | (Splice Donor) |
| T16 | MCC 145 | ctcag/GGA->atcag/GGA | (Splice Acceptor) |
| T47 | MCC 267 | CGG->CTG | Arg->Leu |
| T81 | MCC 490 | TCG->TTG | Ser->Leu |
| T35 | MCC 506 | CGG->CAG | Arg->Gln |
| T91 | MCC 698 | GCT->GTT | Ala->Val |
| T34 | APC 288 | CCAGT->CCCAGCCAGT | (Insertion) |
| T27 | APC 331 | CGA->TGA | Arg->Stop |
| T135 | APC 437 | CAA/gtaa->CAA/gcaa | (Splice Donor) |
| T201 | APC 1338 | CAG->TAG | Gln->Stop |

For splice site mutations, the codon nearest to the mutation is listed
The underlined nucleotides were mutant; small case letters represent introns, large case letters represent exons

TABLE III

Sequences of Primers Used for SSCP Analyses

| Exon | Primer 1 | Primer 2 |
|---|---|---|
| | DP1 | |
| | UP-TCCCCGCCTGCCGCTCTC | RP-GCAGCGGCGGCTCCCGTG |
| | UP-GTGAACGGCTCTCATGCTGC | RP-ACGTGCGGGGAGGAATGGA |
| | UP-ATGATATCTTACCAAATGATATAC | RP-TTATTCCTACTTCTTCTATACAG |
| | UP-TACCCATGCTGGCTCTTTTTC | RP-TGGGGCCATCTTGTTCCTGA |
| | UP-ACATTAGGCACAAAGCTTGCAA | RP-ATCAAGCTCCAGTAAGAAGGTA |
| | SRP19 | |
| | UP-TGCGGCTCGTGGGTTGTTG | RP-GCCCCTTCCTTTCTGAGGAC |
| | UP-TTTTCTCCTGCCTCTTACTGC | RP-ATGACAGGGGGATTCCCTC |
| | UP-CCACTTAAAGCACATATATTTAGT | RP-GTATGGAAAATAGTGAAGAACC |
| | UP-TTCTTAAGTCCTGTTTTTCTTTTG | RP-TTTAGAACCTTTTTTGTGTTGTG |
| | UP-CTCAGATTATACACTAAGCCTAAC | RP-CATGTCTCTTACAGTAGTACCA |
| | DP2.5 | |
| | UP-AGGTCCAAGGGTAGCCAAGG* | RP-TAAAAATGGATAAACTACAATTAAAAG |
| | UP-AAATACAGAATCATGTCTTGAAGT | RP-ACACCTAAAGATGACAATTTGAG |
| | UP-TAACTTAGATAGCAGTAATTTCCC* | RP-ACAATAAACTGGAGTACACAAGG |
| | UP-ATAGGTCATTGCTTCTTGCTGAT* | RP-TGAATTTTAATGGATTACCTAGGT |
| | UP-CTTTTTTTGCTTTTACTGATTAACG | RP-TGTAATTCATTTTATTCCTAATACCTC |
| | UP-GGTAGCCATAGTATGATTATTTCT | RP-CTACCTATTTTTATACCCACAAAC |
| | UP-AAGAAAGCCTACACCATTTTTGC | RP-GATCATTCTTAGAACCATCTTGC |
| | UP-ACCTATAGTCTAAATTATACCATC | RP-GTCATGGCATTACTGACCAG |
| | UP-AGTCGTAATTTTGTTTCTAAACTC | RP-TGAAGGACTCCGATTTCACCC* |
| | UP-TCATTCACTCACAGCCTGATGAC* | RP-GCTTTGAAACATGCACTACGAT |
| | UP-AAACATCATTGCTCTTCAAATAAC | RP-TACCATGATTTAAAAATCCACCAG |
| | UP-GATGATTGTCTTTTTCCTCTTGC | RP-CTGAGCTATCTTAAGAAATACATG |
| | UP-TTTTAAATGATCCTCTATTCTGTAT | RP-ACAGAGTCAGACCCTCCCTCAAAG |
| | UP-TTTCTATTCTTACTGCTAGCATT | RP-ATACACAGGTAAGAAATTAGGA |
| | UP-TAGATGACCCATATTCTCTTTC | RP-CAATTAGGTCTTTTTGAGAGTA |
| 3-A | UP-GTTACTGCATACACATTGTGAC | RP-GCTTTTTGTTTCGTAACATGAAG* |
| -B | UP-AGTACAAGGATGCCAATATTATG* | RP-ACTTCTATCTTTTTCAGAACGAG* |
| -C | UP-ATTTGAATACTACAGTGTTACCC* | RP-CTTGTATTCTAATTTGGCATAAGG* |
| -D | UP-CTGCCCATACACATTCAAACAC* | RP-TGTTTGCGTCTTGCCCATCTT* |
| -E | UP-AGTCTTAAATATTCAGATGAGCAG* | RP-GTTTCTCTTCATTATATTTTATGCTA* |
| -F | UP-AAGCCTACCAATTATAGTGAACG* | RP-AGCTGATGACAAAGATGATAATC* |
| -G | UP-AAGAAACAATACAGACTTATTGTG* | RP-ATGAGTGGGGTCTCCTGAAC* |
| -H | UPATCTCCCTCCAAAAGTGGTGC* | RP-TCCATCTGGAGTACTTTCTGTG* |
| -I | UP-AGTAAATGCTGCAGTTCAGAGG* | RP-CCGTGGCATATCATCCCCC* |
| -J | UP-CCCAGACTGCTTCAAAATTACC* | RP-GAGCCTCATCTGTACTTCTGC* |
| -K | UP-CCCTCCAAATGAGTTAGCTGC* | RP-TTGTGGTATAGGTTTTACTGGTG* |
| -L | UP-ACCCAACAAAAATCAGTTAGATG* | RP-GTGGCTGCCTAACTTTAGCCTC* |
| -N | UP-ATGATGTTGACCTTTCCAGGG* | RP-ATTGTGTAACTTTTCATCAGTTGC* |
| -M | UP-AAAGACATACCAGACAGAGGG* | RP-CTTTTTTGGCATTGCGGAGCT* |
| -O | UP-AAGATGACCTGTTGCAGGAATG* | RP-GAATCAGACCAAGCTTGTCTAGAT* |
| -P | UP-CAATAGTAAGTAGTTTACATCAAG* | RP-AAACAGGACTTGTACTGTAGGA* |
| -Q | UP-CAGCCCCTTCAAGCAAACATC* | RP-GAGGACTTATTCCATTTCTACC* |
| -R | UP-CAGTCTCCTGGCCGAAACTC* | RP-GTTGACTGGCGTACTAATACAG* |
| -S | UP-TGGTAATGGAGCCAATAAAAAGG* | RP-TGGGACTTTTCGCCATCCAC* |
| -T | UP-TGTCTCTATCCACACATTCGTC* | RP-ATGTTTTTCATCCTCACTTTTTGC* |
| -U | UP-GGAGAAGAACTGGAAGTTCATC* | RP-TTGAATCTTTAATGTTTGGATTTGC* |
| -V | UP-TCTCCCACAGGTAATACTCCC | RP-GCTACAACTGAATGGGGTACG |
| -W | UP-CAGGACAAAATAATCCTGTCCC | RP-ATTTTCTTACTTTCATTCTTCCTC |

All primers are read in the 5' to 3' direction, the first primer in each pair lies 5' of the exon it amplifies: the second primer lies 3' of the exon it amplifies. Primers that lie within the exon are identified by an asterisk. UP represents the - 21M13 universal primer sequence: RP represents the M13 reverse primer sequence.

TABLE IV

Seven Different Versions of the 20-Amino Acid Repeat

| | | | | | | | | | | | | | | | | | | | | |
|---|---|---|---|---|---|---|---|---|---|---|---|---|---|---|---|---|---|---|---|---|
| Consensus: | F | Ø | V | E | Ø | T | P | Ø | C | F | S | R | Ø | S | S | L | S | S | L | S |
| 1262: | Y | C | V | E | D | T | P | I | C | F | S | R | C | S | S | L | S | S | L | S |
| 1376: | H | Y | V | Q | E | T | P | L | M | F | S | R | C | T | S | V | S | S | L | D |
| 1492: | F | A | T | E | S | T | P | D | G | F | S | C | S | S | S | L | S | A | L | S |
| 1643: | Y | C | V | E | G | T | P | I | N | F | S | T | S | T | S | L | S | D | L | T |
| 1848: | T | P | I | E | G | T | P | Y | C | F | S | R | N | D | S | L | S | S | L | D |

TABLE IV-continued

Seven Different Versions of the 20-Amino Acid Repeat

| 1953: | F | A | I | E | N | T | P | V | C | F | S | H | N | S | S | L | S | S | L | S |
| 2013: | F | H | V | E | D | T | P | V | C | F | S | R | N | S | S | L | S | S | L | S |

Numbers denote the first amino aicd of each repeat. The consensus sequence at the top reflects a majority amino acid at a given position.

What is claimed is:

1. A method to aid in the diagnosis or prognosis of a neoplastic tissue of a human, comprising:

detecting somatic alteration of wild-type APC protein in a tumor tissue isolated from a human, said alteration indicating neoplasia of the tissue, wherein the alteration of wild-type APC protein is detected by immunoblotting.

2. A method to aid in the diagnosis or prognosis of a neoplastic tissue of a human, comprising:

detecting somatic alteration of wild-type APC protein in a tumor tissue isolated from a human, said alteration indicating neoplasia of the tissue, wherein the alteration of wild-type APC protein is detected by immunocytochemistry.

3. A method to aid in the detection of genetic predisposition to cancer, including familial adenomatous polyposis (FAP) and Gardner's Syndrome (GS), in a human, comprising:

detecting a germline alteration of wild-type APC protein in a human sample selected from the group consisting of blood and fetal tissue, said alteration indicating predisposition to cancer, wherein the alteration of wild-type APC protein is detected by immunoblotting.

4. A method to aid in the detection of genetic predisposition to cancer, including familial adenomatous polyposis (FAP) and Gardner's Syndrome (GS), in a human, comprising:

detecting a germline alteration of wild-type APC protein in a human sample selected from the group consisting of blood and fetal tissue, said alteration indicating predisposition to cancer, wherein the alteration of wild-type APC protein is detected by immunocytochemistry.

5. A method to aid in the diagnosis or prognosis of a neoplastic tissue of a human, comprising:

detecting somatic alteration of wild-type APC protein in a tumor tissue isolated from a human, said alteration indicating neoplasia of the issue.

* * * * *

UNITED STATES PATENT AND TRADEMARK OFFICE
CERTIFICATE OF CORRECTION

PATENT NO.    : 6,413,727 B1  
DATED         : July 2, 2002  
INVENTOR(S)   : Hans Albertsen et al.

It is certified that error appears in the above-identified patent and that said Letters Patent is hereby corrected as shown below:

<u>Column 134,</u>
Line 61, "issue" has been replaced with -- tissue --.

Signed and Sealed this

Twenty-fifth Day of February, 2003

JAMES E. ROGAN
*Director of the United States Patent and Trademark Office*

SEQUENCE LISTING (1) GENERAL INFORMATION:

(iii) NUMBER OF SEQUENCES: 102

(2) INFORMATION FOR SEQ ID NO: 1:

(i) SEQUENCE CHARACTERISTICS:
      (A) LENGTH: 9606 base pairs
      (B) TYPE: nucleic acid
      (C) STRANDEDNESS: double
      (D) TOPOLOGY: linear (ii) MOLECULE TYPE: cDNA (vi) ORIGINAL SOURCE:
      (A) ORGANISM: Homo sapiens (vii) IMMEDIATE SOURCE:
      (B) CLONE: DP2.5(APC)

(ix) FEATURE:
      (A) NAME/KEY: CDS
      (B) LOCATION: 34..8562

(xi) SEQUENCE DESCRIPTION: SEQ ID NO: 1:

```
GGACTCGGAA ATGAGGTCCA AGGGTAGCCA AGG ATG GCT GCA GCT TCA TAT GAT        54
                                    Met Ala Ala Ala Ser Tyr Asp
                                      1               5

CAG TTG TTA AAG CAA GTT GAG GCA CTG AAG ATG GAG AAC TCA AAT CTT        102
Gln Leu Leu Lys Gln Val Glu Ala Leu Lys Met Glu Asn Ser Asn Leu
            10                  15                  20

CGA CAA GAG CTA GAA GAT AAT TCC AAT CAT CTT ACA AAA CTG GAA ACT        150
Arg Gln Glu Leu Glu Asp Asn Ser Asn His Leu Thr Lys Leu Glu Thr
     25                  30                  35

GAG GCA TCT AAT ATG AAG GAA GTA CTT AAA CAA CTA CAA GGA AGT ATT        198
Glu Ala Ser Asn Met Lys Glu Val Leu Lys Gln Leu Gln Gly Ser Ile
 40              45                  50                  55

GAA GAT GAA GCT ATG GCT TCT TCT GGA CAG ATT GAT TTA TTA GAG CGT        246
Glu Asp Glu Ala Met Ala Ser Ser Gly Gln Ile Asp Leu Leu Glu Arg
                 60                  65                  70

CTT AAA GAG CTT AAC TTA GAT AGC AGT AAT TTC CCT GGA GTA AAA CTG        294
Leu Lys Glu Leu Asn Leu Asp Ser Ser Asn Phe Pro Gly Val Lys Leu
             75                  80                  85

CGG TCA AAA ATG TCC CTC CGT TCT TAT GGA AGC CGG GAA GGA TCT GTA        342
Arg Ser Lys Met Ser Leu Arg Ser Tyr Gly Ser Arg Glu Gly Ser Val
             90                  95                 100

TCA AGC CGT TCT GGA GAG TGC AGT CCT GTT CCT ATG GGT TCA TTT CCA        390
Ser Ser Arg Ser Gly Glu Cys Ser Pro Val Pro Met Gly Ser Phe Pro
         105                 110                 115

AGA AGA GGG TTT GTA AAT GGA AGC AGA GAA AGT ACT GGA TAT TTA GAA        438
Arg Arg Gly Phe Val Asn Gly Ser Arg Glu Ser Thr Gly Tyr Leu Glu
120                 125                 130                 135

GAA CTT GAG AAA GAG AGG TCA TTG CTT CTT GCT GAT CTT GAC AAA GAA        486
```

```
                                                                -continued

Glu Leu Glu Lys Glu Arg Ser Leu Leu Leu Ala Asp Leu Asp Lys Glu
            140                 145                 150

GAA AAG GAA AAA GAC TGG TAT TAC GCT CAA CTT CAG AAT CTC ACT AAA         534
Glu Lys Glu Lys Asp Trp Tyr Tyr Ala Gln Leu Gln Asn Leu Thr Lys
                155                 160                 165

AGA ATA GAT AGT CTT CCT TTA ACT GAA AAT TTT TCC TTA CAA ACA GAT         582
Arg Ile Asp Ser Leu Pro Leu Thr Glu Asn Phe Ser Leu Gln Thr Asp
                    170                 175                 180

TTG ACC AGA AGG CAA TTG GAA TAT GAA GCA AGG CAA ATC AGA GTT GCG         630
Leu Thr Arg Arg Gln Leu Glu Tyr Glu Ala Arg Gln Ile Arg Val Ala
            185                 190                 195

ATG GAA GAA CAA CTA GGT ACC TGC CAG GAT ATG GAA AAA CGA GCA CAG         678
Met Glu Glu Gln Leu Gly Thr Cys Gln Asp Met Glu Lys Arg Ala Gln
200                 205                 210                 215

CGA AGA ATA GCC AGA ATT CAG CAA ATC GAA AAG GAC ATA CTT CGT ATA         726
Arg Arg Ile Ala Arg Ile Gln Gln Ile Glu Lys Asp Ile Leu Arg Ile
                    220                 225                 230

CGA CAG CTT TTA CAG TCC CAA GCA ACA GAA GCA GAG AGG TCA TCT CAG         774
Arg Gln Leu Leu Gln Ser Gln Ala Thr Glu Ala Glu Arg Ser Ser Gln
            235                 240                 245

AAC AAG CAT GAA ACC GGC TCA CAT GAT GCT GAG CGG CAG AAT GAA GGT         822
Asn Lys His Glu Thr Gly Ser His Asp Ala Glu Arg Gln Asn Glu Gly
            250                 255                 260

CAA GGA GTG GGA GAA ATC AAC ATG GCA ACT TCT GGT AAT GGT CAG GGT         870
Gln Gly Val Gly Glu Ile Asn Met Ala Thr Ser Gly Asn Gly Gln Gly
265                 270                 275

TCA ACT ACA CGA ATG GAC CAT GAA ACA GCC AGT GTT TTG AGT TCT AGT         918
Ser Thr Thr Arg Met Asp His Glu Thr Ala Ser Val Leu Ser Ser Ser
280                 285                 290                 295

AGC ACA CAC TCT GCA CCT CGA AGG CTG ACA AGT CAT CTG GGA ACC AAG         966
Ser Thr His Ser Ala Pro Arg Arg Leu Thr Ser His Leu Gly Thr Lys
                    300                 305                 310

GTG GAA ATG GTG TAT TCA TTG TTG TCA ATG CTT GGT ACT CAT GAT AAG        1014
Val Glu Met Val Tyr Ser Leu Leu Ser Met Leu Gly Thr His Asp Lys
            315                 320                 325

GAT GAT ATG TCG CGA ACT TTG CTA GCT ATG TCT AGC TCC CAA GAC AGC        1062
Asp Asp Met Ser Arg Thr Leu Leu Ala Met Ser Ser Ser Gln Asp Ser
            330                 335                 340

TGT ATA TCC ATG CGA CAG TCT GGA TGT CTT CCT CTC CTC ATC CAG CTT        1110
Cys Ile Ser Met Arg Gln Ser Gly Cys Leu Pro Leu Leu Ile Gln Leu
        345                 350                 355

TTA CAT GGC AAT GAC AAA GAC TCT GTA TTG TTG GGA AAT TCC CGG GGC        1158
Leu His Gly Asn Asp Lys Asp Ser Val Leu Leu Gly Asn Ser Arg Gly
360                 365                 370                 375

AGT AAA GAG GCT CGG GCC AGG GCC AGT GCA GCA CTC CAC AAC ATC ATT        1206
Ser Lys Glu Ala Arg Ala Arg Ala Ser Ala Ala Leu His Asn Ile Ile
                380                 385                 390

CAC TCA CAG CCT GAT GAC AAG AGA GGC AGG CGT GAA ATC CGA GTC CTT        1254
His Ser Gln Pro Asp Asp Lys Arg Gly Arg Arg Glu Ile Arg Val Leu
            395                 400                 405

CAT CTT TTG GAA CAG ATA CGC GCT TAC TGT GAA ACC TGT TGG GAG TGG        1302
His Leu Leu Glu Gln Ile Arg Ala Tyr Cys Glu Thr Cys Trp Glu Trp
            410                 415                 420

CAG GAA GCT CAT GAA CCA GGC ATG GAC CAG GAC AAA AAT CCA ATG CCA        1350
Gln Glu Ala His Glu Pro Gly Met Asp Gln Asp Lys Asn Pro Met Pro
            425                 430                 435

GCT CCT GTT GAA CAT CAG ATC TGT CCT GCT GTG TGT GTT CTA ATG AAA        1398
Ala Pro Val Glu His Gln Ile Cys Pro Ala Val Cys Val Leu Met Lys
440                 445                 450                 455
```

```
CTT TCA TTT GAT GAA GAG CAT AGA CAT GCA ATG AAT GAA CTA GGG GGA        1446
Leu Ser Phe Asp Glu Glu His Arg His Ala Met Asn Glu Leu Gly Gly
            460                 465                 470

CTA CAG GCC ATT GCA GAA TTA TTG CAA GTG GAC TGT GAA ATG TAT GGG        1494
Leu Gln Ala Ile Ala Glu Leu Leu Gln Val Asp Cys Glu Met Tyr Gly
            475                 480                 485

CTT ACT AAT GAC CAC TAC AGT ATT ACA CTA AGA CGA TAT GCT GGA ATG        1542
Leu Thr Asn Asp His Tyr Ser Ile Thr Leu Arg Arg Tyr Ala Gly Met
            490                 495                 500

GCT TTG ACA AAC TTG ACT TTT GGA GAT GTA GCC AAC AAG GCT ACG CTA        1590
Ala Leu Thr Asn Leu Thr Phe Gly Asp Val Ala Asn Lys Ala Thr Leu
            505                 510                 515

TGC TCT ATG AAA GGC TGC ATG AGA GCA CTT GTG GCC CAA CTA AAA TCT        1638
Cys Ser Met Lys Gly Cys Met Arg Ala Leu Val Ala Gln Leu Lys Ser
520                 525                 530                 535

GAA AGT GAA GAC TTA CAG CAG GTT ATT GCA AGT GTT TTG AGG AAT TTG        1686
Glu Ser Glu Asp Leu Gln Gln Val Ile Ala Ser Val Leu Arg Asn Leu
            540                 545                 550

TCT TGG CGA GCA GAT GTA AAT AGT AAA AAG ACG TTG CGA GAA GTT GGA        1734
Ser Trp Arg Ala Asp Val Asn Ser Lys Lys Thr Leu Arg Glu Val Gly
            555                 560                 565

AGT GTG AAA GCA TTG ATG GAA TGT GCT TTA GAA GTT AAA AAG GAA TCA        1782
Ser Val Lys Ala Leu Met Glu Cys Ala Leu Glu Val Lys Lys Glu Ser
            570                 575                 580

ACC CTC AAA AGC GTA TTG AGT GCC TTA TGG AAT TTG TCA GCA CAT TGC        1830
Thr Leu Lys Ser Val Leu Ser Ala Leu Trp Asn Leu Ser Ala His Cys
            585                 590                 595

ACT GAG AAT AAA GCT GAT ATA TGT GCT GTA GAT GGT GCA CTT GCA TTT        1878
Thr Glu Asn Lys Ala Asp Ile Cys Ala Val Asp Gly Ala Leu Ala Phe
600                 605                 610                 615

TTG GTT GGC ACT CTT ACT TAC CGG AGC CAG ACA AAC ACT TTA GCC ATT        1926
Leu Val Gly Thr Leu Thr Tyr Arg Ser Gln Thr Asn Thr Leu Ala Ile
            620                 625                 630

ATT GAA AGT GGA GGT GGG ATA TTA CGG AAT GTG TCC AGC TTG ATA GCT        1974
Ile Glu Ser Gly Gly Gly Ile Leu Arg Asn Val Ser Ser Leu Ile Ala
            635                 640                 645

ACA AAT GAG GAC CAC AGG CAA ATC CTA AGA GAG AAC AAC TGT CTA CAA        2022
Thr Asn Glu Asp His Arg Gln Ile Leu Arg Glu Asn Asn Cys Leu Gln
            650                 655                 660

ACT TTA TTA CAA CAC TTA AAA TCT CAT AGT TTG ACA ATA GTC AGT AAT        2070
Thr Leu Leu Gln His Leu Lys Ser His Ser Leu Thr Ile Val Ser Asn
            665                 670                 675

GCA TGT GGA ACT TTG TGG AAT CTC TCA GCA AGA AAT CCT AAA GAC CAG        2118
Ala Cys Gly Thr Leu Trp Asn Leu Ser Ala Arg Asn Pro Lys Asp Gln
680                 685                 690                 695

GAA GCA TTA TGG GAC ATG GGG GCA GTT AGC ATG CTC AAG AAC CTC ATT        2166
Glu Ala Leu Trp Asp Met Gly Ala Val Ser Met Leu Lys Asn Leu Ile
            700                 705                 710

CAT TCA AAG CAC AAA ATG ATT GCT ATG GGA AGT GCT GCA GCT TTA AGG        2214
His Ser Lys His Lys Met Ile Ala Met Gly Ser Ala Ala Ala Leu Arg
            715                 720                 725

AAT CTC ATG GCA AAT AGG CCT GCG AAG TAC AAG GAT GCC AAT ATT ATG        2262
Asn Leu Met Ala Asn Arg Pro Ala Lys Tyr Lys Asp Ala Asn Ile Met
            730                 735                 740

TCT CCT GGC TCA AGC TTG CCA TCT CTT CAT GTT AGG AAA CAA AAA GCC        2310
Ser Pro Gly Ser Ser Leu Pro Ser Leu His Val Arg Lys Gln Lys Ala
            745                 750                 755

CTA GAA GCA GAA TTA GAT GCT CAG CAC TTA TCA GAA ACT TTT GAC AAT        2358
Leu Glu Ala Glu Leu Asp Ala Gln His Leu Ser Glu Thr Phe Asp Asn
760                 765                 770                 775
```

```
ATA GAC AAT TTA AGT CCC AAG GCA TCT CAT CGT AGT AAG CAG AGA CAC    2406
Ile Asp Asn Leu Ser Pro Lys Ala Ser His Arg Ser Lys Gln Arg His
            780                 785                 790

AAG CAA AGT CTC TAT GGT GAT TAT GTT TTT GAC ACC AAT CGA CAT GAT    2454
Lys Gln Ser Leu Tyr Gly Asp Tyr Val Phe Asp Thr Asn Arg His Asp
        795                 800                 805

GAT AAT AGG TCA GAC AAT TTT AAT ACT GGC AAC ATG ACT GTC CTT TCA    2502
Asp Asn Arg Ser Asp Asn Phe Asn Thr Gly Asn Met Thr Val Leu Ser
            810                 815                 820

CCA TAT TTG AAT ACT ACA GTG TTA CCC AGC TCC TCT TCA TCA AGA GGA    2550
Pro Tyr Leu Asn Thr Thr Val Leu Pro Ser Ser Ser Ser Arg Gly
        825                 830                 835

AGC TTA GAT AGT TCT CGT TCT GAA AAA GAT AGA AGT TTG GAG AGA GAA    2598
Ser Leu Asp Ser Ser Arg Ser Glu Lys Asp Arg Ser Leu Glu Arg Glu
840                 845                 850                 855

CGC GGA ATT GGT CTA GGC AAC TAC CAT CCA GCA ACA GAA AAT CCA GGA    2646
Arg Gly Ile Gly Leu Gly Asn Tyr His Pro Ala Thr Glu Asn Pro Gly
            860                 865                 870

ACT TCT TCA AAG CGA GGT TTG CAG ATC TCC ACC ACT GCA GCC CAG ATT    2694
Thr Ser Ser Lys Arg Gly Leu Gln Ile Ser Thr Thr Ala Ala Gln Ile
        875                 880                 885

GCC AAA GTC ATG GAA GAA GTG TCA GCC ATT CAT ACC TCT CAG GAA GAC    2742
Ala Lys Val Met Glu Glu Val Ser Ala Ile His Thr Ser Gln Glu Asp
            890                 895                 900

AGA AGT TCT GGG TCT ACC ACT GAA TTA CAT TGT GTG ACA GAT GAG AGA    2790
Arg Ser Ser Gly Ser Thr Thr Glu Leu His Cys Val Thr Asp Glu Arg
905                 910                 915

AAT GCA CTT AGA AGA AGC TCT GCT GCC CAT ACA CAT TCA AAC ACT TAC    2838
Asn Ala Leu Arg Arg Ser Ser Ala Ala His Thr His Ser Asn Thr Tyr
920                 925                 930                 935

AAT TTC ACT AAG TCG GAA AAT TCA AAT AGG ACA TGT TCT ATG CCT TAT    2886
Asn Phe Thr Lys Ser Glu Asn Ser Asn Arg Thr Cys Ser Met Pro Tyr
            940                 945                 950

GCC AAA TTA GAA TAC AAG AGA TCT TCA AAT GAT AGT TTA AAT AGT GTC    2934
Ala Lys Leu Glu Tyr Lys Arg Ser Ser Asn Asp Ser Leu Asn Ser Val
        955                 960                 965

AGT AGT AAT GAT GGT TAT GGT AAA AGA GGT CAA ATG AAA CCC TCG ATT    2982
Ser Ser Asn Asp Gly Tyr Gly Lys Arg Gly Gln Met Lys Pro Ser Ile
            970                 975                 980

GAA TCC TAT TCT GAA GAT GAT GAA AGT AAG TTT TGC AGT TAT GGT CAA    3030
Glu Ser Tyr Ser Glu Asp Asp Glu Ser Lys Phe Cys Ser Tyr Gly Gln
        985                 990                 995

TAC CCA GCC GAC CTA GCC CAT AAA ATA CAT AGT GCA AAT CAT ATG GAT    3078
Tyr Pro Ala Asp Leu Ala His Lys Ile His Ser Ala Asn His Met Asp
1000                1005                1010                1015

GAT AAT GAT GGA GAA CTA GAT ACA CCA ATA AAT TAT AGT CTT AAA TAT    3126
Asp Asn Asp Gly Glu Leu Asp Thr Pro Ile Asn Tyr Ser Leu Lys Tyr
            1020                1025                1030

TCA GAT GAG CAG TTG AAC TCT GGA AGG CAA AGT CCT TCA CAG AAT GAA    3174
Ser Asp Glu Gln Leu Asn Ser Gly Arg Gln Ser Pro Ser Gln Asn Glu
        1035                1040                1045

AGA TGG GCA AGA CCC AAA CAC ATA ATA GAA GAT GAA ATA AAA CAA AGT    3222
Arg Trp Ala Arg Pro Lys His Ile Ile Glu Asp Glu Ile Lys Gln Ser
            1050                1055                1060

GAG CAA AGA CAA TCA AGG AAT CAA AGT ACA ACT TAT CCT GTT TAT ACT    3270
Glu Gln Arg Gln Ser Arg Asn Gln Ser Thr Thr Tyr Pro Val Tyr Thr
        1065                1070                1075

GAG AGC ACT GAT GAT AAA CAC CTC AAG TTC CAA CCA CAT TTT GGA CAG    3318
Glu Ser Thr Asp Asp Lys His Leu Lys Phe Gln Pro His Phe Gly Gln
```

```
                                                                -continued
1080              1085              1090              1095

CAG GAA TGT GTT TCT CCA TAC AGG TCA CGG GGA GCC AAT GGT TCA GAA    3366
Gln Glu Cys Val Ser Pro Tyr Arg Ser Arg Gly Ala Asn Gly Ser Glu
                1100              1105              1110

ACA AAT CGA GTG GGT TCT AAT CAT GGA ATT AAT CAA AAT GTA AGC CAG    3414
Thr Asn Arg Val Gly Ser Asn His Gly Ile Asn Gln Asn Val Ser Gln
                1115              1120              1125

TCT TTG TGT CAA GAA GAT GAC TAT GAA GAT GAT AAG CCT ACC AAT TAT    3462
Ser Leu Cys Gln Glu Asp Asp Tyr Glu Asp Asp Lys Pro Thr Asn Tyr
                1130              1135              1140

AGT GAA CGT TAC TCT GAA GAA GAA CAG CAT GAA GAA GAA GAG AGA CCA    3510
Ser Glu Arg Tyr Ser Glu Glu Glu Gln His Glu Glu Glu Glu Arg Pro
                1145              1150              1155

ACA AAT TAT AGC ATA AAA TAT AAT GAA GAG AAA CGT CAT GTG GAT CAG    3558
Thr Asn Tyr Ser Ile Lys Tyr Asn Glu Glu Lys Arg His Val Asp Gln
1160              1165              1170              1175

CCT ATT GAT TAT AGT TTA AAA TAT GCC ACA GAT ATT CCT TCA TCA CAG    3606
Pro Ile Asp Tyr Ser Leu Lys Tyr Ala Thr Asp Ile Pro Ser Ser Gln
                1180              1185              1190

AAA CAG TCA TTT TCA TTC TCA AAG AGT TCA TCT GGA CAA AGC AGT AAA    3654
Lys Gln Ser Phe Ser Phe Ser Lys Ser Ser Ser Gly Gln Ser Ser Lys
                1195              1200              1205

ACC GAA CAT ATG TCT TCA AGC AGT GAG AAT ACG TCC ACA CCT TCA TCT    3702
Thr Glu His Met Ser Ser Ser Ser Glu Asn Thr Ser Thr Pro Ser Ser
                1210              1215              1220

AAT GCC AAG AGG CAG AAT CAG CTC CAT CCA AGT TCT GCA CAG AGT AGA    3750
Asn Ala Lys Arg Gln Asn Gln Leu His Pro Ser Ser Ala Gln Ser Arg
                1225              1230              1235

AGT GGT CAG CCT CAA AAG GCT GCC ACT TGC AAA GTT TCT TCT ATT AAC    3798
Ser Gly Gln Pro Gln Lys Ala Ala Thr Cys Lys Val Ser Ser Ile Asn
1240              1245              1250              1255

CAA GAA ACA ATA CAG ACT TAT TGT GTA GAA GAT ACT CCA ATA TGT TTT    3846
Gln Glu Thr Ile Gln Thr Tyr Cys Val Glu Asp Thr Pro Ile Cys Phe
                1260              1265              1270

TCA AGA TGT AGT TCA TTA TCA TCT TTG TCA TCA GCT GAA GAT GAA ATA    3894
Ser Arg Cys Ser Ser Leu Ser Ser Leu Ser Ser Ala Glu Asp Glu Ile
                1275              1280              1285

GGA TGT AAT CAG ACG ACA CAG GAA GCA GAT TCT GCT AAT ACC CTG CAA    3942
Gly Cys Asn Gln Thr Thr Gln Glu Ala Asp Ser Ala Asn Thr Leu Gln
                1290              1295              1300

ATA GCA GAA ATA AAA GGA AAG ATT GGA ACT AGG TCA GCT GAA GAT CCT    3990
Ile Ala Glu Ile Lys Gly Lys Ile Gly Thr Arg Ser Ala Glu Asp Pro
                1305              1310              1315

GTG AGC GAA GTT CCA GCA GTG TCA CAG CAC CCT AGA ACC AAA TCC AGC    4038
Val Ser Glu Val Pro Ala Val Ser Gln His Pro Arg Thr Lys Ser Ser
1320              1325              1330              1335

AGA CTG CAG GGT TCT AGT TTA TCT TCA GAA TCA GCC AGG CAC AAA GCT    4086
Arg Leu Gln Gly Ser Ser Leu Ser Ser Glu Ser Ala Arg His Lys Ala
                1340              1345              1350

GTT GAA TTT CCT TCA GGA GCG AAA TCT CCC TCC AAA AGT GGT GCT CAG    4134
Val Glu Phe Pro Ser Gly Ala Lys Ser Pro Ser Lys Ser Gly Ala Gln
                1355              1360              1365

ACA CCC AAA AGT CCA CCT GAA CAC TAT GTT CAG GAG ACC CCA CTC ATG    4182
Thr Pro Lys Ser Pro Pro Glu His Tyr Val Gln Glu Thr Pro Leu Met
                1370              1375              1380

TTT AGC AGA TGT ACT TCT GTC AGT TCA CTT GAT AGT TTT GAG AGT CGT    4230
Phe Ser Arg Cys Thr Ser Val Ser Ser Leu Asp Ser Phe Glu Ser Arg
                1385              1390              1395

TCG ATT GCC AGC TCC GTT CAG AGT GAA CCA TGC AGT GGA ATG GTA AGT    4278
```

```
Ser Ile Ala Ser Ser Val Gln Ser Glu Pro Cys Ser Gly Met Val Ser
1400                1405                1410                1415

GGC ATT ATA AGC CCC AGT GAT CTT CCA GAT AGC CCT GGA CAA ACC ATG         4326
Gly Ile Ile Ser Pro Ser Asp Leu Pro Asp Ser Pro Gly Gln Thr Met
                1420                1425                1430

CCA CCA AGC AGA AGT AAA ACA CCT CCA CCA CCT CCT CAA ACA GCT CAA         4374
Pro Pro Ser Arg Ser Lys Thr Pro Pro Pro Pro Pro Gln Thr Ala Gln
                1435                1440                1445

ACC AAG CGA GAA GTA CCT AAA AAT AAA GCA CCT ACT GCT GAA AAG AGA         4422
Thr Lys Arg Glu Val Pro Lys Asn Lys Ala Pro Thr Ala Glu Lys Arg
                1450                1455                1460

GAG AGT GGA CCT AAG CAA GCT GCA GTA AAT GCT GCA GTT CAG AGG GTC         4470
Glu Ser Gly Pro Lys Gln Ala Ala Val Asn Ala Ala Val Gln Arg Val
1465                1470                1475

CAG GTT CTT CCA GAT GCT GAT ACT TTA TTA CAT TTT GCC ACA GAA AGT         4518
Gln Val Leu Pro Asp Ala Asp Thr Leu Leu His Phe Ala Thr Glu Ser
1480                1485                1490                1495

ACT CCA GAT GGA TTT TCT TGT TCA TCC AGC CTG AGT GCT CTG AGC CTC         4566
Thr Pro Asp Gly Phe Ser Cys Ser Ser Ser Leu Ser Ala Leu Ser Leu
                1500                1505                1510

GAT GAG CCA TTT ATA CAG AAA GAT GTG GAA TTA AGA ATA ATG CCT CCA         4614
Asp Glu Pro Phe Ile Gln Lys Asp Val Glu Leu Arg Ile Met Pro Pro
                1515                1520                1525

GTT CAG GAA AAT GAC AAT GGG AAT GAA ACA GAA TCA GAG CAG CCT AAA         4662
Val Gln Glu Asn Asp Asn Gly Asn Glu Thr Glu Ser Glu Gln Pro Lys
                1530                1535                1540

GAA TCA AAT GAA AAC CAA GAG AAA GAG GCA GAA AAA ACT ATT GAT TCT         4710
Glu Ser Asn Glu Asn Gln Glu Lys Glu Ala Glu Lys Thr Ile Asp Ser
                1545                1550                1555

GAA AAG GAC CTA TTA GAT GAT TCA GAT GAT GAT GAT ATT GAA ATA CTA         4758
Glu Lys Asp Leu Leu Asp Asp Ser Asp Asp Asp Asp Ile Glu Ile Leu
1560                1565                1570                1575

GAA GAA TGT ATT ATT TCT GCC ATG CCA ACA AAG TCA TCA CGT AAA GGC         4806
Glu Glu Cys Ile Ile Ser Ala Met Pro Thr Lys Ser Ser Arg Lys Gly
                1580                1585                1590

AAA AAG CCA GCC CAG ACT GCT TCA AAA TTA CCT CCA CCT GTG GCA AGG         4854
Lys Lys Pro Ala Gln Thr Ala Ser Lys Leu Pro Pro Pro Val Ala Arg
                1595                1600                1605

AAA CCA AGT CAG CTG CCT GTG TAC AAA CTT CTA CCA TCA CAA AAC AGG         4902
Lys Pro Ser Gln Leu Pro Val Tyr Lys Leu Leu Pro Ser Gln Asn Arg
                1610                1615                1620

TTG CAA CCC CAA AAG CAT GTT AGT TTT ACA CCG GGG GAT GAT ATG CCA         4950
Leu Gln Pro Gln Lys His Val Ser Phe Thr Pro Gly Asp Asp Met Pro
                1625                1630                1635

CGG GTG TAT TGT GTT GAA GGG ACA CCT ATA AAC TTT TCC ACA GCT ACA         4998
Arg Val Tyr Cys Val Glu Gly Thr Pro Ile Asn Phe Ser Thr Ala Thr
1640                1645                1650                1655

TCT CTA AGT GAT CTA ACA ATC GAA TCC CCT CCA AAT GAG TTA GCT GCT         5046
Ser Leu Ser Asp Leu Thr Ile Glu Ser Pro Pro Asn Glu Leu Ala Ala
                1660                1665                1670

GGA GAA GGA GTT AGA GGA GGA GCA CAG TCA GGT GAA TTT GAA AAA CGA         5094
Gly Glu Gly Val Arg Gly Gly Ala Gln Ser Gly Glu Phe Glu Lys Arg
                1675                1680                1685

GAT ACC ATT CCT ACA GAA GGC AGA AGT ACA GAT GAG GCT CAA GGA GGA         5142
Asp Thr Ile Pro Thr Glu Gly Arg Ser Thr Asp Glu Ala Gln Gly Gly
                1690                1695                1700

AAA ACC TCA TCT GTA ACC ATA CCT GAA TTG GAT GAC AAT AAA GCA GAG         5190
Lys Thr Ser Ser Val Thr Ile Pro Glu Leu Asp Asp Asn Lys Ala Glu
                1705                1710                1715
```

```
GAA GGT GAT ATT CTT GCA GAA TGC ATT AAT TCT GCT ATG CCC AAA GGG      5238
Glu Gly Asp Ile Leu Ala Glu Cys Ile Asn Ser Ala Met Pro Lys Gly
1720                1725                1730                1735

AAA AGT CAC AAG CCT TTC CGT GTG AAA AAG ATA ATG GAC CAG GTC CAG      5286
Lys Ser His Lys Pro Phe Arg Val Lys Lys Ile Met Asp Gln Val Gln
                1740                1745                1750

CAA GCA TCT GCG TCG TCT TCT GCA CCC AAC AAA AAT CAG TTA GAT GGT      5334
Gln Ala Ser Ala Ser Ser Ser Ala Pro Asn Lys Asn Gln Leu Asp Gly
            1755                1760                1765

AAG AAA AAG AAA CCA ACT TCA CCA GTA AAA CCT ATA CCA CAA AAT ACT      5382
Lys Lys Lys Lys Pro Thr Ser Pro Val Lys Pro Ile Pro Gln Asn Thr
        1770                1775                1780

GAA TAT AGG ACA CGT GTA AGA AAA AAT GCA GAC TCA AAA AAT AAT TTA      5430
Glu Tyr Arg Thr Arg Val Arg Lys Asn Ala Asp Ser Lys Asn Asn Leu
    1785                1790                1795

AAT GCT GAG AGA GTT TTC TCA GAC AAC AAA GAT TCA AAG AAA CAG AAT      5478
Asn Ala Glu Arg Val Phe Ser Asp Asn Lys Asp Ser Lys Lys Gln Asn
1800                1805                1810                1815

TTG AAA AAT AAT TCC AAG GAC TTC AAT GAT AAG CTC CCA AAT AAT GAA      5526
Leu Lys Asn Asn Ser Lys Asp Phe Asn Asp Lys Leu Pro Asn Asn Glu
                1820                1825                1830

GAT AGA GTC AGA GGA AGT TTT GCT TTT GAT TCA CCT CAT CAT TAC ACG      5574
Asp Arg Val Arg Gly Ser Phe Ala Phe Asp Ser Pro His His Tyr Thr
            1835                1840                1845

CCT ATT GAA GGA ACT CCT TAC TGT TTT TCA CGA AAT GAT TCT TTG AGT      5622
Pro Ile Glu Gly Thr Pro Tyr Cys Phe Ser Arg Asn Asp Ser Leu Ser
        1850                1855                1860

TCT CTA GAT TTT GAT GAT GAT GAT GTT GAC CTT TCC AGG GAA AAG GCT      5670
Ser Leu Asp Phe Asp Asp Asp Asp Val Asp Leu Ser Arg Glu Lys Ala
    1865                1870                1875

GAA TTA AGA AAG GCA AAA GAA AAT AAG GAA TCA GAG GCT AAA GTT ACC      5718
Glu Leu Arg Lys Ala Lys Glu Asn Lys Glu Ser Glu Ala Lys Val Thr
1880                1885                1890                1895

AGC CAC ACA GAA CTA ACC TCC AAC CAA CAA TCA GCT AAT AAG ACA CAA      5766
Ser His Thr Glu Leu Thr Ser Asn Gln Gln Ser Ala Asn Lys Thr Gln
                1900                1905                1910

GCT ATT GCA AAG CAG CCA ATA AAT CGA GGT CAG CCT AAA CCC ATA CTT      5814
Ala Ile Ala Lys Gln Pro Ile Asn Arg Gly Gln Pro Lys Pro Ile Leu
            1915                1920                1925

CAG AAA CAA TCC ACT TTT CCC CAG TCA TCC AAA GAC ATA CCA GAC AGA      5862
Gln Lys Gln Ser Thr Phe Pro Gln Ser Ser Lys Asp Ile Pro Asp Arg
        1930                1935                1940

GGG GCA GCA ACT GAT GAA AAG TTA CAG AAT TTT GCT ATT GAA AAT ACT      5910
Gly Ala Ala Thr Asp Glu Lys Leu Gln Asn Phe Ala Ile Glu Asn Thr
    1945                1950                1955

CCA GTT TGC TTT TCT CAT AAT TCC TCT CTG AGT TCT CTC AGT GAC ATT      5958
Pro Val Cys Phe Ser His Asn Ser Ser Leu Ser Ser Leu Ser Asp Ile
1960                1965                1970                1975

GAC CAA GAA AAC AAC AAT AAA GAA AAT GAA CCT ATC AAA GAG ACT GAG      6006
Asp Gln Glu Asn Asn Asn Lys Glu Asn Glu Pro Ile Lys Glu Thr Glu
                1980                1985                1990

CCC CCT GAC TCA CAG GGA GAA CCA AGT AAA CCT CAA GCA TCA GGC TAT      6054
Pro Pro Asp Ser Gln Gly Glu Pro Ser Lys Pro Gln Ala Ser Gly Tyr
            1995                2000                2005

GCT CCT AAA TCA TTT CAT GTT GAA GAT ACC CCA GTT TGT TTC TCA AGA      6102
Ala Pro Lys Ser Phe His Val Glu Asp Thr Pro Val Cys Phe Ser Arg
        2010                2015                2020

AAC AGT TCT CTC AGT TCT CTT AGT ATT GAC TCT GAA GAT GAC CTG TTG      6150
Asn Ser Ser Leu Ser Ser Leu Ser Ile Asp Ser Glu Asp Asp Leu Leu
    2025                2030                2035
```

```
CAG GAA TGT ATA AGC TCC GCA ATG CCA AAA AAG AAA AAG CCT TCA AGA      6198
Gln Glu Cys Ile Ser Ser Ala Met Pro Lys Lys Lys Lys Pro Ser Arg
2040            2045                2050                2055

CTC AAG GGT GAT AAT GAA AAA CAT AGT CCC AGA AAT ATG GGT GGC ATA      6246
Leu Lys Gly Asp Asn Glu Lys His Ser Pro Arg Asn Met Gly Gly Ile
                2060                2065                2070

TTA GGT GAA GAT CTG ACA CTT GAT TTG AAA GAT ATA CAG AGA CCA GAT      6294
Leu Gly Glu Asp Leu Thr Leu Asp Leu Lys Asp Ile Gln Arg Pro Asp
            2075                2080                2085

TCA GAA CAT GGT CTA TCC CCT GAT TCA GAA AAT TTT GAT TGG AAA GCT      6342
Ser Glu His Gly Leu Ser Pro Asp Ser Glu Asn Phe Asp Trp Lys Ala
        2090                2095                2100

ATT CAG GAA GGT GCA AAT TCC ATA GTA AGT AGT TTA CAT CAA GCT GCT      6390
Ile Gln Glu Gly Ala Asn Ser Ile Val Ser Ser Leu His Gln Ala Ala
    2105                2110                2115

GCT GCT GCA TGT TTA TCT AGA CAA GCT TCG TCT GAT TCA GAT TCC ATC      6438
Ala Ala Ala Cys Leu Ser Arg Gln Ala Ser Ser Asp Ser Asp Ser Ile
2120            2125                2130                2135

CTT TCC CTG AAA TCA GGA ATC TCT CTG GGA TCA CCA TTT CAT CTT ACA      6486
Leu Ser Leu Lys Ser Gly Ile Ser Leu Gly Ser Pro Phe His Leu Thr
                2140                2145                2150

CCT GAT CAA GAA GAA AAA CCC TTT ACA AGT AAT AAA GGC CCA CGA ATT      6534
Pro Asp Gln Glu Glu Lys Pro Phe Thr Ser Asn Lys Gly Pro Arg Ile
            2155                2160                2165

CTA AAA CCA GGG GAG AAA AGT ACA TTG GAA ACT AAA AAG ATA GAA TCT      6582
Leu Lys Pro Gly Glu Lys Ser Thr Leu Glu Thr Lys Lys Ile Glu Ser
        2170                2175                2180

GAA AGT AAA GGA ATC AAA GGA GGA AAA AAA GTT TAT AAA AGT TTG ATT      6630
Glu Ser Lys Gly Ile Lys Gly Gly Lys Lys Val Tyr Lys Ser Leu Ile
    2185                2190                2195

ACT GGA AAA GTT CGA TCT AAT TCA GAA ATT TCA GGC CAA ATG AAA CAG      6678
Thr Gly Lys Val Arg Ser Asn Ser Glu Ile Ser Gly Gln Met Lys Gln
2200            2205                2210                2215

CCC CTT CAA GCA AAC ATG CCT TCA ATC TCT CGA GGC AGG ACA ATG ATT      6726
Pro Leu Gln Ala Asn Met Pro Ser Ile Ser Arg Gly Arg Thr Met Ile
                2220                2225                2230

CAT ATT CCA GGA GTT CGA AAT AGC TCC TCA AGT ACA AGT CCT GTT TCT      6774
His Ile Pro Gly Val Arg Asn Ser Ser Ser Thr Ser Pro Val Ser
            2235                2240                2245

AAA AAA GGC CCA CCC CTT AAG ACT CCA GCC TCC AAA AGC CCT AGT GAA      6822
Lys Lys Gly Pro Pro Leu Lys Thr Pro Ala Ser Lys Ser Pro Ser Glu
        2250                2255                2260

GGT CAA ACA GCC ACC ACT TCT CCT AGA GGA GCC AAG CCA TCT GTG AAA      6870
Gly Gln Thr Ala Thr Thr Ser Pro Arg Gly Ala Lys Pro Ser Val Lys
    2265                2270                2275

TCA GAA TTA AGC CCT GTT GCC AGG CAG ACA TCC CAA ATA GGT GGG TCA      6918
Ser Glu Leu Ser Pro Val Ala Arg Gln Thr Ser Gln Ile Gly Gly Ser
2280            2285                2290                2295

AGT AAA GCA CCT TCT AGA TCA GGA TCT AGA GAT TCG ACC CCT TCA AGA      6966
Ser Lys Ala Pro Ser Arg Ser Gly Ser Arg Asp Ser Thr Pro Ser Arg
                2300                2305                2310

CCT GCC CAG CAA CCA TTA AGT AGA CCT ATA CAG TCT CCT GGC CGA AAC      7014
Pro Ala Gln Gln Pro Leu Ser Arg Pro Ile Gln Ser Pro Gly Arg Asn
            2315                2320                2325

TCA ATT TCC CCT GGT AGA AAT GGA ATA AGT CCT CCT AAC AAA TTA TCT      7062
Ser Ile Ser Pro Gly Arg Asn Gly Ile Ser Pro Pro Asn Lys Leu Ser
        2330                2335                2340

CAA CTT CCA AGG ACA TCA TCC CCT AGT ACT GCT TCA ACT AAG TCC TCA      7110
Gln Leu Pro Arg Thr Ser Ser Pro Ser Thr Ala Ser Thr Lys Ser Ser
```

```
                2345                2350                2355
GGT TCT GGA AAA ATG TCA TAT ACA TCT CCA GGT AGA CAG ATG AGC CAA     7158
Gly Ser Gly Lys Met Ser Tyr Thr Ser Pro Gly Arg Gln Met Ser Gln
2360                2365                2370                2375

CAG AAC CTT ACC AAA CAA ACA GGT TTA TCC AAG AAT GCC AGT AGT ATT     7206
Gln Asn Leu Thr Lys Gln Thr Gly Leu Ser Lys Asn Ala Ser Ser Ile
            2380                2385                2390

CCA AGA AGT GAG TCT GCC TCC AAA GGA CTA AAT CAG ATG AAT AAT GGT     7254
Pro Arg Ser Glu Ser Ala Ser Lys Gly Leu Asn Gln Met Asn Asn Gly
        2395                2400                2405

AAT GGA GCC AAT AAA AAG GTA GAA CTT TCT AGA ATG TCT TCA ACT AAA     7302
Asn Gly Ala Asn Lys Lys Val Glu Leu Ser Arg Met Ser Ser Thr Lys
        2410                2415                2420

TCA AGT GGA AGT GAA TCT GAT AGA TCA GAA AGA CCT GTA TTA GTA CGC     7350
Ser Ser Gly Ser Glu Ser Asp Arg Ser Glu Arg Pro Val Leu Val Arg
    2425                2430                2435

CAG TCA ACT TTC ATC AAA GAA GCT CCA AGC CCA ACC TTA AGA AGA AAA     7398
Gln Ser Thr Phe Ile Lys Glu Ala Pro Ser Pro Thr Leu Arg Arg Lys
2440                2445                2450                2455

TTG GAG GAA TCT GCT TCA TTT GAA TCT CTT TCT CCA TCA TCT AGA CCA     7446
Leu Glu Glu Ser Ala Ser Phe Glu Ser Leu Ser Pro Ser Ser Arg Pro
            2460                2465                2470

GCT TCT CCC ACT AGG TCC CAG GCA CAA ACT CCA GTT TTA AGT CCT TCC     7494
Ala Ser Pro Thr Arg Ser Gln Ala Gln Thr Pro Val Leu Ser Pro Ser
        2475                2480                2485

CTT CCT GAT ATG TCT CTA TCC ACA CAT TCG TCT GTT CAG GCT GGT GGA     7542
Leu Pro Asp Met Ser Leu Ser Thr His Ser Ser Val Gln Ala Gly Gly
        2490                2495                2500

TGG CGA AAA CTC CCA CCT AAT CTC AGT CCC ACT ATA GAG TAT AAT GAT     7590
Trp Arg Lys Leu Pro Pro Asn Leu Ser Pro Thr Ile Glu Tyr Asn Asp
    2505                2510                2515

GGA AGA CCA GCA AAG CGC CAT GAT ATT GCA CGG TCT CAT TCT GAA AGT     7638
Gly Arg Pro Ala Lys Arg His Asp Ile Ala Arg Ser His Ser Glu Ser
2520                2525                2530                2535

CCT TCT AGA CTT CCA ATC AAT AGG TCA GGA ACC TGG AAA CGT GAG CAC     7686
Pro Ser Arg Leu Pro Ile Asn Arg Ser Gly Thr Trp Lys Arg Glu His
            2540                2545                2550

AGC AAA CAT TCA TCA TCC CTT CCT CGA GTA AGC ACT TGG AGA AGA ACT     7734
Ser Lys His Ser Ser Ser Leu Pro Arg Val Ser Thr Trp Arg Arg Thr
        2555                2560                2565

GGA AGT TCA TCT TCA ATT CTT TCT GCT TCA TCA GAA TCC AGT GAA AAA     7782
Gly Ser Ser Ser Ser Ile Leu Ser Ala Ser Ser Glu Ser Ser Glu Lys
        2570                2575                2580

GCA AAA AGT GAG GAT GAA AAA CAT GTG AAC TCT ATT TCA GGA ACC AAA     7830
Ala Lys Ser Glu Asp Glu Lys His Val Asn Ser Ile Ser Gly Thr Lys
    2585                2590                2595

CAA AGT AAA GAA AAC CAA GTA TCC GCA AAA GGA ACA TGG AGA AAA ATA     7878
Gln Ser Lys Glu Asn Gln Val Ser Ala Lys Gly Thr Trp Arg Lys Ile
2600                2605                2610                2615

AAA GAA AAT GAA TTT TCT CCC ACA AAT AGT ACT TCT CAG ACC GTT TCC     7926
Lys Glu Asn Glu Phe Ser Pro Thr Asn Ser Thr Ser Gln Thr Val Ser
            2620                2625                2630

TCA GGT GCT ACA AAT GGT GCT GAA TCA AAG ACT CTA ATT TAT CAA ATG     7974
Ser Gly Ala Thr Asn Gly Ala Glu Ser Lys Thr Leu Ile Tyr Gln Met
        2635                2640                2645

GCA CCT GCT GTT TCT AAA ACA GAG GAT GTT TGG GTG AGA ATT GAG GAC     8022
Ala Pro Ala Val Ser Lys Thr Glu Asp Val Trp Val Arg Ile Glu Asp
        2650                2655                2660

TGT CCC ATT AAC AAT CCT AGA TCT GGA AGA TCT CCC ACA GGT AAT ACT     8070
```

```
                                                              -continued

Cys Pro Ile Asn Asn Pro Arg Ser Gly Arg Ser Pro Thr Gly Asn Thr
    2665                2670                2675

CCC CCG GTG ATT GAC AGT GTT TCA GAA AAG GCA AAT CCA AAC ATT AAA       8118
Pro Pro Val Ile Asp Ser Val Ser Glu Lys Ala Asn Pro Asn Ile Lys
2680                2685                2690                2695

GAT TCA AAA GAT AAT CAG GCA AAA CAA AAT GTG GGT AAT GGC AGT GTT       8166
Asp Ser Lys Asp Asn Gln Ala Lys Gln Asn Val Gly Asn Gly Ser Val
                2700                2705                2710

CCC ATG CGT ACC GTG GGT TTG GAA AAT CGC CTG ACC TCC TTT ATT CAG       8214
Pro Met Arg Thr Val Gly Leu Glu Asn Arg Leu Thr Ser Phe Ile Gln
            2715                2720                2725

GTG GAT GCC CCT GAC CAA AAA GGA ACT GAG ATA AAA CCA GGA CAA AAT       8262
Val Asp Ala Pro Asp Gln Lys Gly Thr Glu Ile Lys Pro Gly Gln Asn
        2730                2735                2740

AAT CCT GTC CCT GTA TCA GAG ACT AAT GAA AGT CCT ATA GTG GAA CGT       8310
Asn Pro Val Pro Val Ser Glu Thr Asn Glu Ser Pro Ile Val Glu Arg
    2745                2750                2755

ACC CCA TTC AGT TCT AGC AGC TCA AGC AAA CAC AGT TCA CCT AGT GGG       8358
Thr Pro Phe Ser Ser Ser Ser Ser Ser Lys His Ser Ser Pro Ser Gly
2760                2765                2770                2775

ACT GTT GCT GCC AGA GTG ACT CCT TTT AAT TAC AAC CCA AGC CCT AGG       8406
Thr Val Ala Ala Arg Val Thr Pro Phe Asn Tyr Asn Pro Ser Pro Arg
                2780                2785                2790

AAA AGC AGC GCA GAT AGC ACT TCA GCT CGG CCA TCT CAG ATC CCA ACT       8454
Lys Ser Ser Ala Asp Ser Thr Ser Ala Arg Pro Ser Gln Ile Pro Thr
            2795                2800                2805

CCA GTG AAT AAC AAC ACA AAG AAG CGA GAT TCC AAA ACT GAC AGC ACA       8502
Pro Val Asn Asn Asn Thr Lys Lys Arg Asp Ser Lys Thr Asp Ser Thr
        2810                2815                2820

GAA TCC AGT GGA ACC CAA AGT CCT AAG CGC CAT TCT GGG TCT TAC CTT       8550
Glu Ser Ser Gly Thr Gln Ser Pro Lys Arg His Ser Gly Ser Tyr Leu
    2825                2830                2835

GTG ACA TCT GTT TAAAAGAGAG GAAGAATGAA ACTAAGAAAA TTCTATGTTA           8602
Val Thr Ser Val
2840

ATTACAACTG CTATATAGAC ATTTTGTTTC AAATGAAACT TTAAAAGACT GAAAATTTT      8662

GTAAATAGGT TGATTCTTG TTAGAGGGTT TTTGTTCTGG AAGCCATATT TGATAGTATA      8722

CTTTGTCTTC ACTGGTCTTA TTTTGGGAGG CACTCTTGAT GGTTAGGAAA AAATAGAAAG     8782

CCAAGTATGT TTGTACAGTA TGTTTTACAT GTATTTAAAG TAGCATCCCA TCCCAACTTC     8842

CTTAATTATT GCTTGTCTAA AATAATGAAC ACTACAGATA GGAAATATGA TATATTGCTG     8902

TTATCAATCA TTTCTAGATT ATAAACTGAC TAAACTTACA TCAGGGGAAA ATTGGTATTT     8962

ATGCAAAAAA AAAATGTTTT TGTCCTTGTG AGTCCATCTA ACATCATAAT TAATCATGTG     9022

GCTGTGAAAT TCACAGTAAT ATGGTTCCCG ATGAACAAGT TTACCCAGCC TGCTTTGCTT     9082

ACTGCATGAA TGAAACTGAT GGTTCAATTT CAGAAGTAAT GATTAACAGT TATGTGGTCA     9142

CATGATGTGC ATAGAGATAG CTACAGTGTA ATAATTTACA CTATTTTGTG CTCCAAACAA     9202

AACAAAAATC TGTGTAACTG TAAAACATTG AATGAAACTA TTTTACCTGA ACTAGATTTT     9262

ATCTGAAAGT AGGTAGAATT TTTGCTATGC TGTAATTTGT TGTATATTCT GGTATTTGAG     9322

GTGAGATGGC TGCTCTTTAT TAATGAGACA TGAATTGTGT CTCAACAGAA ACTAAATGAA     9382

CATTTCAGAA TAAATTATTG CTGTATGTAA ACTGTTACTG AAATTGGTAT TGTTTGAAG      9442

GGTTTGTTTC ACATTTGTAT TAATTAATTG TTTAAAATGC CTCTTTTAAA AGCTTATATA     9502

AATTTTTTCT TCAGCTTCTA TGCATTAAGA GTAAAATTCC TCTTACTGTA ATAAAAACAT     9562
```

TGAAGAAGAC TGTTGCCACT TAACCATTCC ATGCGTTGGC ACTT                    9606

(2) INFORMATION FOR SEQ ID NO: 2:

(i) SEQUENCE CHARACTERISTICS:
        (A) LENGTH: 2843 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Ala Ser Tyr Asp Gln Leu Leu Lys Gln Val Glu Ala Leu
 1               5                  10                  15

Lys Met Glu Asn Ser Asn Leu Arg Gln Glu Leu Glu Asp Asn Ser Asn
                20                  25                  30

His Leu Thr Lys Leu Glu Thr Glu Ala Ser Asn Met Lys Glu Val Leu
            35                  40                  45

Lys Gln Leu Gln Gly Ser Ile Glu Asp Glu Ala Met Ala Ser Ser Gly
 50                  55                  60

Gln Ile Asp Leu Leu Glu Arg Leu Lys Glu Leu Asn Leu Asp Ser Ser
 65                  70                  75                  80

Asn Phe Pro Gly Val Lys Leu Arg Ser Lys Met Ser Leu Arg Ser Tyr
                85                  90                  95

Gly Ser Arg Glu Gly Ser Val Ser Ser Arg Ser Gly Glu Cys Ser Pro
            100                 105                 110

Val Pro Met Gly Ser Phe Pro Arg Arg Gly Phe Val Asn Gly Ser Arg
        115                 120                 125

Glu Ser Thr Gly Tyr Leu Glu Glu Leu Glu Lys Glu Arg Ser Leu Leu
130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Leu Gln Thr Asp Leu Thr Arg Arg Gln Leu Glu Tyr Glu
            180                 185                 190

Ala Arg Gln Ile Arg Val Ala Met Glu Glu Gln Leu Gly Thr Cys Gln
        195                 200                 205

Asp Met Glu Lys Arg Ala Gln Arg Arg Ile Ala Arg Ile Gln Gln Ile
210                 215                 220

Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
            260                 265                 270

Thr Ser Gly Asn Gly Gln Gly Ser Thr Thr Arg Met Asp His Glu Thr
        275                 280                 285

Ala Ser Val Leu Ser Ser Ser Thr His Ser Ala Pro Arg Arg Leu
290                 295                 300

Thr Ser His Leu Gly Thr Lys Val Glu Met Val Tyr Ser Leu Leu Ser
305                 310                 315                 320

Met Leu Gly Thr His Asp Lys Asp Asp Met Ser Arg Thr Leu Leu Ala
                325                 330                 335

Met Ser Ser Ser Gln Asp Ser Cys Ile Ser Met Arg Gln Ser Gly Cys
            340                 345                 350
```

-continued

```
Leu Pro Leu Leu Ile Gln Leu Leu His Gly Asn Asp Lys Asp Ser Val
        355                 360                 365
Leu Leu Gly Asn Ser Arg Gly Ser Lys Glu Ala Arg Ala Arg Ala Ser
370                 375                 380
Ala Ala Leu His Asn Ile Ile His Ser Gln Pro Asp Asp Lys Arg Gly
385                 390                 395                 400
Arg Arg Glu Ile Arg Val Leu His Leu Leu Glu Gln Ile Arg Ala Tyr
                405                 410                 415
Cys Glu Thr Cys Trp Glu Trp Gln Glu Ala His Glu Pro Gly Met Asp
            420                 425                 430
Gln Asp Lys Asn Pro Met Pro Ala Pro Val Glu His Gln Ile Cys Pro
        435                 440                 445
Ala Val Cys Val Leu Met Lys Leu Ser Phe Asp Glu Glu His Arg His
    450                 455                 460
Ala Met Asn Glu Leu Gly Gly Leu Gln Ala Ile Ala Glu Leu Leu Gln
465                 470                 475                 480
Val Asp Cys Glu Met Tyr Gly Leu Thr Asn Asp His Tyr Ser Ile Thr
                485                 490                 495
Leu Arg Arg Tyr Ala Gly Met Ala Leu Thr Asn Leu Thr Phe Gly Asp
            500                 505                 510
Val Ala Asn Lys Ala Thr Leu Cys Ser Met Lys Gly Cys Met Arg Ala
        515                 520                 525
Leu Val Ala Gln Leu Lys Ser Glu Ser Glu Asp Leu Gln Gln Val Ile
    530                 535                 540
Ala Ser Val Leu Arg Asn Leu Ser Trp Arg Ala Asp Val Asn Ser Lys
545                 550                 555                 560
Lys Thr Leu Arg Glu Val Gly Ser Val Lys Ala Leu Met Glu Cys Ala
                565                 570                 575
Leu Glu Val Lys Lys Glu Ser Thr Leu Lys Ser Val Leu Ser Ala Leu
            580                 585                 590
Trp Asn Leu Ser Ala His Cys Thr Glu Asn Lys Ala Asp Ile Cys Ala
        595                 600                 605
Val Asp Gly Ala Leu Ala Phe Leu Val Gly Thr Leu Thr Tyr Arg Ser
    610                 615                 620
Gln Thr Asn Thr Leu Ala Ile Ile Glu Ser Gly Gly Gly Ile Leu Arg
625                 630                 635                 640
Asn Val Ser Ser Leu Ile Ala Thr Asn Glu Asp His Arg Gln Ile Leu
                645                 650                 655
Arg Glu Asn Asn Cys Leu Gln Thr Leu Leu Gln His Leu Lys Ser His
            660                 665                 670
Ser Leu Thr Ile Val Ser Asn Ala Cys Gly Thr Leu Trp Asn Leu Ser
        675                 680                 685
Ala Arg Asn Pro Lys Asp Gln Glu Ala Leu Trp Asp Met Gly Ala Val
    690                 695                 700
Ser Met Leu Lys Asn Leu Ile His Ser Lys His Lys Met Ile Ala Met
705                 710                 715                 720
Gly Ser Ala Ala Ala Leu Arg Asn Leu Met Ala Asn Arg Pro Ala Lys
                725                 730                 735
Tyr Lys Asp Ala Asn Ile Met Ser Pro Gly Ser Ser Leu Pro Ser Leu
            740                 745                 750
His Val Arg Lys Gln Lys Ala Leu Glu Ala Glu Leu Asp Ala Gln His
        755                 760                 765
```

```
Leu Ser Glu Thr Phe Asp Asn Ile Asp Asn Leu Ser Pro Lys Ala Ser
    770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                805                 810                 815

Gly Asn Met Thr Val Leu Ser Pro Tyr Leu Asn Thr Thr Val Leu Pro
            820                 825                 830

Ser Ser Ser Ser Ser Arg Gly Ser Leu Asp Ser Ser Arg Ser Glu Lys
            835                 840                 845

Asp Arg Ser Leu Glu Arg Glu Arg Gly Ile Gly Leu Gly Asn Tyr His
850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Val Ser Ala
                885                 890                 895

Ile His Thr Ser Gln Glu Asp Arg Ser Ser Gly Ser Thr Thr Glu Leu
            900                 905                 910

His Cys Val Thr Asp Glu Arg Asn Ala Leu Arg Arg Ser Ser Ala Ala
            915                 920                 925

His Thr His Ser Asn Thr Tyr Asn Phe Thr Lys Ser Glu Asn Ser Asn
        930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Asn Asp Gly Tyr Gly Lys Arg
                965                 970                 975

Gly Gln Met Lys Pro Ser Ile Glu Ser Tyr Ser Glu Asp Asp Glu Ser
            980                 985                 990

Lys Phe Cys Ser Tyr Gly Gln Tyr Pro Ala Asp Leu Ala His Lys Ile
            995                 1000                1005

His Ser Ala Asn His Met Asp Asp Asn Asp Gly Glu Leu Asp Thr Pro
    1010                1015                1020

Ile Asn Tyr Ser Leu Lys Tyr Ser Asp Glu Gln Leu Asn Ser Gly Arg
1025                1030                1035                1040

Gln Ser Pro Ser Gln Asn Glu Arg Trp Ala Arg Pro Lys His Ile Ile
            1045                1050                1055

Glu Asp Glu Ile Lys Gln Ser Glu Gln Arg Gln Ser Arg Asn Gln Ser
            1060                1065                1070

Thr Thr Tyr Pro Val Tyr Thr Glu Ser Thr Asp Asp Lys His Leu Lys
        1075                1080                1085

Phe Gln Pro His Phe Gly Gln Gln Glu Cys Val Ser Pro Tyr Arg Ser
    1090                1095                1100

Arg Gly Ala Asn Gly Ser Glu Thr Asn Arg Val Gly Ser Asn His Gly
1105                1110                1115                1120

Ile Asn Gln Asn Val Ser Gln Ser Leu Cys Gln Glu Asp Asp Tyr Glu
                1125                1130                1135

Asp Asp Lys Pro Thr Asn Tyr Ser Glu Arg Tyr Ser Glu Glu Glu Gln
            1140                1145                1150

His Glu Glu Glu Glu Arg Pro Thr Asn Tyr Ser Ile Lys Tyr Asn Glu
        1155                1160                1165

Glu Lys Arg His Val Asp Gln Pro Ile Asp Tyr Ser Leu Lys Tyr Ala
    1170                1175                1180

Thr Asp Ile Pro Ser Ser Gln Lys Gln Ser Phe Ser Phe Ser Lys Ser
```

```
1185                1190                1195                1200

Ser Ser Gly Gln Ser Ser Lys Thr Glu His Met Ser Ser Ser Glu
                1205                1210                1215

Asn Thr Ser Thr Pro Ser Ser Asn Ala Lys Arg Gln Asn Gln Leu His
                1220                1225                1230

Pro Ser Ser Ala Gln Ser Arg Ser Gly Gln Pro Gln Lys Ala Ala Thr
                1235                1240                1245

Cys Lys Val Ser Ser Ile Asn Gln Glu Thr Ile Gln Thr Tyr Cys Val
                1250                1255                1260

Glu Asp Thr Pro Ile Cys Phe Ser Arg Cys Ser Ser Leu Ser Ser Leu
1265                1270                1275                1280

Ser Ser Ala Glu Asp Glu Ile Gly Cys Asn Gln Thr Thr Gln Glu Ala
                1285                1290                1295

Asp Ser Ala Asn Thr Leu Gln Ile Ala Glu Ile Lys Gly Lys Ile Gly
                1300                1305                1310

Thr Arg Ser Ala Glu Asp Pro Val Ser Glu Val Pro Ala Val Ser Gln
                1315                1320                1325

His Pro Arg Thr Lys Ser Ser Arg Leu Gln Gly Ser Ser Leu Ser Ser
                1330                1335                1340

Glu Ser Ala Arg His Lys Ala Val Glu Phe Pro Ser Gly Ala Lys Ser
1345                1350                1355                1360

Pro Ser Lys Ser Gly Ala Gln Thr Pro Lys Ser Pro Pro Glu His Tyr
                1365                1370                1375

Val Gln Glu Thr Pro Leu Met Phe Ser Arg Cys Thr Ser Val Ser Ser
                1380                1385                1390

Leu Asp Ser Phe Glu Ser Arg Ser Ile Ala Ser Ser Val Gln Ser Glu
                1395                1400                1405

Pro Cys Ser Gly Met Val Ser Gly Ile Ile Ser Pro Ser Asp Leu Pro
                1410                1415                1420

Asp Ser Pro Gly Gln Thr Met Pro Pro Ser Arg Ser Lys Thr Pro Pro
1425                1430                1435                1440

Pro Pro Pro Gln Thr Ala Gln Thr Lys Arg Glu Val Pro Lys Asn Lys
                1445                1450                1455

Ala Pro Thr Ala Glu Lys Arg Glu Ser Gly Pro Lys Gln Ala Ala Val
                1460                1465                1470

Asn Ala Ala Val Gln Arg Val Gln Val Leu Pro Asp Ala Asp Thr Leu
                1475                1480                1485

Leu His Phe Ala Thr Glu Ser Thr Pro Asp Gly Phe Ser Cys Ser Ser
                1490                1495                1500

Ser Leu Ser Ala Leu Ser Leu Asp Glu Pro Phe Ile Gln Lys Asp Val
1505                1510                1515                1520

Glu Leu Arg Ile Met Pro Pro Val Gln Glu Asn Asp Asn Gly Asn Glu
                1525                1530                1535

Thr Glu Ser Glu Gln Pro Lys Glu Ser Asn Glu Asn Gln Lys Glu
                1540                1545                1550

Ala Glu Lys Thr Ile Asp Ser Glu Lys Asp Leu Leu Asp Asp Ser Asp
                1555                1560                1565

Asp Asp Asp Ile Glu Ile Leu Glu Glu Cys Ile Ile Ser Ala Met Pro
                1570                1575                1580

Thr Lys Ser Ser Arg Lys Gly Lys Lys Pro Ala Gln Thr Ala Ser Lys
1585                1590                1595                1600

Leu Pro Pro Pro Val Ala Arg Lys Pro Ser Gln Leu Pro Val Tyr Lys
                1605                1610                1615
```

-continued

Leu Leu Pro Ser Gln Asn Arg Leu Gln Pro Gln Lys His Val Ser Phe
            1620                1625                1630

Thr Pro Gly Asp Asp Met Pro Arg Val Tyr Cys Val Glu Gly Thr Pro
            1635                1640                1645

Ile Asn Phe Ser Thr Ala Thr Ser Leu Ser Asp Leu Thr Ile Glu Ser
        1650                1655                1660

Pro Pro Asn Glu Leu Ala Ala Gly Glu Gly Val Arg Gly Gly Ala Gln
1665                1670                1675                1680

Ser Gly Glu Phe Glu Lys Arg Asp Thr Ile Pro Thr Gly Arg Ser
            1685                1690                1695

Thr Asp Glu Ala Gln Gly Gly Lys Thr Ser Ser Val Thr Ile Pro Glu
            1700                1705                1710

Leu Asp Asp Asn Lys Ala Glu Glu Gly Asp Ile Leu Ala Glu Cys Ile
            1715                1720                1725

Asn Ser Ala Met Pro Lys Gly Lys Ser His Lys Pro Phe Arg Val Lys
            1730                1735                1740

Lys Ile Met Asp Gln Val Gln Gln Ala Ser Ala Ser Ser Ser Ala Pro
1745                1750                1755                1760

Asn Lys Asn Gln Leu Asp Gly Lys Lys Lys Pro Thr Ser Pro Val
            1765                1770                1775

Lys Pro Ile Pro Gln Asn Thr Glu Tyr Arg Thr Arg Val Arg Lys Asn
            1780                1785                1790

Ala Asp Ser Lys Asn Asn Leu Asn Ala Glu Arg Val Phe Ser Asp Asn
            1795                1800                1805

Lys Asp Ser Lys Lys Gln Asn Leu Lys Asn Asn Ser Lys Asp Phe Asn
            1810                1815                1820

Asp Lys Leu Pro Asn Asn Glu Asp Arg Val Arg Gly Ser Phe Ala Phe
1825                1830                1835                1840

Asp Ser Pro His His Tyr Thr Pro Ile Glu Gly Thr Pro Tyr Cys Phe
            1845                1850                1855

Ser Arg Asn Asp Ser Leu Ser Ser Leu Asp Phe Asp Asp Asp Val
            1860                1865                1870

Asp Leu Ser Arg Glu Lys Ala Glu Leu Arg Lys Ala Lys Glu Asn Lys
            1875                1880                1885

Glu Ser Glu Ala Lys Val Thr Ser His Thr Glu Leu Thr Ser Asn Gln
            1890                1895                1900

Gln Ser Ala Asn Lys Thr Gln Ala Ile Ala Lys Gln Pro Ile Asn Arg
1905                1910                1915                1920

Gly Gln Pro Lys Pro Ile Leu Gln Lys Gln Ser Thr Phe Pro Gln Ser
            1925                1930                1935

Ser Lys Asp Ile Pro Asp Arg Gly Ala Ala Thr Asp Glu Lys Leu Gln
            1940                1945                1950

Asn Phe Ala Ile Glu Asn Thr Pro Val Cys Phe Ser His Asn Ser Ser
            1955                1960                1965

Leu Ser Ser Leu Ser Asp Ile Asp Gln Glu Asn Asn Lys Glu Asn
            1970                1975                1980

Glu Pro Ile Lys Glu Thr Glu Pro Pro Asp Ser Gln Gly Glu Pro Ser
1985                1990                1995                2000

Lys Pro Gln Ala Ser Gly Tyr Ala Pro Lys Ser Phe His Val Glu Asp
            2005                2010                2015

Thr Pro Val Cys Phe Ser Arg Asn Ser Ser Leu Ser Ser Leu Ser Ile
            2020                2025                2030

-continued

```
Asp Ser Glu Asp Asp Leu Leu Gln Cys Ile Ser Ser Ala Met Pro
        2035                2040                2045

Lys Lys Lys Lys Pro Ser Arg Leu Lys Gly Asp Asn Glu Lys His Ser
2050                2055                2060

Pro Arg Asn Met Gly Gly Ile Leu Gly Glu Asp Leu Thr Leu Asp Leu
2065                2070                2075                2080

Lys Asp Ile Gln Arg Pro Asp Ser Glu His Gly Leu Ser Pro Asp Ser
        2085                2090                2095

Glu Asn Phe Asp Trp Lys Ala Ile Gln Glu Gly Ala Asn Ser Ile Val
        2100                2105                2110

Ser Ser Leu His Gln Ala Ala Ala Ala Cys Leu Ser Arg Gln Ala
        2115                2120                2125

Ser Ser Asp Ser Asp Ser Ile Leu Ser Leu Lys Ser Gly Ile Ser Leu
        2130                2135                2140

Gly Ser Pro Phe His Leu Thr Pro Asp Gln Glu Glu Lys Pro Phe Thr
2145                2150                2155                2160

Ser Asn Lys Gly Pro Arg Ile Leu Lys Pro Gly Glu Lys Ser Thr Leu
        2165                2170                2175

Glu Thr Lys Lys Ile Glu Ser Glu Ser Lys Gly Ile Lys Gly Gly Lys
        2180                2185                2190

Lys Val Tyr Lys Ser Leu Ile Thr Gly Lys Val Arg Ser Asn Ser Glu
        2195                2200                2205

Ile Ser Gly Gln Met Lys Gln Pro Leu Gln Ala Asn Met Pro Ser Ile
    2210                2215                2220

Ser Arg Gly Arg Thr Met Ile His Ile Pro Gly Val Arg Asn Ser Ser
2225                2230                2235                2240

Ser Ser Thr Ser Pro Val Ser Lys Lys Gly Pro Pro Leu Lys Thr Pro
                2245                2250                2255

Ala Ser Lys Ser Pro Ser Glu Gly Gln Thr Ala Thr Thr Ser Pro Arg
        2260                2265                2270

Gly Ala Lys Pro Ser Val Lys Ser Glu Leu Ser Pro Val Ala Arg Gln
        2275                2280                2285

Thr Ser Gln Ile Gly Gly Ser Ser Lys Ala Pro Ser Arg Ser Gly Ser
    2290                2295                2300

Arg Asp Ser Thr Pro Ser Arg Pro Ala Gln Gln Pro Leu Ser Arg Pro
2305                2310                2315                2320

Ile Gln Ser Pro Gly Arg Asn Ser Ile Ser Pro Gly Arg Asn Gly Ile
        2325                2330                2335

Ser Pro Pro Asn Lys Leu Ser Gln Leu Pro Arg Thr Ser Ser Pro Ser
            2340                2345                2350

Thr Ala Ser Thr Lys Ser Ser Gly Ser Gly Lys Met Ser Tyr Thr Ser
        2355                2360                2365

Pro Gly Arg Gln Met Ser Gln Gln Asn Leu Thr Lys Gln Thr Gly Leu
    2370                2375                2380

Ser Lys Asn Ala Ser Ser Ile Pro Arg Ser Glu Ser Ala Ser Lys Gly
2385                2390                2395                2400

Leu Asn Gln Met Asn Asn Gly Asn Gly Ala Asn Lys Lys Val Glu Leu
                2405                2410                2415

Ser Arg Met Ser Ser Thr Lys Ser Ser Gly Ser Glu Ser Asp Arg Ser
        2420                2425                2430

Glu Arg Pro Val Leu Val Arg Gln Ser Thr Phe Ile Lys Glu Ala Pro
        2435                2440                2445

Ser Pro Thr Leu Arg Arg Lys Leu Glu Glu Ser Ala Ser Phe Glu Ser
```

```
                 2450                2455                2460
Leu Ser Pro Ser Ser Arg Pro Ala Ser Pro Thr Arg Ser Gln Ala Gln
2465                2470                2475                2480

Thr Pro Val Leu Ser Pro Ser Leu Pro Asp Met Ser Leu Ser Thr His
                2485                2490                2495

Ser Ser Val Gln Ala Gly Gly Trp Arg Lys Leu Pro Pro Asn Leu Ser
                2500                2505                2510

Pro Thr Ile Glu Tyr Asn Asp Gly Arg Pro Ala Lys Arg His Asp Ile
            2515                2520                2525

Ala Arg Ser His Ser Glu Ser Pro Ser Arg Leu Pro Ile Asn Arg Ser
            2530                2535                2540

Gly Thr Trp Lys Arg Glu His Ser Lys His Ser Ser Ser Leu Pro Arg
2545                2550                2555                2560

Val Ser Thr Trp Arg Arg Thr Gly Ser Ser Ser Ile Leu Ser Ala
                2565                2570                2575

Ser Ser Glu Ser Ser Glu Lys Ala Lys Ser Glu Asp Glu Lys His Val
            2580                2585                2590

Asn Ser Ile Ser Gly Thr Lys Gln Ser Lys Glu Asn Gln Val Ser Ala
            2595                2600                2605

Lys Gly Thr Trp Arg Lys Ile Lys Glu Asn Glu Phe Ser Pro Thr Asn
2610                2615                2620

Ser Thr Ser Gln Thr Val Ser Ser Gly Ala Thr Asn Gly Ala Glu Ser
2625                2630                2635                2640

Lys Thr Leu Ile Tyr Gln Met Ala Pro Ala Val Ser Lys Thr Glu Asp
            2645                2650                2655

Val Trp Val Arg Ile Glu Asp Cys Pro Ile Asn Asn Pro Arg Ser Gly
            2660                2665                2670

Arg Ser Pro Thr Gly Asn Thr Pro Pro Val Ile Asp Ser Val Ser Glu
            2675                2680                2685

Lys Ala Asn Pro Asn Ile Lys Asp Ser Lys Asp Asn Gln Ala Lys Gln
            2690                2695                2700

Asn Val Gly Asn Gly Ser Val Pro Met Arg Thr Val Gly Leu Glu Asn
2705                2710                2715                2720

Arg Leu Thr Ser Phe Ile Gln Val Asp Ala Pro Asp Gln Lys Gly Thr
            2725                2730                2735

Glu Ile Lys Pro Gly Gln Asn Asn Pro Val Pro Val Ser Glu Thr Asn
            2740                2745                2750

Glu Ser Pro Ile Val Glu Arg Thr Pro Phe Ser Ser Ser Ser Ser Ser
            2755                2760                2765

Lys His Ser Ser Pro Ser Gly Thr Val Ala Ala Arg Val Thr Pro Phe
            2770                2775                2780

Asn Tyr Asn Pro Ser Pro Arg Lys Ser Ser Ala Asp Ser Thr Ser Ala
2785                2790                2795                2800

Arg Pro Ser Gln Ile Pro Thr Pro Val Asn Asn Asn Thr Lys Lys Arg
            2805                2810                2815

Asp Ser Lys Thr Asp Ser Thr Glu Ser Ser Gly Thr Gln Ser Pro Lys
            2820                2825                2830

Arg His Ser Gly Ser Tyr Leu Val Thr Ser Val
            2835                2840
```

(2) INFORMATION FOR SEQ ID NO: 3:

(i) SEQUENCE CHARACTERISTICS:
        (A) LENGTH: 3172 base pairs (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Homo sapiens (vii) IMMEDIATE SOURCE:
        (B) CLONE: DP1(TB2)

(ix) FEATURE:
        (A) NAME/KEY: CDS
        (B) LOCATION: 1..630

(xi) SEQUENCE DESCRIPTION: SEQ ID NO: 3:

```
GCA GTC GCC GCT CCA GTC TAT CCG GCA CTA GGA ACA GCC CCG GGN GGC      48
Ala Val Ala Ala Pro Val Tyr Pro Ala Leu Gly Thr Ala Pro Gly Gly
 1               5                  10                  15

GAG ACG GTC CCC GCC ATG TCT GCG GCC ATG AGG GAG AGG TTC GAC CGG      96
Glu Thr Val Pro Ala Met Ser Ala Ala Met Arg Glu Arg Phe Asp Arg
                 20                  25                  30

TTC CTG CAC GAG AAG AAC TGC ATG ACT GAC CTT CTG GCC AAG CTC GAG     144
Phe Leu His Glu Lys Asn Cys Met Thr Asp Leu Leu Ala Lys Leu Glu
             35                  40                  45

GCC AAA ACC GGC GTG AAC AGG AGC TTC ATC GCT CTT GGT GTC ATC GGA     192
Ala Lys Thr Gly Val Asn Arg Ser Phe Ile Ala Leu Gly Val Ile Gly
 50                  55                  60

CTG GTG GCC TTG TAC CTG GTG TTC GGT TAT GGA GCC TCT CTC CTC TGC     240
Leu Val Ala Leu Tyr Leu Val Phe Gly Tyr Gly Ala Ser Leu Leu Cys
 65                  70                  75                  80

AAC CTG ATA GGA TTT GGC TAC CCA GCC TAC ATC TCA ATT AAA GCT ATA     288
Asn Leu Ile Gly Phe Gly Tyr Pro Ala Tyr Ile Ser Ile Lys Ala Ile
                 85                  90                  95

GAG AGT CCC AAC AAA GAA GAT GAT ACC CAG TGG CTG ACC TAC TGG GTA     336
Glu Ser Pro Asn Lys Glu Asp Asp Thr Gln Trp Leu Thr Tyr Trp Val
                100                 105                 110

GTG TAT GGT GTG TTC AGC ATT GCT GAA TTC TTC TCT GAT ATC TTC CTG     384
Val Tyr Gly Val Phe Ser Ile Ala Glu Phe Phe Ser Asp Ile Phe Leu
            115                 120                 125

TCA TGG TTC CCC TTC TAC TAC ATG CTG AAG TGT GGC TTC CTG TTG TGG     432
Ser Trp Phe Pro Phe Tyr Tyr Met Leu Lys Cys Gly Phe Leu Leu Trp
        130                 135                 140

TGC ATG GCC CCG AGC CCT TCT AAT GGG GCT GAA CTG CTC TAC AAG CGC     480
Cys Met Ala Pro Ser Pro Ser Asn Gly Ala Glu Leu Leu Tyr Lys Arg
145                 150                 155                 160

ATC ATC CGT CCT TTC TTC CTG AAG CAC GAG TCC CAG ATG GAC AGT GTG     528
Ile Ile Arg Pro Phe Phe Leu Lys His Glu Ser Gln Met Asp Ser Val
                165                 170                 175

GTC AAG GAC CTT AAA GAC AAG TCC AAA GAG ACT GCA GAT GCC ATC ACT     576
Val Lys Asp Leu Lys Asp Lys Ser Lys Glu Thr Ala Asp Ala Ile Thr
                180                 185                 190

AAA GAA GCG AAG AAA GCT ACC GTG AAT TTA CTG GGT GAA GAA AAG AAG     624
Lys Glu Ala Lys Lys Ala Thr Val Asn Leu Leu Gly Glu Glu Lys Lys
            195                 200                 205

AGC ACC TAAACCAGAC TAAACCAGAC TGGATGGAAA CTTCCTGCCC TCTCTGTACC      680
Ser Thr
    210

TTCCTACTGG AGCTTGATGT TATATTAGGG ACTGTGGTAT AATTATTTTA ATAATGTTGC    740

CTTGGAAACA TTTTTGAGAT ATTAAAGATT GGAATGTGTT GTAAGTTTCT TTGCTTACTT    800

TTACTGTCTA TATATATAGG GAGCACTTTA AACTTAATGC AGTGGGCAGT GTCCACGTTT    860
```

```
TTGGAAAATG TATTTTGCCT CTGGGTAGGA AAAGATGTAT GTTGCTATCC TGCAGGAAAT    920

ATAAACTTAA AATAAAATTA TATACCCCAC AGGCTGTGTA CTTTACTGGG CTCTCCCTGC    980

ACGSATTTTC TCTGTAGTTA CATTTAGGRT AATCTTTATG GTTCTACTTC CTRTAATGTA   1040

CAATTTTATA TAATTCNGRA ATGTTTTTAA TGTATTTGTG CACATGTACA TATGGAAATG   1100

TTACTGTCTG ACTACANCAT GCATCATGCT CATGGGGAGG GAGCAGGGGA AGGTTGTATG   1160

TGTCATTTAT AACTTCTGTA CAGTAAGACC ACCTGCCAAA AGCTGGAGGA ACCATTGTGC   1220

TGGTGTGGTC TACTAAATAA TACTTTAGGA AATACGTGAT TAATATGCAA GTGAACAAAG   1280

TGAGAAATGA AATCGAATGG AGATTGGCCT GGTTGTTTCC GTAGTATATG GCATATGAAT   1340

ACCAGGATAG CTTTATAAAG CAGTTAGTTA GTTAGTTACT CACTCAGTG ATAAATCGGG    1400

AAATTTACAC ACACACACAC ACACACACAC ACACACACAC ACACACACAG              1460

AGTACCCTGT AACTCTCAAT TCCCTGAAAA ACTAGTAATA CTGTCTTATC TGCTATAAAC   1520

TTTACATATT TGTCTATTGT CAAGATGCTA CANTGGAMNC CATTTCTGGT TTTATCTTCA   1580

NAGSGGAGAN ACATGTTGAT TTAGTCTTCT TTCCCAATCT TCTTTTTTAA MCCAGTTTNA   1640

GGMNCTTCTG RAGATTTGYC CACCTCTGAT TACATGTATG TTCTYGTTTG TATCATKAGC   1700

AACAACATGC TAATGRCGAC ACCTAGCTCT RAGMGCAATT CTGGGAGANT GARAGGNWGT   1760

ATARAGTMNC CCATAATCTG CTTGGCAATA GTTAAGTCAA TCTATCTTCA GTTTTTCTCT   1820

GGCCTTTAAG GTCAAACACA AGAGGCTTCC CTAGTTTACA AGTCAGAGTC ACTTGTAGTC   1880

CATTTAAATG CCCTCATCCG TATTCTTTGT GTTGATAAGC TGCACAKGAC TACATAGTAA   1940

GTACAGANCA GTAAAGTTAA NNCGGATGTC TCCATTGATC TGCCAANTCG NTATAGAGAG   2000

CAATTTGTCT GGACTAGAAA ATCTGAGTTT TACACCATAC TGTTAAGAGT CCTTTTGAAT   2060

TAAACTAGAC TAAAACAAGT GTATAACTAA ACTAACAAGA TTAAATATCC AGCCAGTACA   2120

GTATTTTTA AGGCAAATAA AGATGATTAG CTCACCTTGA GNTAACAATC AGGTAAGATC    2180

ATNACAATGT CTCATGATGT NAANAATATT AAAGATATCA ATACTAAGTG ACAGTATCAC   2240

NNCTAATATA ATATGGATCA GAGCATTTAT TTTGGGGAGG AAAACAGTGG TGATTACCGG   2300

CATTTTATTA AACTTAAAAC TTTGTAGAAA GCAAACAAAA TTGTTCTTGG GAGAAAATCA   2360

ACTTTTAGAT TAAAAAAATT TTAAGTAWCT AGGAGTATTT AAATCCTTTT CCCATAAATA   2420

AAAGTACAGT TTTCTTGGTG GCAGAATGAA AATCAGCAAC NTCTAGCATA TAGACTATAT   2480

AATCAGATTG ACAGCATATA GAATATATTA TCAGACAAGA TGAGGAGGTA CAAAAGTTAC   2540

TATTGCTCAT AATGACTTAC AGGCTAAAAN TAGNTNTAAA ATACTATATT AAATTCTGAA   2600

TGCAATTTTT TTTTGTTCCC TTGAGACCAA AATTTAAGTT AACTGTTGCT GGCAGTCTAA   2660

GTGTAAATGT TAACAGCAGG AGAAGTTAAG AATTGAGCAG TTCTGTTGCA TGATTTCCCA   2720

AATGAAATAC TGCCTTGGCT AGAGTTTGAA AAACTAATTG AGCCTGTGCC TGGCTAGAAA   2780

ACAAGCGTTT ATTTGAATGT GAATAGTGTT TCAAAGGTAT GTAGTTACAG AATTCCTACC   2840

AAACAGCTTA AATTCTTCAA GAAAGAATTC CTGCAGCAGT TATTCCCTTA CCTGAAGGCT   2900

TCAATCATTT GGATCAACAA CTGCTACTCT CGGGAAGACT CCTCTACTCA CAGCTGAAGA   2960

AAATGAGCAC ACCCTTCACA CTGTTATCAC CTATCCTGAA GATGTGATAC ACTGAATGGA   3020

AATAAATAGA TGTAAATAAA ATTGAGWTCT CATTTAAAAA AAACCATGTG CCCAATGGGA   3080

AAATGACCTC ATGTTGTGGT TTAAACAGCA ACTGCACCCA CTAGCACAGC CCATTGAGCT   3140

ANCCTATATA TACATCTCTG TCAGTGCCCC TC                                 3172
```

(2) INFORMATION FOR SEQ ID NO: 4:

(i) SEQUENCE CHARACTERISTICS:
        (A) LENGTH: 210 amino acids
        (B) TYPE: amino acid
        (D) TOPOLOGY: linear (ii) MOLECULE TYPE: protein (xi) SEQUENCE DESCRIPTION: SEQ ID NO: 4:

```
Ala Val Ala Ala Pro Val Tyr Pro Ala Leu Gly Thr Ala Pro Gly Gly
 1               5                  10                  15

Glu Thr Val Pro Ala Met Ser Ala Ala Met Arg Glu Arg Phe Asp Arg
                20                  25                  30

Phe Leu His Glu Lys Asn Cys Met Thr Asp Leu Leu Ala Lys Leu Glu
            35                  40                  45

Ala Lys Thr Gly Val Asn Arg Ser Phe Ile Ala Leu Gly Val Ile Gly
        50                  55                  60

Leu Val Ala Leu Tyr Leu Val Phe Gly Tyr Gly Ala Ser Leu Leu Cys
65                  70                  75                  80

Asn Leu Ile Gly Phe Gly Tyr Pro Ala Tyr Ile Ser Ile Lys Ala Ile
                85                  90                  95

Glu Ser Pro Asn Lys Glu Asp Asp Thr Gln Trp Leu Thr Tyr Trp Val
               100                 105                 110

Val Tyr Gly Val Phe Ser Ile Ala Glu Phe Phe Ser Asp Ile Phe Leu
           115                 120                 125

Ser Trp Phe Pro Phe Tyr Tyr Met Leu Lys Cys Gly Phe Leu Leu Trp
       130                 135                 140

Cys Met Ala Pro Ser Pro Ser Asn Gly Ala Glu Leu Leu Tyr Lys Arg
145                 150                 155                 160

Ile Ile Arg Pro Phe Phe Leu Lys His Glu Ser Gln Met Asp Ser Val
                165                 170                 175

Val Lys Asp Leu Lys Asp Lys Ser Lys Glu Thr Ala Asp Ala Ile Thr
            180                 185                 190

Lys Glu Ala Lys Lys Ala Thr Val Asn Leu Leu Gly Glu Glu Lys Lys
        195                 200                 205

Ser Thr
    210
```

(2) INFORMATION FOR SEQ ID NO: 5:

(i) SEQUENCE CHARACTERISTICS:
        (A) LENGTH: 434 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (vii) IMMEDIATE SOURCE:
        (B) CLONE: TB1

(xi) SEQUENCE DESCRIPTION: SEQ ID NO: 5:

```
Val Ala Pro Val Val Gly Ser Gly Arg Ala Pro Arg His Pro Ala
 1               5                  10                  15

Pro Ala Ala Met His Pro Arg Arg Pro Asp Gly Phe Asp Gly Leu Gly
                20                  25                  30
```

Tyr Arg Gly Gly Ala Arg Asp Glu Gln Gly Phe Gly Gly Ala Phe Pro
            35                  40                  45

Ala Arg Ser Phe Ser Thr Gly Ser Asp Leu Gly His Trp Val Thr Thr
        50                  55                  60

Pro Pro Asp Ile Pro Gly Ser Arg Asn Leu His Trp Gly Glu Lys Ser
65                  70                  75                  80

Pro Pro Tyr Gly Val Pro Thr Thr Ser Thr Pro Tyr Glu Gly Pro Thr
                85                  90                  95

Glu Glu Pro Phe Ser Ser Gly Gly Gly Ser Val Gln Gly Gln Ser
                100                 105                 110

Ser Glu Gln Leu Asn Arg Phe Ala Gly Phe Gly Ile Gly Leu Ala Ser
            115                 120                 125

Leu Phe Thr Glu Asn Val Leu Ala His Pro Cys Ile Val Leu Arg Arg
        130                 135                 140

Gln Cys Gln Val Asn Tyr His Ala Gln His Tyr His Leu Thr Pro Phe
145                 150                 155                 160

Thr Val Ile Asn Ile Met Tyr Ser Phe Asn Lys Thr Gln Gly Pro Arg
                165                 170                 175

Ala Leu Trp Lys Gly Met Gly Ser Thr Phe Ile Val Gln Gly Val Thr
                180                 185                 190

Leu Gly Ala Glu Gly Ile Ile Ser Glu Phe Thr Pro Leu Pro Arg Glu
            195                 200                 205

Val Leu His Lys Trp Ser Pro Lys Gln Ile Gly Glu His Leu Leu Leu
        210                 215                 220

Lys Ser Leu Thr Tyr Val Val Ala Met Pro Phe Tyr Ser Ala Ser Leu
225                 230                 235                 240

Ile Glu Thr Val Gln Ser Glu Ile Ile Arg Asp Asn Thr Gly Ile Leu
                245                 250                 255

Glu Cys Val Lys Glu Gly Ile Gly Arg Val Ile Gly Met Gly Val Pro
                260                 265                 270

His Ser Lys Arg Leu Leu Pro Leu Leu Ser Leu Ile Phe Pro Thr Val
            275                 280                 285

Leu His Gly Val Leu His Tyr Ile Ile Ser Ser Val Ile Gln Lys Phe
        290                 295                 300

Val Leu Leu Ile Leu Lys Arg Lys Thr Tyr Asn Ser His Leu Ala Glu
305                 310                 315                 320

Ser Thr Ser Pro Val Gln Ser Met Leu Asp Ala Tyr Phe Pro Glu Leu
                325                 330                 335

Ile Ala Asn Phe Ala Ala Ser Leu Cys Ser Asp Val Ile Leu Tyr Pro
                340                 345                 350

Leu Glu Thr Val Leu His Arg Leu His Ile Gln Gly Thr Arg Thr Ile
            355                 360                 365

Ile Asp Asn Thr Asp Leu Gly Tyr Glu Val Leu Pro Ile Asn Thr Gln
        370                 375                 380

Tyr Glu Gly Met Arg Asp Cys Ile Asn Thr Ile Arg Gln Glu Glu Gly
385                 390                 395                 400

Val Phe Gly Phe Tyr Lys Gly Phe Gly Ala Val Ile Ile Gln Tyr Thr
                405                 410                 415

Leu His Ala Ala Val Leu Gln Ile Thr Lys Ile Ile Tyr Ser Thr Leu
            420                 425                 430

Leu Gln (2) INFORMATION FOR SEQ ID NO: 6:

(i) SEQUENCE CHARACTERISTICS:
    (A) LENGTH: 185 amino acids
    (B) TYPE: amino acid
    (C) STRANDEDNESS: single
    (D) TOPOLOGY: linear (ii) MOLECULE TYPE: protein (vi) ORIGINAL SOURCE:
    (A) ORGANISM: Homo sapiens (vii) IMMEDIATE SOURCE:
    (B) CLONE: YS-39(TB2)

(xi) SEQUENCE DESCRIPTION: SEQ ID NO: 6:

Glu Leu Arg Arg Phe Asp Arg Phe Leu His Glu Lys Asn Cys Met Thr
1               5                   10                  15

Asp Leu Leu Ala Lys Leu Glu Ala Lys Thr Gly Val Asn Arg Ser Phe
            20                  25                  30

Ile Ala Leu Gly Val Ile Gly Leu Val Ala Leu Tyr Leu Val Phe Gly
        35                  40                  45

Tyr Gly Ala Ser Leu Leu Cys Asn Leu Ile Gly Phe Gly Tyr Pro Ala
    50                  55                  60

Tyr Ile Ser Ile Lys Ala Ile Glu Ser Pro Asn Lys Glu Asp Asp Thr
65                  70                  75                  80

Gln Trp Leu Thr Tyr Trp Val Val Tyr Gly Val Phe Ser Ile Ala Glu
                85                  90                  95

Phe Phe Ser Asp Ile Phe Leu Ser Trp Phe Pro Phe Tyr Tyr Ile Leu
                100                 105                 110

Lys Cys Gly Phe Leu Leu Trp Cys Met Ala Pro Ser Pro Ser Asn Gly
            115                 120                 125

Ala Glu Leu Leu Tyr Lys Arg Ile Ile Arg Pro Phe Phe Leu Lys His
    130                 135                 140

Glu Ser Gln Met Asp Ser Val Val Lys Asp Leu Lys Asp Lys Ala Lys
145                 150                 155                 160

Glu Thr Ala Asp Ala Ile Thr Lys Glu Ala Lys Ala Thr Val Asp
                165                 170                 175

Leu Leu Gly Glu Glu Lys Lys Ser Thr
            180                 185

(2) INFORMATION FOR SEQ ID NO: 7:

(i) SEQUENCE CHARACTERISTICS:
        (A) LENGTH: 2842 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (vii) IMMEDIATE SOURCE:
        (B) CLONE: APC (xi) SEQUENCE DESCRIPTION: SEQ ID NO: 7:

Met Ala Ala Ala Ser Tyr Asp Gln Leu Leu Lys Gln Val Glu Ala Leu
1               5                   10                  15

Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu

-continued

```
              35                  40                  45
Lys Gln Leu Gln Gly Ser Ile Glu Asp Glu Ala Met Ala Ser Ser Gly
             50                  55                  60
Gln Ile Asp Leu Leu Glu Arg Leu Lys Glu Leu Asn Leu Asp Ser Ser
 65                  70                  75                  80
Asn Phe Pro Gly Val Lys Leu Arg Ser Lys Met Ser Leu Arg Ser Tyr
                     85                  90                  95
Gly Ser Arg Glu Gly Ser Val Ser Ser Arg Ser Gly Glu Cys Ser Pro
                    100                 105                 110
Val Pro Met Gly Ser Phe Pro Arg Gly Phe Val Asn Gly Ser Arg
                115                 120                 125
Glu Ser Thr Gly Tyr Leu Glu Glu Leu Glu Lys Glu Arg Ser Leu Leu
            130                 135                 140
Leu Ala Asp Leu Asp Lys Glu Glu Lys Glu Lys Asp Trp Tyr Tyr Ala
145                 150                 155                 160
Gln Leu Gln Asn Leu Thr Lys Arg Ile Asp Ser Leu Leu Thr Glu Asn
                165                 170                 175
Phe Ser Leu Gln Thr Asp Met Thr Arg Arg Gln Leu Glu Tyr Glu Ala
            180                 185                 190
Arg Gln Ile Arg Val Ala Met Glu Glu Gln Leu Gly Thr Cys Gln Asp
        195                 200                 205
Met Glu Lys Arg Ala Gln Arg Arg Ile Ala Arg Ile Gln Gln Ile Glu
    210                 215                 220
Lys Asp Ile Leu Arg Ile Arg Gln Leu Leu Gln Ser Gln Ala Thr Glu
225                 230                 235                 240
Ala Glu Arg Ser Ser Gln Asn Lys His Glu Thr Gly Ser His Asp Ala
                245                 250                 255
Glu Arg Gln Asn Glu Gly Gln Gly Val Gly Glu Ile Asn Met Ala Thr
            260                 265                 270
Ser Gly Asn Gly Gln Gly Ser Thr Thr Arg Met Asp His Glu Thr Ala
        275                 280                 285
Ser Val Leu Ser Ser Ser Thr His Ser Ala Pro Arg Arg Leu Thr
    290                 295                 300
Ser His Leu Gly Thr Lys Val Glu Met Val Tyr Ser Leu Leu Ser Met
305                 310                 315                 320
Leu Gly Thr His Asp Lys Asp Met Ser Arg Thr Leu Leu Ala Met
                325                 330                 335
Ser Ser Ser Gln Asp Ser Cys Ile Ser Met Arg Gln Ser Gly Cys Leu
            340                 345                 350
Pro Leu Leu Ile Gln Leu Leu His Gly Asn Asp Lys Asp Ser Val Leu
        355                 360                 365
Leu Gly Asn Ser Arg Gly Ser Lys Glu Ala Arg Ala Arg Ala Ser Ala
    370                 375                 380
Ala Leu His Asn Ile Ile His Ser Gln Pro Asp Asp Lys Arg Gly Arg
385                 390                 395                 400
Arg Glu Ile Arg Val Leu His Leu Leu Glu Gln Ile Arg Ala Tyr Cys
                405                 410                 415
Glu Thr Cys Trp Glu Trp Gln Glu Ala His Glu Pro Gly Met Asp Gln
            420                 425                 430
Asp Lys Asn Pro Met Pro Ala Pro Val Glu His Gln Ile Cys Pro Ala
        435                 440                 445
Val Cys Val Leu Met Lys Leu Ser Phe Asp Glu Glu His Arg His Ala
    450                 455                 460
```

-continued

```
Met Asn Glu Leu Gly Gly Leu Gln Ala Ile Ala Glu Leu Leu Gln Val
465                 470                 475                 480

Asp Cys Glu Met Tyr Gly Leu Thr Asn Asp His Tyr Ser Ile Thr Leu
                485                 490                 495

Arg Arg Tyr Ala Gly Met Ala Leu Thr Asn Leu Thr Phe Gly Asp Val
                500                 505                 510

Ala Asn Lys Ala Thr Leu Cys Ser Met Lys Gly Cys Met Arg Ala Leu
                515                 520                 525

Val Ala Gln Leu Lys Ser Glu Ser Glu Asp Leu Gln Gln Val Ile Ala
        530                 535                 540

Ser Val Leu Arg Asn Leu Ser Trp Arg Ala Asp Val Asn Ser Lys Lys
545                 550                 555                 560

Thr Leu Arg Glu Val Gly Ser Val Lys Ala Leu Met Glu Cys Ala Leu
                565                 570                 575

Glu Val Lys Lys Glu Ser Thr Leu Lys Ser Val Leu Ser Ala Leu Trp
                580                 585                 590

Asn Leu Ser Ala His Cys Thr Glu Asn Lys Ala Asp Ile Cys Ala Val
                595                 600                 605

Asp Gly Ala Leu Ala Phe Leu Val Gly Thr Leu Thr Tyr Arg Ser Gln
        610                 615                 620

Thr Asn Thr Leu Ala Ile Ile Glu Ser Gly Gly Gly Ile Leu Arg Asn
625                 630                 635                 640

Val Ser Ser Leu Ile Ala Thr Asn Glu Asp His Arg Gln Ile Leu Arg
                645                 650                 655

Glu Asn Asn Cys Leu Gln Thr Leu Leu Gln His Leu Lys Ser His Ser
                660                 665                 670

Leu Thr Ile Val Ser Asn Ala Cys Gly Thr Leu Trp Asn Leu Ser Ala
        675                 680                 685

Arg Asn Pro Lys Asp Gln Glu Ala Leu Trp Asp Met Gly Ala Val Ser
        690                 695                 700

Met Leu Lys Asn Leu Ile His Ser Lys His Lys Met Ile Ala Met Gly
705                 710                 715                 720

Ser Ala Ala Leu Arg Asn Leu Met Ala Asn Arg Pro Ala Lys Tyr
                725                 730                 735

Lys Asp Ala Asn Ile Met Ser Pro Gly Ser Ser Leu Pro Ser Leu His
                740                 745                 750

Val Arg Lys Gln Lys Ala Leu Glu Ala Glu Leu Asp Ala Gln His Leu
        755                 760                 765

Ser Glu Thr Phe Asp Asn Ile Asp Asn Leu Ser Pro Lys Ala Ser His
770                 775                 780

Arg Ser Lys Gln Arg His Lys Gln Ser Leu Tyr Gly Asp Tyr Val Phe
785                 790                 795                 800

Asp Thr Asn Arg His Asp Asp Asn Arg Ser Asp Asn Phe Asn Thr Gly
                805                 810                 815

Asn Met Thr Val Leu Ser Pro Tyr Leu Asn Thr Thr Val Leu Pro Ser
                820                 825                 830

Ser Ser Ser Ser Arg Gly Ser Leu Asp Ser Ser Arg Ser Glu Lys Asp
                835                 840                 845

Arg Ser Leu Glu Arg Glu Arg Gly Ile Gly Leu Gly Asn Tyr His Pro
        850                 855                 860

Ala Thr Glu Asn Pro Gly Thr Ser Ser Lys Arg Gly Leu Gln Ile Ser
865                 870                 875                 880
```

```
Thr Thr Ala Ala Gln Ile Ala Lys Val Met Glu Glu Val Ser Ala Ile
             885                 890                 895

His Thr Ser Gln Glu Asp Arg Ser Ser Gly Ser Thr Thr Glu Leu His
            900                 905                 910

Cys Val Thr Asp Glu Arg Asn Ala Leu Arg Arg Ser Ser Ala Ala His
            915                 920                 925

Thr His Ser Asn Thr Tyr Asn Phe Thr Lys Ser Glu Asn Ser Asn Arg
        930                 935                 940

Thr Cys Ser Met Pro Tyr Ala Lys Leu Glu Tyr Lys Arg Ser Ser Asn
945                 950                 955                 960

Asp Ser Leu Asn Ser Val Ser Ser Asp Gly Tyr Gly Lys Arg Gly
                965                 970                 975

Gln Met Lys Pro Ser Ile Glu Ser Tyr Ser Glu Asp Asp Ser Lys
            980                 985                 990

Phe Cys Ser Tyr Gly Gln Tyr Pro Ala Asp Leu Ala His Lys Ile His
            995                 1000                1005

Ser Ala Asn His Met Asp Asp Asn Asp Gly Glu Leu Asp Thr Pro Ile
    1010                1015                1020

Asn Tyr Ser Leu Lys Tyr Ser Asp Glu Gln Leu Asn Ser Gly Arg Gln
1025                1030                1035                1040

Ser Pro Ser Gln Asn Glu Arg Trp Ala Arg Pro Lys His Ile Ile Glu
            1045                1050                1055

Asp Glu Ile Lys Gln Ser Glu Gln Arg Gln Ser Arg Asn Gln Ser Thr
            1060                1065                1070

Thr Tyr Pro Val Tyr Thr Glu Ser Thr Asp Asp Lys His Leu Lys Phe
            1075                1080                1085

Gln Pro His Phe Gly Gln Glu Cys Val Ser Pro Tyr Arg Ser Arg
            1090                1095                1100

Gly Ala Asn Gly Ser Glu Thr Asn Arg Val Gly Ser Asn His Gly Ile
1105                1110                1115                1120

Asn Gln Asn Val Ser Gln Ser Leu Cys Gln Glu Asp Asp Tyr Glu Asp
            1125                1130                1135

Asp Lys Pro Thr Asn Tyr Ser Glu Arg Tyr Ser Glu Glu Glu Gln His
            1140                1145                1150

Glu Glu Glu Glu Arg Pro Thr Asn Tyr Ser Ile Lys Tyr Asn Glu Glu
            1155                1160                1165

Lys Arg His Val Asp Gln Pro Ile Asp Tyr Ser Leu Lys Tyr Ala Thr
            1170                1175                1180

Asp Ile Pro Ser Ser Gln Lys Gln Ser Phe Ser Phe Ser Lys Ser Ser
1185                1190                1195                1200

Ser Gly Gln Ser Ser Lys Thr Glu His Met Ser Ser Ser Glu Asn
            1205                1210                1215

Thr Ser Thr Pro Ser Ser Asn Ala Lys Arg Gln Asn Gln Leu His Pro
            1220                1225                1230

Ser Ser Ala Gln Ser Arg Ser Gly Gln Pro Gln Lys Ala Ala Thr Cys
            1235                1240                1245

Lys Val Ser Ser Ile Asn Gln Glu Thr Ile Gln Thr Tyr Cys Val Glu
            1250                1255                1260

Asp Thr Pro Ile Cys Phe Ser Arg Cys Ser Ser Leu Ser Ser Leu Ser
1265                1270                1275                1280

Ser Ala Glu Asp Glu Ile Gly Cys Asn Gln Thr Thr Gln Glu Ala Asp
            1285                1290                1295

Ser Ala Asn Thr Leu Gln Ile Ala Glu Ile Lys Glu Lys Ile Gly Thr
```

-continued

```
                1300                1305                1310
Arg Ser Ala Glu Asp Pro Val Ser Glu Val Pro Ala Val Ser Gln His
            1315                1320                1325
Pro Arg Thr Lys Ser Ser Arg Leu Gln Gly Ser Ser Leu Ser Ser Glu
            1330                1335                1340
Ser Ala Arg His Lys Ala Val Glu Phe Ser Ser Gly Ala Lys Ser Pro
1345                1350                1355                1360
Ser Lys Ser Gly Ala Gln Thr Pro Lys Ser Pro Pro Glu His Tyr Val
            1365                1370                1375
Gln Glu Thr Pro Leu Met Phe Ser Arg Cys Thr Ser Val Ser Ser Leu
            1380                1385                1390
Asp Ser Phe Glu Ser Arg Ser Ile Ala Ser Ser Val Gln Ser Glu Pro
            1395                1400                1405
Cys Ser Gly Met Val Ser Gly Ile Ile Ser Pro Ser Asp Leu Pro Asp
            1410                1415                1420
Ser Pro Gly Gln Thr Met Pro Pro Ser Arg Ser Lys Thr Pro Pro Pro
1425                1430                1435                1440
Pro Pro Gln Thr Ala Gln Thr Lys Arg Glu Val Pro Lys Asn Lys Ala
            1445                1450                1455
Pro Thr Ala Glu Lys Arg Glu Ser Gly Pro Lys Gln Ala Ala Val Asn
            1460                1465                1470
Ala Ala Val Gln Arg Val Gln Val Leu Pro Asp Ala Asp Thr Leu Leu
            1475                1480                1485
His Phe Ala Thr Glu Ser Thr Pro Asp Gly Phe Ser Cys Ser Ser Ser
            1490                1495                1500
Leu Ser Ala Leu Ser Leu Asp Glu Pro Phe Ile Gln Lys Asp Val Glu
1505                1510                1515                1520
Leu Arg Ile Met Pro Pro Val Gln Glu Asn Asp Asn Gly Asn Glu Thr
            1525                1530                1535
Glu Ser Glu Gln Pro Lys Glu Ser Asn Glu Asn Gln Glu Lys Glu Ala
            1540                1545                1550
Glu Lys Thr Ile Asp Ser Glu Lys Asp Leu Leu Asp Asp Ser Asp Asp
            1555                1560                1565
Asp Asp Ile Glu Ile Leu Glu Glu Cys Ile Ile Ser Ala Met Pro Thr
            1570                1575                1580
Lys Ser Ser Arg Lys Ala Lys Lys Pro Ala Gln Thr Ala Ser Lys Leu
1585                1590                1595                1600
Pro Pro Pro Val Ala Arg Lys Pro Ser Gln Leu Pro Val Tyr Lys Leu
            1605                1610                1615
Leu Pro Ser Gln Asn Arg Leu Gln Pro Gln Lys His Val Ser Phe Thr
            1620                1625                1630
Pro Gly Asp Asp Met Pro Arg Val Tyr Cys Val Glu Gly Thr Pro Ile
            1635                1640                1645
Asn Phe Ser Thr Ala Thr Ser Leu Ser Asp Leu Thr Ile Glu Ser Pro
            1650                1655                1660
Pro Asn Glu Leu Ala Ala Gly Glu Gly Val Arg Gly Gly Ala Gln Ser
1665                1670                1675                1680
Gly Glu Phe Glu Lys Arg Asp Thr Ile Pro Thr Glu Gly Arg Ser Thr
            1685                1690                1695
Asp Glu Ala Gln Gly Gly Lys Thr Ser Ser Val Thr Ile Pro Glu Leu
            1700                1705                1710
Asp Asp Asn Lys Ala Glu Glu Gly Asp Ile Leu Ala Glu Cys Ile Asn
            1715                1720                1725
```

```
Ser Ala Met Pro Lys Gly Lys Ser His Lys Pro Phe Arg Val Lys Lys
    1730                1735                1740
Ile Met Asp Gln Val Gln Gln Ala Ser Ala Ser Ser Ser Ala Pro Asn
1745                1750                1755                1760
Lys Asn Gln Leu Asp Gly Lys Lys Lys Pro Thr Ser Pro Val Lys
                1765                1770                1775
Pro Ile Pro Gln Asn Thr Glu Tyr Arg Thr Arg Val Arg Lys Asn Ala
                1780                1785                1790
Asp Ser Lys Asn Asn Leu Asn Ala Glu Arg Val Phe Ser Asp Asn Lys
                1795                1800                1805
Asp Ser Lys Lys Gln Asn Leu Lys Asn Asn Ser Lys Asp Phe Asn Asp
                1810                1815                1820
Lys Leu Pro Asn Asn Glu Asp Arg Val Arg Gly Ser Phe Ala Phe Asp
1825                1830                1835                1840
Ser Pro His His Tyr Thr Pro Ile Glu Gly Thr Pro Tyr Cys Phe Ser
                1845                1850                1855
Arg Asn Asp Ser Leu Ser Ser Leu Asp Phe Asp Asp Asp Val Asp
                1860                1865                1870
Leu Ser Arg Glu Lys Ala Glu Leu Arg Lys Ala Lys Glu Asn Lys Glu
                1875                1880                1885
Ser Glu Ala Lys Val Thr Ser His Thr Glu Leu Thr Ser Asn Gln Gln
                1890                1895                1900
Ser Ala Asn Lys Thr Gln Ala Ile Ala Lys Gln Pro Ile Asn Arg Gly
1905                1910                1915                1920
Gln Pro Lys Pro Ile Leu Gln Lys Gln Ser Thr Phe Pro Gln Ser Ser
                1925                1930                1935
Lys Asp Ile Pro Asp Arg Gly Ala Ala Thr Asp Glu Lys Leu Gln Asn
                1940                1945                1950
Phe Ala Ile Glu Asn Thr Pro Val Cys Phe Ser His Asn Ser Ser Leu
                1955                1960                1965
Ser Ser Leu Ser Asp Ile Asp Gln Glu Asn Asn Asn Lys Glu Asn Glu
                1970                1975                1980
Pro Ile Lys Glu Thr Glu Pro Pro Asp Ser Gln Gly Glu Pro Ser Lys
1985                1990                1995                2000
Pro Gln Ala Ser Gly Tyr Ala Pro Lys Ser Phe His Val Glu Asp Thr
                2005                2010                2015
Pro Val Cys Phe Ser Arg Asn Ser Ser Leu Ser Ser Leu Ser Ile Asp
                2020                2025                2030
Ser Glu Asp Asp Leu Leu Gln Glu Cys Ile Ser Ser Ala Met Pro Lys
                2035                2040                2045
Lys Lys Lys Pro Ser Arg Leu Lys Gly Asp Asn Glu Lys His Ser Pro
2050                2055                2060
Arg Asn Met Gly Gly Ile Leu Gly Glu Asp Leu Thr Leu Asp Leu Lys
2065                2070                2075                2080
Asp Ile Gln Arg Pro Asp Ser Glu His Gly Leu Ser Pro Asp Ser Glu
                2085                2090                2095
Asn Phe Asp Trp Lys Ala Ile Gln Glu Gly Ala Asn Ser Ile Val Ser
                2100                2105                2110
Ser Leu His Gln Ala Ala Ala Ala Cys Leu Ser Arg Gln Ala Ser
                2115                2120                2125
Ser Asp Ser Asp Ser Ile Leu Ser Leu Lys Ser Gly Ile Ser Leu Gly
                2130                2135                2140
```

-continued

```
Ser Pro Phe His Leu Thr Pro Asp Gln Glu Lys Pro Phe Thr Ser
2145                2150                2155                2160

Asn Lys Gly Pro Arg Ile Leu Lys Pro Gly Glu Lys Ser Thr Leu Glu
            2165                2170                2175

Thr Lys Lys Ile Glu Ser Glu Ser Lys Gly Ile Lys Gly Gly Lys Lys
            2180                2185                2190

Val Tyr Lys Ser Leu Ile Thr Gly Lys Val Arg Ser Asn Ser Glu Ile
            2195                2200                2205

Ser Gly Gln Met Lys Gln Pro Leu Gln Ala Asn Met Pro Ser Ile Ser
            2210                2215                2220

Arg Gly Arg Thr Met Ile His Ile Pro Gly Val Arg Asn Ser Ser Ser
2225                2230                2235                2240

Ser Thr Ser Pro Val Ser Lys Lys Gly Pro Pro Leu Lys Thr Pro Ala
            2245                2250                2255

Ser Lys Ser Pro Ser Glu Gly Gln Thr Ala Thr Thr Ser Pro Arg Gly
            2260                2265                2270

Ala Lys Pro Ser Val Lys Ser Glu Leu Ser Pro Val Ala Arg Gln Thr
            2275                2280                2285

Ser Gln Ile Gly Gly Ser Ser Lys Ala Pro Ser Arg Ser Gly Ser Arg
            2290                2295                2300

Asp Ser Thr Pro Ser Arg Pro Ala Gln Gln Pro Leu Ser Arg Pro Ile
2305                2310                2315                2320

Gln Ser Pro Gly Arg Asn Ser Ile Ser Pro Gly Arg Asn Gly Ile Ser
            2325                2330                2335

Pro Pro Asn Lys Leu Ser Gln Leu Pro Arg Thr Ser Ser Pro Ser Thr
            2340                2345                2350

Ala Ser Thr Lys Ser Ser Gly Ser Gly Lys Met Ser Tyr Thr Ser Pro
            2355                2360                2365

Gly Arg Gln Met Ser Gln Gln Asn Leu Thr Lys Gln Thr Gly Leu Ser
            2370                2375                2380

Lys Asn Ala Ser Ser Ile Pro Arg Ser Glu Ser Ala Ser Lys Gly Leu
2385                2390                2395                2400

Asn Gln Met Asn Asn Gly Asn Gly Ala Asn Lys Lys Val Glu Leu Ser
            2405                2410                2415

Arg Met Ser Ser Thr Lys Ser Ser Gly Ser Glu Ser Asp Arg Ser Glu
            2420                2425                2430

Arg Pro Val Leu Val Arg Gln Ser Thr Phe Ile Lys Glu Ala Pro Ser
            2435                2440                2445

Pro Thr Leu Arg Arg Lys Leu Glu Glu Ser Ala Ser Phe Glu Ser Leu
            2450                2455                2460

Ser Pro Ser Ser Arg Pro Ala Ser Pro Thr Arg Ser Gln Ala Gln Thr
2465                2470                2475                2480

Pro Val Leu Ser Pro Ser Leu Pro Asp Met Ser Leu Ser Thr His Ser
            2485                2490                2495

Ser Val Gln Ala Gly Gly Trp Arg Lys Leu Pro Pro Asn Leu Ser Pro
            2500                2505                2510

Thr Ile Glu Tyr Asn Asp Gly Arg Pro Ala Lys Arg His Asp Ile Ala
            2515                2520                2525

Arg Ser His Ser Glu Ser Pro Ser Arg Leu Pro Ile Asn Arg Ser Gly
            2530                2535                2540

Thr Trp Lys Arg Glu His Ser Lys His Ser Ser Ser Leu Pro Arg Val
2545                2550                2555                2560

Ser Thr Trp Arg Arg Thr Gly Ser Ser Ser Ser Ile Leu Ser Ala Ser
```

-continued

```
                    2565                2570                2575

Ser Glu Ser Ser Glu Lys Ala Lys Ser Glu Asp Glu Lys His Val Asn
                2580                2585                2590

Ser Ile Ser Gly Thr Lys Gln Ser Lys Glu Asn Gln Val Ser Ala Lys
            2595                2600                2605

Gly Thr Trp Arg Lys Ile Lys Glu Asn Glu Phe Ser Pro Thr Asn Ser
        2610                2615                2620

Thr Ser Gln Thr Val Ser Ser Gly Ala Thr Asn Gly Ala Glu Ser Lys
2625                2630                2635                2640

Thr Leu Ile Tyr Gln Met Ala Pro Ala Val Ser Lys Thr Glu Asp Val
                2645                2650                2655

Trp Val Arg Ile Glu Asp Cys Pro Ile Asn Asn Pro Arg Ser Gly Arg
                2660                2665                2670

Ser Pro Thr Gly Asn Thr Pro Pro Val Ile Asp Ser Val Ser Glu Lys
            2675                2680                2685

Ala Asn Pro Asn Ile Lys Asp Ser Lys Asp Asn Gln Ala Lys Gln Asn
        2690                2695                2700

Val Gly Asn Gly Ser Val Pro Met Arg Thr Val Gly Leu Glu Asn Arg
2705                2710                2715                2720

Leu Asn Ser Phe Ile Gln Val Asp Ala Pro Asp Gln Lys Gly Thr Glu
                2725                2730                2735

Ile Lys Pro Gly Gln Asn Asn Pro Val Pro Val Ser Glu Thr Asn Glu
            2740                2745                2750

Ser Ser Ile Val Glu Arg Thr Pro Phe Ser Ser Ser Ser Ser Ser Lys
        2755                2760                2765

His Ser Ser Pro Ser Gly Thr Val Ala Ala Arg Val Thr Pro Phe Asn
        2770                2775                2780

Tyr Asn Pro Ser Pro Arg Lys Ser Ser Ala Asp Ser Thr Ser Ala Arg
2785                2790                2795                2800

Pro Ser Gln Ile Pro Thr Pro Val Asn Asn Asn Thr Lys Lys Arg Asp
                2805                2810                2815

Ser Lys Thr Asp Ser Thr Glu Ser Ser Gly Thr Gln Ser Pro Lys Arg
            2820                2825                2830

His Ser Gly Ser Tyr Leu Val Thr Ser Val
        2835                2840

(2) INFORMATION FOR SEQ ID NO: 8:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: ral2(yeast)

(xi) SEQUENCE DESCRIPTION: SEQ ID NO: 8:

Leu Thr Gly Ala Lys Gly Leu Gln Leu Arg Ala Leu Arg Arg Ile Ala
1               5                   10                  15

Arg Ile Glu Gln Gly Gly Thr Ala Ile Ser Pro Thr Ser Pro Leu
            20                  25                  30

(2) INFORMATION FOR SEQ ID NO: 9:

(i) SEQUENCE CHARACTERISTICS:
```

(A) LENGTH: 29 amino acids
       (B) TYPE: amino acid
       (C) STRANDEDNESS: single
       (D) TOPOLOGY: linear (ii) MOLECULE TYPE: peptide (vi) ORIGINAL SOURCE:
       (A) ORGANISM: Homo sapiens (vii) IMMEDIATE SOURCE:
       (B) CLONE: m3(mAChR)

(xi) SEQUENCE DESCRIPTION: SEQ ID NO: 9:

Leu Tyr Trp Arg Ile Tyr Lys Glu Thr Glu Lys Arg Thr Lys Glu Leu
1               5                   10                  15

Ala Gly Leu Gln Ala Ser Gly Thr Glu Ala Glu Thr Glu
            20                  25

(2) INFORMATION FOR SEQ ID NO: 10:

(i) SEQUENCE CHARACTERISTICS:
       (A) LENGTH: 29 amino acids
       (B) TYPE: amino acid
       (C) STRANDEDNESS: single
       (D) TOPOLOGY: linear (ii) MOLECULE TYPE: peptide (vi) ORIGINAL SOURCE:
       (A) ORGANISM: Homo sapiens (vii) IMMEDIATE SOURCE:
       (B) CLONE: MCC (xi) SEQUENCE DESCRIPTION: SEQ ID NO: 10:

Leu Tyr Pro Asn Leu Ala Glu Glu Arg Ser Arg Trp Glu Lys Glu Leu
1               5                   10                  15

Ala Gly Leu Arg Glu Glu Asn Glu Ser Leu Thr Ala Met
            20                  25

(2) INFORMATION FOR SEQ ID NO: 11:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (ii) MOLECULE TYPE: cDNA (vi) ORIGINAL SOURCE:
       (A) ORGANISM: Homo sapiens (xi) SEQUENCE DESCRIPTION: SEQ ID NO: 11:

GTATCAAGAC TGTGACTTTT AATTGTAGTT TATCCATTTT                          40

(2) INFORMATION FOR SEQ ID NO: 12:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (ii) MOLECULE TYPE: cDNA (vi) ORIGINAL SOURCE:
       (A) ORGANISM: Homo sapiens (xi) SEQUENCE DESCRIPTION: SEQ ID NO: 12:

```
TTTAGAATTT CATGTTAATA TATTGTGTTC TTTTTAACAG                              40

(2) INFORMATION FOR SEQ ID NO: 13:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 13:

GTAGATTTTA AAAAGGTGTT TTAAAATAAT TTTTTAAGCT                              40

(2) INFORMATION FOR SEQ ID NO: 14:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 14:

AAGCAATTGT TGTATAAAAA CTTGTTTCTA TTTTATTTAG                              40

(2) INFORMATION FOR SEQ ID NO: 15:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 15:

GTAACTTTTC TTCATATAGT AAACATTGCC TTGTGTACTC                              40

(2) INFORMATION FOR SEQ ID NO: 16:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 16:

NNNNNNNNNN NNNGTCCCTT TTTTTAAAAA AAAAAAATAG                              40

(2) INFORMATION FOR SEQ ID NO: 17:

(i) SEQUENCE CHARACTERISTICS:
```

(A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 17:

GTAAGTAACT TGGCAGTACA ACTTATTTGA AACTTTAATA                                40

(2) INFORMATION FOR SEQ ID NO: 18:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 18:

ATACAAGATA TTGATACTTT TTTATTATTT GTGGTTTTAG                                40

(2) INFORMATION FOR SEQ ID NO: 19:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 19:

GTAAGTTACT TGTTTCTAAG TGATAAAACA GYGAAGAGCT                                40

(2) INFORMATION FOR SEQ ID NO: 20:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 20:

AATAAAAACA TAACTAATTA GGTTTCTTGT TTTATTTTAG                                40

(2) INFORMATION FOR SEQ ID NO: 21:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 21:

GTTAGTAAAT TSCCTTTTTT GTTTGTGGGT ATAAAAATAG                              40

(2) INFORMATION FOR SEQ ID NO: 22:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 22:

ACCATTTTTG CATGTACTGA TGTTAACTCC ATCTTAACAG                              40

(2) INFORMATION FOR SEQ ID NO: 23:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 23:

GTAAATAAAT TATTTTATCA TATTTTTTAA AATTATTTAA                              40

(2) INFORMATION FOR SEQ ID NO: 24:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 24:

CATGATGTTA TCTGTATTTA CCTATAGTCT AAATTATACC ATCTATAATG TGCTTAATTT        60

TTAG                                                                    64

(2) INFORMATION FOR SEQ ID NO: 25:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 25:

GTAACAGAAG ATTACAAACC CTGGTCACTA ATGCCATGAC TACTTTGCTA AG    52

(2) INFORMATION FOR SEQ ID NO: 26:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 26:

GGATATTAAA GTCGTAATTT TGTTTCTAAA CTCATTTGGC CCACAG    46

(2) INFORMATION FOR SEQ ID NO: 27:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 27:

GTATGTTCTC TATAGTGTAC ATCGTAGTGC ATGTTTCAAA    40

(2) INFORMATION FOR SEQ ID NO: 28:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 28:

CATCATTGCT CTTCAAATAA CAAAGCATTA TGGTTTATGT TGATTTTATT TTTCAG    56

(2) INFORMATION FOR SEQ ID NO: 29:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 29:

GTAAGACAAA AATGTTTTTT AATGACATAG ACAATTACTG GTG    43

(2) INFORMATION FOR SEQ ID NO: 30:

(i) SEQUENCE CHARACTERISTICS:
        (A) LENGTH: 40 base pairs

```
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 30:

TTAGATGATT GTCTTTTTCC TCTTGCCCTT TTTAAATTAG                    40

(2) INFORMATION FOR SEQ ID NO: 31:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 31:

GTATGTTTTT ATAACATGTA TTTCTTAAGA TAGCTCAGGT ATGA               44

(2) INFORMATION FOR SEQ ID NO: 32:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 32:

GCTTGGCTTC AAGTTGNCTT TTTAATGATC CTCTATTCTG TATTTAATTT ACAG    54

(2) INFORMATION FOR SEQ ID NO: 33:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 33:

GTACTATTTA GAATTTCACC TGTTTTTCTT TTTTCTCTTT TTCTTTGAGG CAGGGTCTCA    60

CTCTG                                                                65

(2) INFORMATION FOR SEQ ID NO: 34:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA
```

```
    (vi) ORIGINAL SOURCE:
         (A) ORGANISM: Homo sapiens (xi) SEQUENCE DESCRIPTION: SEQ ID NO: 34:

GCAACTAGTA TGATTTTATG TATAAATTAA TCTAAAATTG ATTAATTTCC AG        52

(2) INFORMATION FOR SEQ ID NO: 35:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 35:

GTACCTTTGA AAACATTTAG TACTATAATA TGAATTTCAT GT                  42

(2) INFORMATION FOR SEQ ID NO: 36:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 36:

CCAACTCNAA TTAGATGACC CATATTCAGA AACTTACTAG                     40

(2) INFORMATION FOR SEQ ID NO: 37:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 37:

GTATATATAG AGTTTTATAT TACTTTTAAA GTACAGAATT CATACTCTCA AAAA     54

(2) INFORMATION FOR SEQ ID NO: 38:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 38:

ATTGTGACCT TAATTTGTG ATCTCTTGAT TTTTATTTCA G                    41
```

(2) INFORMATION FOR SEQ ID NO: 39:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 39:

TCCCCGCCTG CCGCTCTC                                            18

(2) INFORMATION FOR SEQ ID NO: 40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 40:

GCAGCGGCGG CTCCCGTG                                            18

(2) INFORMATION FOR SEQ ID NO: 41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 41:

GTGAACGGCT CTCATGCTGC                                        20

(2) INFORMATION FOR SEQ ID NO: 42:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 42:

ACGTGCGGGG AGGAATGGA                                           19

(2) INFORMATION FOR SEQ ID NO: 43:

(i) SEQUENCE CHARACTERISTICS:
        (A) LENGTH: 24 base pairs
        (B) TYPE: nucleic acid (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 43:

ATGATATCTT ACCAAATGAT ATAC                                                  24

(2) INFORMATION FOR SEQ ID NO: 44:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 44:

TTATTCCTAC TTCTTCTATA CAG                                                   23

(2) INFORMATION FOR SEQ ID NO: 45:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 45:

TACCCATGCT GGCTCTTTTT C                                                     21

(2) INFORMATION FOR SEQ ID NO: 46:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 46:

TGGGGCCATC TTGTTCCTGA                                                       20

(2) INFORMATION FOR SEQ ID NO: 47:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 47:

ACATTAGGCA CAAAGCTTGC AA         22

(2) INFORMATION FOR SEQ ID NO: 48:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 48:

ATCAAGCTCC AGTAAGAAGG TA         22

(2) INFORMATION FOR SEQ ID NO: 49:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 49:

TGCGGCTCCT GGGTTGTTG         19

(2) INFORMATION FOR SEQ ID NO: 50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 50:

GCCCCTTCCT TTCTGAGGAC         20

(2) INFORMATION FOR SEQ ID NO: 51:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 51:

TTTTCTCCTG CCTCTTACTG C         21

(2) INFORMATION FOR SEQ ID NO: 52:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 52:

ATGACACCCC CCATTCCCTC                                               20

(2) INFORMATION FOR SEQ ID NO: 53:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 53:

CCACTTAAAG CACATATATT TAGT                                          24

(2) INFORMATION FOR SEQ ID NO: 54:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 54:

GTATGGAAAA TAGTGAAGAA CC                                            22

(2) INFORMATION FOR SEQ ID NO: 55:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 55:

TTCTTAAGTC CTGTTTTTCT TTTG                                          24

(2) INFORMATION FOR SEQ ID NO: 56:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 56:

TTTAGAACCT TTTTTGTGTT GTG                                              23

(2) INFORMATION FOR SEQ ID NO: 57:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 57:

CTCAGATTAT ACACTAAGCC TAAC                                             24

(2) INFORMATION FOR SEQ ID NO: 58:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 58:

CATGTCTCTT ACAGTAGTAC CA                                               22

(2) INFORMATION FOR SEQ ID NO: 59:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 59:

AGGTCCAAGG GTAGCCAAGG                                                  20

(2) INFORMATION FOR SEQ ID NO: 60:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 60:

```
TAAAAATGGA TAAACTACAA TTAAAAG                                           27

(2) INFORMATION FOR SEQ ID NO: 61:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: cDNA (vi) ORIGINAL SOURCE:
          (A) ORGANISM: Homo sapiens (xi) SEQUENCE DESCRIPTION: SEQ ID NO: 61:

AAATACAGAA TCATGTCTTG AAGT                                              24

(2) INFORMATION FOR SEQ ID NO: 62:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: cDNA (vi) ORIGINAL SOURCE:
          (A) ORGANISM: Homo sapiens (xi) SEQUENCE DESCRIPTION: SEQ ID NO: 62:

ACACCTAAAG ATGACAATTT GAG                                               23

(2) INFORMATION FOR SEQ ID NO: 63:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: cDNA (vi) ORIGINAL SOURCE:
          (A) ORGANISM: Homo sapiens (xi) SEQUENCE DESCRIPTION: SEQ ID NO: 63:

TAACTTAGAT AGCAGTAATT TCCC                                              24

(2) INFORMATION FOR SEQ ID NO: 64:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: cDNA (vi) ORIGINAL SOURCE:
          (A) ORGANISM: Homo sapiens (xi) SEQUENCE DESCRIPTION: SEQ ID NO: 64:

ACAATAAACT GGAGTACACA AGG                                               23

(2) INFORMATION FOR SEQ ID NO: 65:

(i) SEQUENCE CHARACTERISTICS:
          (A) LENGTH: 23 base pairs
```

```
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 65:

ATAGGTCATT GCTTCTTGCT GAT                                             23

(2) INFORMATION FOR SEQ ID NO: 66:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 66:

TGAATTTTAA TGGATTACCT AGGT                                            24

(2) INFORMATION FOR SEQ ID NO: 67:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 67:

CTTTTTTTGC TTTTACTGAT TAACG                                           25

(2) INFORMATION FOR SEQ ID NO: 68:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 68:

TGTAATTCAT TTTATTCCTA ATAGCTC                                         27

(2) INFORMATION FOR SEQ ID NO: 69:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
```

(A) ORGANISM: Homo sapiens (xi) SEQUENCE DESCRIPTION: SEQ ID NO: 69:

GGTAGCCATA GTATGATTAT TTCT                                            24

(2) INFORMATION FOR SEQ ID NO: 70:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 70:

CTACCTATTT TTATACCCAC AAAC                                            24

(2) INFORMATION FOR SEQ ID NO: 71:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 71:

AAGAAAGCCT ACACCATTTT TGC                                             23

(2) INFORMATION FOR SEQ ID NO: 72:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 72:

GATCATTCTT AGAACCATCT TGC                                             23

(2) INFORMATION FOR SEQ ID NO: 73:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 73:

ACCTATAGTC TAAATTATAC CATC                                            24

(2) INFORMATION FOR SEQ ID NO: 74:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 74:

GTCATGGCAT TAGTGACCAG          20

(2) INFORMATION FOR SEQ ID NO: 75:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 75:

AGTCGTAATT TTGTTTCTAA ACTC      24

(2) INFORMATION FOR SEQ ID NO: 76:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 76:

TGAAGGACTC GGATTTCACG C         21

(2) INFORMATION FOR SEQ ID NO: 77:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 77:

TCATTCACTC ACAGCCTGAT GAC       23

(2) INFORMATION FOR SEQ ID NO: 78:

(i) SEQUENCE CHARACTERISTICS:
        (A) LENGTH: 22 base pairs
        (B) TYPE: nucleic acid
        (C) STRANDEDNESS: single
        (D) TOPOLOGY: linear

```
        (ii) MOLECULE TYPE: cDNA (vi) ORIGINAL SOURCE:
             (A) ORGANISM: Homo sapiens (xi) SEQUENCE DESCRIPTION: SEQ ID NO: 78:

GCTTTGAAAC ATGCACTACG AT                                              22

(2) INFORMATION FOR SEQ ID NO: 79:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: cDNA (vi) ORIGINAL SOURCE:
             (A) ORGANISM: Homo sapiens (xi) SEQUENCE DESCRIPTION: SEQ ID NO: 79:

AAACATCATT GCTCTTCAAA TAAC                                            24

(2) INFORMATION FOR SEQ ID NO: 80:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: cDNA (vi) ORIGINAL SOURCE:
             (A) ORGANISM: Homo sapiens (xi) SEQUENCE DESCRIPTION: SEQ ID NO: 80:

TACCATGATT TAAAAATCCA CCAG                                            24

(2) INFORMATION FOR SEQ ID NO: 81:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: cDNA (vi) ORIGINAL SOURCE:
             (A) ORGANISM: Homo sapiens (xi) SEQUENCE DESCRIPTION: SEQ ID NO: 81:

GATGATTGTC TTTTTCCTCT TGC                                             23

(2) INFORMATION FOR SEQ ID NO: 82:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: cDNA (vi) ORIGINAL SOURCE:
             (A) ORGANISM: Homo sapiens (xi) SEQUENCE DESCRIPTION: SEQ ID NO: 82:
```

CTGAGCTATC TTAAGAAATA CATG                                    24

(2) INFORMATION FOR SEQ ID NO: 83:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 83:

TTTTAAATGA TCCTCTATTC TGTAT                                   25

(2) INFORMATION FOR SEQ ID NO: 84:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 84:

ACAGAGTCAG ACCCTGCCTC AAAG                                    24

(2) INFORMATION FOR SEQ ID NO: 85:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 85:

TTTCTATTCT TACTGCTAGC ATT                                     23

(2) INFORMATION FOR SEQ ID NO: 86:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 86:

ATACACAGGT AAGAAATTAG GA                                      22

(2) INFORMATION FOR SEQ ID NO: 87:

(i) SEQUENCE CHARACTERISTICS:

```
        (A) LENGTH: 22 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 87:

TAGATGACCC ATATTCTGTT TC                                              22

(2) INFORMATION FOR SEQ ID NO: 88:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 88:

CAATTAGGTC TTTTTGAGAG TA                                              22

(2) INFORMATION FOR SEQ ID NO: 89:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 89:

GTTACTGCAT ACACATTGTG AC                                              22

(2) INFORMATION FOR SEQ ID NO: 90:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 90:

GCTTTTTGTT TCCTAACATG AAG                                             23

(2) INFORMATION FOR SEQ ID NO: 91:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA
```

(vi) ORIGINAL SOURCE:
            (A) ORGANISM: Homo sapiens (xi) SEQUENCE DESCRIPTION: SEQ ID NO: 91:

TCTCCCACAG GTAATACTCC C                                              21

(2) INFORMATION FOR SEQ ID NO: 92:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 92:

GCTAGAACTG AATGGGGTAC G                                              21

(2) INFORMATION FOR SEQ ID NO: 93:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 93:

CAGGACAAAA TAATCCTGTC CC                                             22

(2) INFORMATION FOR SEQ ID NO: 94:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 94:

ATTTTCTTAG TTTCATTCTT CCTC                                           24

(2) INFORMATION FOR SEQ ID NO: 95:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 95:

AGAAGGATCC CTTGTGCAGT GTGGA                                          25

(2) INFORMATION FOR SEQ ID NO: 96:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 96:

GACAGGATCC TGAAGCTGAG TTTG        24

(2) INFORMATION FOR SEQ ID NO: 97:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 97:

TCAGAAAGTG CTGAAGAG        18

(2) INFORMATION FOR SEQ ID NO: 98:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 98:

GGAATAATTA GGTCTCCAA        19

(2) INFORMATION FOR SEQ ID NO: 99:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 99:

GCAAATCCTA AGAGAGAACA A        21

(2) INFORMATION FOR SEQ ID NO: 100:

(i) SEQUENCE CHARACTERISTICS:
        (A) LENGTH: 19 base pairs
        (B) TYPE: nucleic acid
        (C) STRANDEDNESS: single

```
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 100:

GATGGCAAGC TTGAGCCAG                                                      19

(2) INFORMATION FOR SEQ ID NO: 101:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 101:

GTTCCAGCAG TGTCACAG                                                       18

(2) INFORMATION FOR SEQ ID NO: 102:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 102:

GGGAGATTTC GCTCCTGA                                                       18
```